(12) United States Patent
Tomonaga et al.

(10) Patent No.: US 6,199,017 B1
(45) Date of Patent: Mar. 6, 2001

(54) BIOCHEMICAL INFORMATION PROCESSING APPARATUS, BIOCHEMICAL INFORMATION PROCESSING METHOD, AND BIOCHEMICAL INFORMATION RECORDING MEDIUM

(75) Inventors: Atsushi Tomonaga, Musashino; Fumio Tamura, Inashiki-gun, both of (JP)

(73) Assignee: Kureha Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 08/913,557

(22) PCT Filed: Mar. 18, 1996

(86) PCT No.: PCT/JP96/00709

§ 371 Date: Sep. 16, 1997

§ 102(e) Date: Sep. 16, 1997

(87) PCT Pub. No.: WO96/29659

PCT Pub. Date: Sep. 26, 1996

(30) Foreign Application Priority Data

Mar. 17, 1995 (JP) ....................................... 7-59196
Mar. 17, 1995 (JP) ....................................... 7-59200
Apr. 28, 1995 (JP) ....................................... 7-106173
Apr. 28, 1995 (JP) ....................................... 7-106181

(51) Int. Cl.$^7$ ................................................. G06F 17/00
(52) U.S. Cl. ......................... 702/19; 702/27; 702/32; 700/266
(58) Field of Search ............... 702/19, 21–23, 702/27–32, 123, FOR 115–FOR 114, FOR 170, FOR 171; 382/128–130, 133, 134; 364/528.01; 346/33 ME; 436/43, 50, 55, 63, 807, 808; 422/50, 62, 63, 67, 68.1, 81, 119; 700/266, 267

(56) References Cited

U.S. PATENT DOCUMENTS 5,577,239 * 11/1996 Moore et al. ..................... 702/27
5,684,711 * 11/1997 Agratiotis et al. ................ 702/27
5,717,778 * 2/1998 Chu et al. ........................ 382/133

OTHER PUBLICATIONS

Symposium on Chemical Information and Computer Science on Oct. 19, 1990/Symposium on Structure Activity Relationships: Abstracts of Lectures, vol. 13–18, pp. 1–2, Sections 3.4–3.6.

(List continued on next page.)

*Primary Examiner*—Hal Wachsman
(74) *Attorney, Agent, or Firm*—Beyer Weaver & Thomas, LLP

(57) ABSTRACT

A biochemical information processing apparatus includes a storage means storing biochemical information, input means for accepting input of data, reaction scheme detection means for detecting a chemical reaction scheme involving a compound, based on the data, and display means for displaying a reaction scheme diagram of the chemical reaction scheme. The storage means includes a compound information file, an enzyme information file, and a relation information file. The relation information file stores a list showing the relation among compound numbers of compounds, enzyme numbers of enzymes with either pertinent compound being a substrate, and enzyme numbers of enzymes with either pertinent compound being a product. The reaction scheme detection means includes a first process portion for preparing canonical data of the compound from the data and searching the compound information file based thereon to read out a compound number. It also includes a second process portion for reading an enzyme number of an enzyme with the compound being a substrate or a product, a third process portion for reading a compound number of another compound constituting a reaction system with the enzyme and additional information of the enzyme, and a fourth process portion for indicating a reaction scheme diagram of the compound on the display means.

29 Claims, 50 Drawing Sheets

OTHER PUBLICATIONS

H.L. Morgan, The Generation of a Unique Machine Description for Chemical Structures—A Technique Developed at Chemical Abstracts Service, Jan. 15, 1965, Chemical Abstracts Service, The Ohio State University, J Chem. Doc. 1965, 5(2), 107–113.

Sandor Barcza, et al., Computerized Retrieval of Information on Biosynthesis and Metabolic Pathways, Feb. 22, 1990, Sandoz Research Institute, J. Chem. Inf. Comput. Sci. 1990, 30, 243–251.

Peter D. Karp and Michael L. Mavrovouniotis, Representing, Analyzing, and Synthesizing Biochemical Pathways, Apr. 1994, IEEE Expert, 1994, 9(2), 11–21.

Information Science Abstracts, vol. 13 No. 1, 1978, 25–26. (No Month).

G. A. Hopkinson, Recent Developments in Reaction Searching, Dec. 12, 1989, ORAC Ltd.

\* cited by examiner

Fig. 3

COMPOUND INFO FILE                                          31

| COMPOUND NUMBER | CANONICAL DATA | REFERENCE DATA |
|---|---|---|
| C1 | 1%2% ---------------- | NAME, LITERATURE, PHYSICAL PROPERTIES, ETC. |
| C2 | ---------------- | |
| C3 | ---------------- | |
| C4 | ---------------- | |
| C5 | ---------------- | |
| C6 | ---------------- | |
| C7 | ---------------- | |

Fig. 4

ENZYME INFO FILE 32

| ENZYME NUMBER | (SUBSTRATE) COMPOUND NUMBER | (PRODUCT) COMPOUND NUMBER | REFERENCE DATA |
|---|---|---|---|
| E1 | C1 | C2 | NAME, LITERATURE, PHYSICAL PROPERTIES, ETC. |
| E2 | C2 | C3 | |
| E3 | C3 | C4 | |
| E4 | C3 | C6 | |
| E5 | C5 | C6 | |
| E6 | C6 | C7 | |

RECEPTOR INFO FILE

| RECEPTOR NUMBER | (AGONIST) COMPOUND NUMBER | (ANTAGONIST) COMPOUND NUMBER | REFERENCE DATA |
|---|---|---|---|
| R1 | C6 | | NAME, LITERATURE, PHYSICAL PROPERTIES, ACTION, ETC. |
| R2 | | C8 | |
| R3 | R10, C11 | | |
| R4 | C12 | C7, C9 | |

Fig. 6

RELATION INFO FILE 33

| COMPOUND NUMBER | (SUBSTRATE) ENZYME NUMBER | (PRODUCT) ENZYME NUMBER | (INHIBITION) ENZYME NUMBER | (AGONISM) RECEPTOR NUMBER | (ANTAGONISM) RECEPTOR NUMBER |
|---|---|---|---|---|---|
| C1 | E1 | | | | |
| C2 | E2 | E1 | | | |
| C3 | E3,E4 | E2 | | | |
| C4 | | E3 | | | |
| C5 | E5 | | | | |
| C6 | E6 | E5 | E4 | R1 | |
| C7 | | E6 | | | R4 |
| C8 | | | | | R2 |
| C9 | | | | | R4 |
| C10 | | | | R3 | |
| C11 | | | | R3 | |
| C12 | | | | R4 | |

IMAGE DATA 80a (MOLECULAR STRUCTURE DIAGRAM)

BOND TABLE DATA 81a

| NUMBER OF ATOMS | NUMBER OF BONDS |
|---|---|
| 7 | 7 |

| ATOM NUMBER | X-COORDINATE | Y-COORDINATE | Z-COORDINATE | ELEMENT SYMBOL | CHARGE | MASS | BONDING ATOM PAIR | TYPE OF BOND | UP/DOWN |
|---|---|---|---|---|---|---|---|---|---|
| 1 | 3.0386 | -2.4082 | 0.0000 | C | 0 | 0 | 1  2 | 2 | 0 |
| 2 | 3.0386 | -0.9082 | 0.0000 | C | 0 | 0 | 2  3 | 1 | 0 |
| 3 | 1.7396 | -0.1582 | 0.0000 | C | 0 | 0 | 3  4 | 2 | 0 |
| 4 | 0.4405 | -0.9082 | 0.0000 | N | 0 | 0 | 4  5 | 1 | 0 |
| 5 | 0.4405 | -2.4082 | 0.0000 | C | 0 | 0 | 5  6 | 2 | 0 |
| 6 | 1.7396 | -3.1582 | 0.0000 | C | 0 | 0 | 6  1 | 1 | 0 |
| 7 | 4.3376 | -3.1582 | 0.0000 | C | 0 | 0 | 1  7 | 1 | 0 |

CANONICAL DATA 82a

1%1%1-2%3%5%N/6%7/

IMAGE DATA 80b (MOLECULAR STRUCTURE DIAGRAM)

BOND TABLE DATA 81b

| NUMBER OF ATOMS | NUMBER OF BONDS |
|---|---|
| 7 | 7 |

| ATOM NUMBER | X-COORDINATE | Y-COORDINATE | Z-COORDINATE | ELEMENT SYMBOL | CHARGE | MASS | BONDING ATOM PAIR | TYPE OF BOND | UP/DOWN |
|---|---|---|---|---|---|---|---|---|---|
| 1 | 3.5200 | -4.7362 | 0.0000 | C | 0 | 0 | 1 2 | 1 | 0 |
| 2 | 3.5514 | -3.2366 | 0.0000 | C | 0 | 0 | 2 3 | 1 | 0 |
| 3 | 4.8659 | -2.5139 | 0.0000 | C | 0 | 0 | 3 4 | 2 | 0 |
| 4 | 4.8973 | -1.0143 | 0.0000 | C | 0 | 0 | 2 5 | 2 | 0 |
| 5 | 2.2684 | -2.4595 | 0.0000 | C | 0 | 0 | 5 6 | 1 | 0 |
| 6 | 2.2998 | -0.9599 | 0.0000 | C | 0 | 0 | 4 7 | 1 | 0 |
| 7 | 3.6143 | -0.2372 | 0.0000 | N | 0 | 0 | 7 6 | 2 | 0 |

CANONICAL DATA 82b

1%1%1-2%3%5%N/6%7/

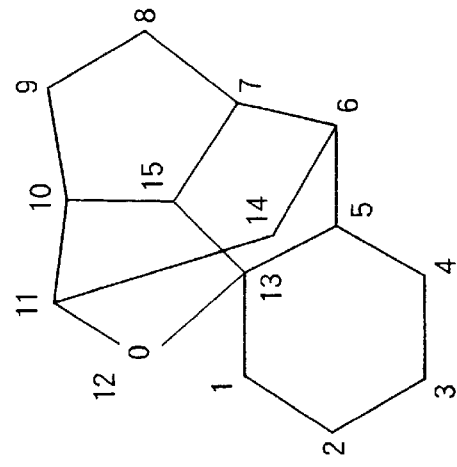
Fig. 10B
IMAGE DATA 80d
(MOLECULAR STRUCTURE DIAGRAM)
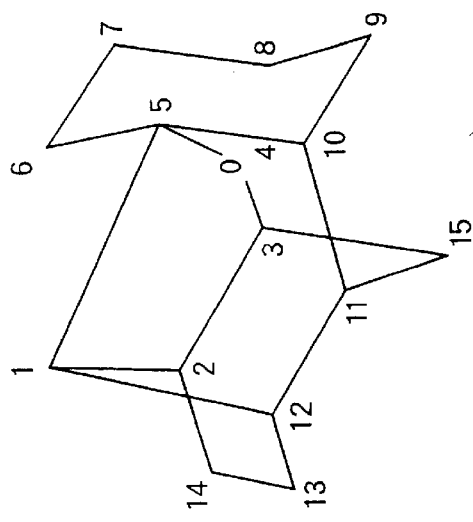
Fig. 10A
IMAGE DATA 80c (MOLECULAR STRUCTURE DIAGRAM)
Fig. 10C
CANONICAL DATA 82c
1-1-1-01-2-2-3-3-4-5-6-7-8-9-/6-8/7-
10/10-14/11-15/12-13/

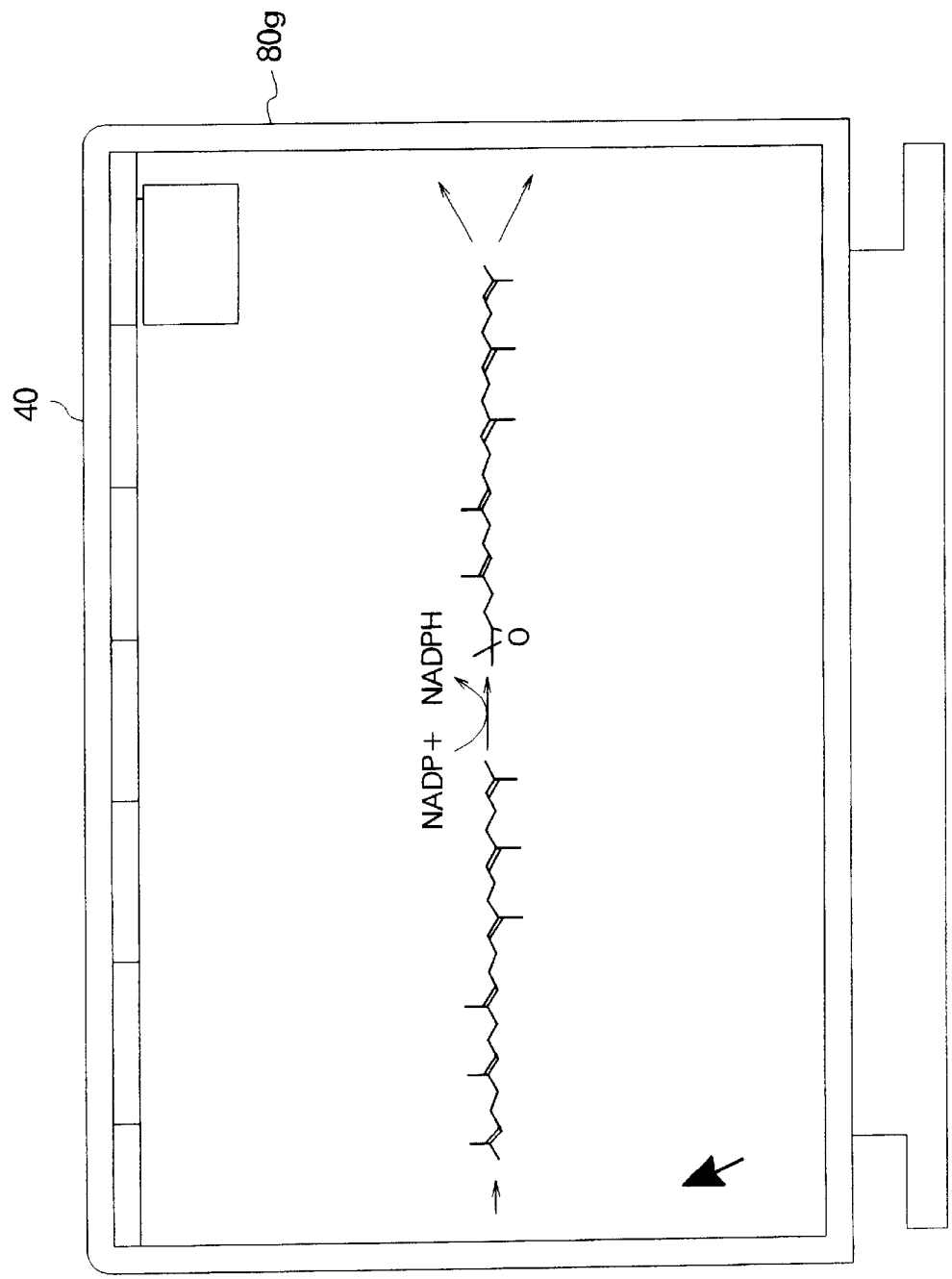

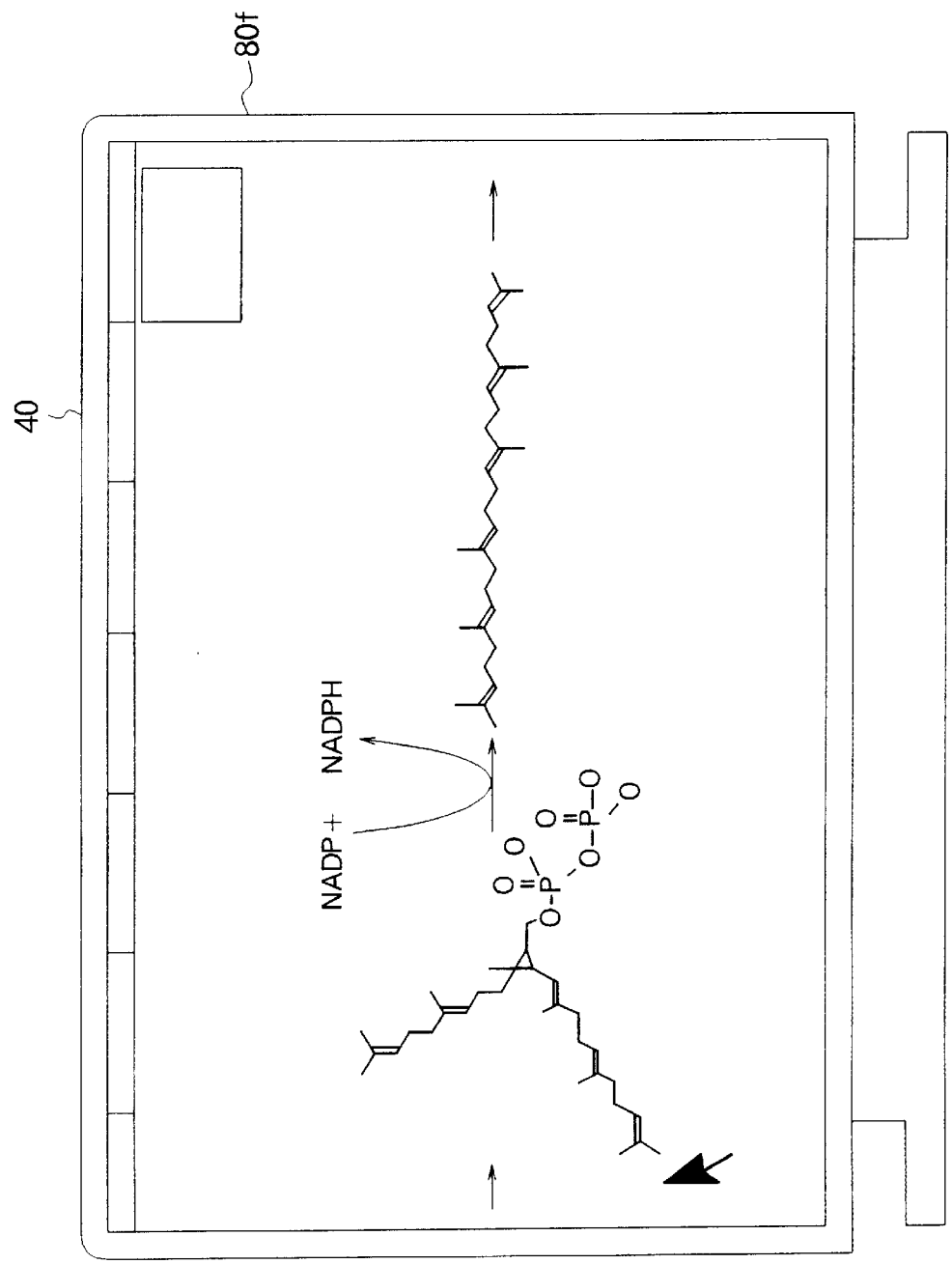

Fig. 18A

BOND TABLE 81

ATOMIC TABLE

| INPUT NUMBER | X-COORDINATE | Y-COORDINATE | ELEMENT SYMBOL | ATTRIBUTE | NUMBER OF ATOMS |
|---|---|---|---|---|---|
| 1 | 3.0386 | −2.4082 | C | | 7 |
| 2 | 3.0386 | −0.9082 | C | | |
| 3 | 1.7396 | −0.1582 | C | | NUMBER OF BONDS |
| 4 | 0.4405 | −0.9082 | N | | |
| 5 | 0.4405 | −2.4082 | C | | 7 |
| 6 | 1.7396 | −3.1582 | C | | |
| 7 | 4.3376 | −3.1582 | C | | |

ATOMIC PAIR TABLE 81d

| BONDING ATOM PAIR | | TYPE OF BOND | STRUCTURE |
|---|---|---|---|
| 1 | 2 | 2 | CYCLIC |
| 2 | 3 | 1 | CYCLIC |
| 3 | 4 | 2 | CYCLIC |
| 4 | 5 | 1 | CYCLIC |
| 5 | 6 | 2 | CYCLIC |
| 6 | 1 | 1 | CYCLIC |
| 1 | 7 | 1 | CHAIN |

Fig. 22A

BOND TABLE 81

ATOMIC TABLE 81e

| INPUT NUMBER | X-COORDINATE | Y-COORDINATE | ELEMENT SYMBOL | ATTRIBUTE | NUMBER OF ATOMS |
|---|---|---|---|---|---|
| 1 | – | – | C | | 8 |
| 2 | – | – | C | | |
| 3 | – | – | N | | NUMBER OF BONDS |
| 4 | – | – | C | | 8 |
| 5 | – | – | C | | |
| 6 | – | – | C | | |
| 7 | – | – | C | | |
| 8 | – | – | C | | |

Fig. 22B

ATOMIC PAIR TABLE 81f

| BONDING ATOM PAIR | | TYPE OF BOND | STRUCTURE |
|---|---|---|---|
| 1 | 2 | 1 | |
| 2 | 3 | 2 | |
| 3 | 4 | 1 | |
| 4 | 5 | 1 | |
| 5 | 6 | 1 | |
| 6 | 1 | 1 | |
| 5 | 7 | 1 | |
| 1 | 8 | 1 | |

INPUT NUMBER

Fig. 25 n = 0

| i | $a_i$ | $b_{ij}$ | $d_{ij}$ | $c_i^0$ |
|---|---|---|---|---|
| 1 | 6 | (3, 0, 0, 0) | (3, 2, 3, 0) | 5 |
| 2 | 6 | (1, 1, 0, 0) | (2, 3, 2, 2) | 2 |
| 3 | 7 | (1, 1, 0, 0) | (2, 2, 4, 0) | 6 |
| 4 | 6 | (2, 0, 0, 0) | (2, 3, 2, 2) | 3 |
| 5 | 6 | (3, 0, 0, 0) | (3, 2, 3, 0) | 5 |
| 6 | 6 | (2, 0, 0, 0) | (2, 4, 2, 0) | 4 |
| 7 | 6 | (1, 0, 0, 0) | (1, 2, 2, 3) | 1 |
| 8 | 6 | (1, 0, 0, 0) | (1, 2, 2, 3) | 1 |

| $i$ | $V_{ij}^1$ | $C_i^1$ |
|---|---|---|
| 1 | (1, 1, 0, 1, 0, 0) | 6 |
| 2 | (0, 0, 0, 0, 1, 1) | 2 |
| 3 | (0, 1, 1, 0, 0, 0) | 7 |
| 4 | (0, 0, 0, 1, 1, 0) | 3 |
| 5 | (1, 0, 1, 1, 0, 0) | 5 |
| 6 | (0, 0, 0, 0, 2, 0) | 4 |
| 7 | (0, 0, 0, 0, 1, 0) | 1 |
| 8 | (0, 0, 0, 0, 1, 0) | 1 |

| i | $V_{ij}^2$ | $C_i^2$ |
|---|---|---|
| 1 | (1, 1, 0, 1, 0, 0, 0) | 7 |
| 2 | (0, 0, 0, 0, 0, 1, 1) | 3 |
| 3 | (0, 1, 1, 0, 0, 0, 0) | 8 |
| 4 | (0, 0, 0, 0, 1, 0, 1) | 4 |
| 5 | (1, 0, 1, 1, 0, 0, 0) | 6 |
| 6 | (0, 0, 0, 0, 1, 1, 0) | 5 |
| 7 | (0, 0, 0, 0, 1, 0, 0) | 2 |
| 8 | (0, 0, 0, 0, 0, 1, 0) | 1 |

$N_2 = 8$

CANONICAL NUMBER

Fig. 36A

BOND TABLE 81
ATOMIC TABLE

| CANONICAL NUMBER | X-COORDINATE | Y-COORDINATE | ELEMENT SYMBOL | ATTRIBUTE | NUMBER OF ATOMS |
|---|---|---|---|---|---|
| 1 | – | – | N | | 8 |
| 2 | – | – | C | | |
| 3 | – | – | C | | NUMBER OF BONDS |
| 4 | – | – | C | | |
| 5 | – | – | C | | 8 |
| 6 | – | – | C | | |
| 7 | – | – | C | | |
| 8 | – | – | C | | |

Fig. 36B

ATOMIC PAIR TABLE 81h

| BONDING ATOM PAIR | | TYPE OF BOND | STRUCTURE |
|---|---|---|---|
| 5 | 3 | 1 | |
| 3 | 1 | 2 | |
| 1 | 2 | 1 | |
| 2 | 4 | 1 | |
| 4 | 6 | 1 | |
| 6 | 5 | 1 | |
| 4 | 7 | 1 | |
| 5 | 8 | 1 | |

Fig. 37

| K | PK | TK | SK |
|---|----|----|----|
| 1 | ... | ... | N |
| 2 | 1 | — | C |
| 3 | 1 | = | C |
| 4 | 2 | — | C |
| 5 | 3 | — | C |
| 6 | 4 | — | C |
| 7 | 4 | — | C |
| 8 | 5 | — | C |

| $\ell$ | $R\ell^1$ | $R\ell^2$ | $H\ell$ |
|---|---|---|---|
| 1 | 5 | 6 | — |

IMAGE DATA 80e (MOLECULAR STRUCTURE DIAGRAM OF C60)

CANONICAL DATA 82d

RELATION INFO FILE 33

| COMPOUND NUMBER | (SUBSTRATE) ENZYME NUMBER | (PRODUCT) ENZYME NUMBER | (INHIBITION) ENZYME NUMBER |
|---|---|---|---|
| C1 | E1 | | |
| C2 | E2 | E1 | |
| C3 | E3, E4 | E2 | |
| C4 | | E3 | |
| C5 | E5 | | |
| C6 | E6 | E5 | E4 |
| C7 | | E6 | |

BIOCHEMICAL INFORMATION PROCESSING APPARATUS, BIOCHEMICAL INFORMATION PROCESSING METHOD, AND BIOCHEMICAL INFORMATION RECORDING MEDIUM

TECHNICAL FIELD

The present invention relates to a processing apparatus and processing method for processing information in the biochemical field, and more particularly, to a processing apparatus and processing method that can search for a reaction path of a bio-related compound and continuously display the reaction path and that can obtain information concerning bio-related substances.

Further, the present invention concerns an information recording medium (computer program product), such as a flexible disk or a magnetic tape, in which biochemical information is recorded, and more particularly, the invention concerns an information recording medium having records of information for searching for a reaction path of a bio-related compound, information for continuously displaying the reaction path, information concerning the bio-related substances, and so on.

BACKGROUND ART

Compound database systems and programs storing compound information and reaction database systems and programs storing reaction information of compound have been developed heretofore. The compound database systems and programs store the compound information such as the physical properties and action of the existing compounds, and access is made to the compound information with the structure of a compound as a key. The reaction database systems store the reaction information of the existing compounds, and access is made to the reaction information with the structure of a compound as a key.

An example of such a compound database is "MACCS" which is a compound control system available from MDL Inc., Co., the United States. Examples of the reaction database systems include the integrated chemical information control system "ISIS" and reaction information control system "REACCS" available from MDL Inc., Co., the United States.

There are, however, no conventional compound/reaction database systems storing the relationship between compound and enzyme and the information concerning the bio-related substances in an integrated manner. Because of it, using the structure of a compound as a key, one was unable to efficiently obtain the information concerning the enzymes or the biochemical information related to the enzymes, substrates, and products. Also, there are no conventional compound/reaction database systems including a reaction path of plural compounds constructed in an integrated manner. It was, therefore, not possible to efficiently search for the reaction path involving a plurality of compounds.

Further, there are no conventional compound/reaction database systems collectively storing information concerning receptors existing for control of bio-function or for transmission of information in vivo, and the information concerning the bio-related substances (agonists and antagonists). It was, therefore, not possible to efficiently obtain the biochemical information related to the receptors, agonists, and antagonists.

An object of the present invention is to provide a biochemical information processing apparatus, biochemical information processing method, and information recording medium (computer program product), solving the above problems, which can permit one, even in the case of the structure of a compound being used as a key, to efficiently obtain the information concerning the enzymes or the biochemical information related to the enzymes, substrates, and products, which can permit one to efficiently search for a reaction path involving a plurality of compounds, and which can permit one to efficiently obtain the biochemical information related to the receptors, agonists, and antagonists.

DISCLOSURE OF INVENTION

First explained is the biochemical information processing apparatus of the present invention.

The biochemical information processing apparatus of the present invention is a biochemical information processing apparatus comprising storage means for storing biochemical information about compounds and enzymes, input means for accepting input of image data indicating said biochemical information or symbolic data indicating said biochemical information, reaction scheme detection means for, when said input means accepts data about a compound being a substrate and/or a product, detecting a chemical reaction scheme involving said compound, based on the data, and display means for indicating at least a reaction scheme diagram of the chemical reaction scheme;

wherein said storage means comprises a compound information file storing a list showing the relation between compound numbers of the compounds and canonical data corresponding to said compounds, and additional information about said compounds, an enzyme information file storing a list showing the relation among enzyme numbers of the enzymes, compound numbers of compounds being substrates for said enzymes, and compound numbers of compounds being products by said enzymes, and additional information about said enzymes, and a relation (correlation) information file storing a list showing the relation among compound numbers of compounds as a key, enzyme numbers of enzymes with either said compound being a substrate, and enzyme numbers of enzymes with either said compound being a product; and wherein said reaction scheme detection means comprises a first process portion for preparing from the data about a compound accepted through said input means said canonical data uniquely indicating a chemical structure of said compound, further searching said compound information file, based on the canonical data, and thereby reading out a compound number corresponding to said canonical data when said canonical data exists in said compound information file, a second process portion for reading an enzyme number of an enzyme with the compound being a substrate or a product out of said relation information file, based on the compound number read out in said first process portion, a third process portion for reading a compound number of another compound constituting a reaction system together with the enzyme of the enzyme number read out in said second process portion and said compound, and additional information about said enzyme out of said enzyme information file, and a fourth process portion for indicating a reaction scheme diagram of the compound accepted through said input means on said display means from the compound number read out in said first process portion, the enzyme number read out in said second process portion, and the compound number of the another compound read out in said third process portion, and further indicating the additional information about the enzyme read out in said third process portion on said display means.

With the above biochemical information processing apparatus of the present invention, when the data about the compound accepted through the input means is supplied to the first process portion, the canonical data is prepared from this data. Then the compound information file is searched based on the canonical data thus prepared, and if the canonical data exists in the compound information file, a compound number corresponding to the canonical data is read out thereof. The compound number read out in the first process portion is supplied to the second process portion, and the second process portion reads an enzyme number of an enzyme with this compound being a substrate or a compound out of the relation information file.

The enzyme number read out in the second process portion is supplied to the third process portion, and the third process portion reads a compound number of another compound constituting a reaction system together with the enzyme and the foregoing compound, and additional information about the enzyme out of the enzyme information file. Then the compound number read out in the first process portion, the enzyme number read out in the second process portion, and the compound number of the another compound read out in the third process portion are supplied to the fourth process portion, and the fourth process portion lets the display means indicate a reaction scheme diagram of the compound accepted through the input means. Similarly, the additional information about the enzyme read out in the third process portion is also indicated on the display means.

The biochemical information processing apparatus of the present invention may further comprise receptor information detection means for, when said input means accepts data about a compound, detecting additional information about a receptor with said compound being an agonist and/or an antagonist, based on the data, and in this case;

said storage means further stores biochemical information about receptors, and further comprises a receptor information file storing a list showing the relation between receptor numbers of the receptors and compound numbers of compounds being agonists and/or antagonists for said receptors, and additional information about said receptors;

said relation information file stores a list to show the relation among the compound numbers of the compounds as a key, the enzyme numbers of the enzymes with either said compound being a substrate, the enzyme numbers of the enzymes with either said compound being a product, the receptor numbers of the receptors with either said compound being an agonist, and the receptor numbers of the receptors with either said compound being an antagonist; and said receptor information detection means comprises a fifth process portion for preparing from data about a compound accepted through said input means said canonical data uniquely indicating a chemical structure of said compound, further searching said compound information file, based on said canonical data, and thereby reading out a compound number corresponding to said canonical data when said canonical data exists in said compound information file, a sixth process portion for reading, based on the compound number read out in said fifth process portion, a receptor number of a receptor with the compound being an agonist or an antagonist out of said relation information file, a seventh process portion for reading at least additional information about the receptor of the receptor number read out in said sixth process portion out of said receptor information file, and an eighth process portion for indicating at least the additional information about the receptor read out in said seventh process portion on said display means.

In this case, in the biochemical information processing apparatus of the present invention, when the data about the compound accepted through the input means is supplied to the fifth process portion, canonical data is prepared from this data. Then the compound information file is searched based on the canonical data thus prepared, and if the canonical data exists in the compound information file, a compound number corresponding to the canonical data is read out thereof. The compound number read out in the fifth process portion is supplied to the sixth process portion, and the sixth process portion reads a receptor number of a receptor with this compound being an agonist or an antagonist out of the relation information file. The receptor number read out in the sixth process portion is supplied to the seventh process portion, and the seventh process portion reads at least the additional information about the receptor out of the receptor information file. Then at least the additional information about the receptor read out in the seventh process portion is supplied to the eighth process portion, and the eighth process portion lets the display means indicate at least the additional information about the receptor.

Also, the biochemical information processing apparatus of the present invention may further comprise reaction path detection means for, when said input means accepts data about a predetermined compound selected from a plurality of compounds constituting a reaction path, detecting the reaction path of said plurality of compounds, based on the data, and in this case;

said reaction path detection means comprises a ninth process portion for preparing from the data about the compound accepted through said input means said canonical data uniquely indicating a chemical structure of said compound, further searching said compound information file, based on the canonical data, and thereby reading out a compound number corresponding to said canonical data when said canonical data exists in said compound information file, a tenth process portion for reading, based on the compound number read out in said ninth process portion, an enzyme number of an enzyme with the compound being a substrate and an enzyme number of an enzyme with the compound being a product out of said relation information file, an eleventh process portion for reading, based on each enzyme number read out in said tenth process portion, a compound number of a compound being a substrate for said enzyme and a compound number of a compound being a product by said enzyme out of said enzyme information file, a twelfth process portion for repeating a process by said tenth process portion and a process by said eleventh process portion to obtain compounds and enzymes within the predetermined reaction path, and a thirteenth process portion for indicating from enzyme numbers read out in said tenth process portion and compound numbers read out in said eleventh process portion a reaction scheme diagram of these compounds along the reaction path on said display means.

In this case, in the biochemical information processing apparatus of the present invention, when the data about the compound accepted through the input means is supplied to the ninth process portion, canonical data is prepared from this data. Then the compound information file is searched based on the canonical data thus prepared, and if the canonical data exists in the compound information file, a compound number corresponding to the canonical data is read out thereof. The compound number read out in the ninth process portion is supplied to the tenth process portion, and the tenth process portion reads an enzyme number of an enzyme with the compound being a substrate and an enzyme number of an enzyme with the compound being a product out of the relation information file.

Each enzyme number read out in the tenth process portion is supplied to the eleventh process portion, and the eleventh process portion reads a compound number of a compound being a substrate for the enzyme and a compound number of a compound being a product by the enzyme out of the enzyme information file. The processes of the tenth process portion and the eleventh process portion are repeated in the twelfth process portion.

Then the enzyme numbers read out in the tenth process portion and the compound numbers read out in the eleventh process portion are supplied to the thirteenth process portion, and the thirteenth process portion lets the display means indicate a reaction scheme diagram of these compounds along a predetermined reaction path.

Further, the biochemical information processing apparatus of the present invention may be the following one. Namely, the apparatus is a biochemical information processing apparatus comprising storage means for storing biochemical information about compounds and enzymes, input means for accepting input of image data indicating said biochemical information or symbolic data indicating said biochemical information, reaction path detection means for, when said input means accepts data about a predetermined compound selected from a plurality of compounds constituting a reaction path, detecting the reaction path of said plurality of compounds, based on the data, and display means for indicating at least a reaction scheme diagram of the chemical reaction scheme;

wherein said storage means comprises a compound information file storing a list showing the relation between compound numbers of the compounds and canonical data corresponding to said compounds, and additional information about said compounds, an enzyme information file storing a list showing the relation among enzyme numbers of the enzymes, compound numbers of compounds being substrates for said enzymes, and compound numbers of compounds being products by said enzymes, and additional information about said enzymes, and a relation (correlation) information file storing a list showing the relation among compound numbers of compounds as a key, enzyme numbers of enzymes with either said compound being a substrate, and enzyme numbers of enzymes with either said compound being a product; and wherein said reaction path detection means comprises a ninth process portion for preparing from the data about the compound accepted through said input means said canonical data uniquely indicating a chemical structure of said compound, further searching said compound information file, based on the canonical data, and thereby reading out a compound number corresponding to said canonical data when said canonical data exists in said compound information file, a tenth process portion for reading, based on the compound number read out in said ninth process portion, an enzyme number of an enzyme with the compound being a substrate and an enzyme number of an enzyme with the compound being a product out of said relation information file, an eleventh process portion for reading, based on each enzyme number read out in said tenth process portion, a compound number of a compound being a substrate for said enzyme and a compound number of a compound being a product by said enzyme out of said enzyme information file, a twelfth process portion for repeating a process by said tenth process portion and a process by said eleventh process portion to obtain compounds and enzymes within the predetermined reaction path, and a thirteenth process portion for indicating from the enzyme numbers read out in said tenth process portion and compound numbers read out in said eleventh process portion a reaction scheme diagram of these compounds along the reaction path on said display means.

In this case, the biochemical information processing apparatus of the present invention may further comprise receptor information detection means for, when said input means accepts data about a compound, detecting additional information about a receptor with said compound being an agonist and/or an antagonist, based on the data, and in this case;

said storage means further stores biochemical information about receptors, and further comprises a receptor information file storing a list showing the relation between receptor numbers of the receptors and compound numbers of compounds being agonists and/or antagonists for said receptors, and additional information about said receptors;

said relation information file stores a List to show the relation among the compound numbers of the compounds as a key, the enzyme numbers of the enzymes with either said compound being a substrate, the enzyme numbers of the enzymes with either said compound being a product, the receptor numbers of the receptors with either said compound being an agonist, and the receptor numbers of the receptors with either said compound being an antagonist; and said receptor information detection means comprises a fifth process portion for preparing from data about a compound accepted through said input means said canonical data uniquely indicating a chemical structure of said compound, further searching said compound information file, based on said canonical data, and thereby reading out a compound number corresponding to said canonical data when said canonical data exists in said compound information file, a sixth process portion for reading, based on the compound number read out in said fifth process portion, a receptor number of a receptor with the compound being an agonist or an antagonist out of said relation information file, a seventh process portion for reading at least additional information about the receptor of the receptor number read out in said sixth process portion out of said receptor information file, and an eighth process portion for indicating at least the additional information about the receptor read out in said seventh process portion on said display means.

Further, in the biochemical information processing apparatus of the present invention, preferably, said input means accepts input of characteristic data about each of atoms constituting a compound and bonding pair data between atoms; and said biochemical information processing apparatus preferably further comprises the following canonical data preparation means for preparing canonical data capable of uniquely specifying a chemical structure of said compound, based on each data accepted through said input means. Namely, said canonical data preparation means comprises a constituent atom classification process portion for classifying, based on each data accepted through said input means, the atoms into different classes each for equivalent atoms and assigning, to each atom, a different class number for each class, a canonical number assignment process portion for assigning canonical numbers uniquely corresponding to the structure of said compound to the respective atoms, based on the class numbers assigned to the respective atoms in said constituent atom classification process portion, and a canonical data preparation process portion for preparing said canonical data, based on the canonical numbers assigned to the respective atoms in said canonical number assignment process portion.

With the canonical data preparation means according to the present invention having the above structure, the characteristic data about each atom and bonding pair data between atoms accepted through the input means is supplied to the canonical data preparation means. Then the canonical data preparation means prepares the canonical data, based on these data.

Namely, the canonical data preparation means first carries out the process of constituent atom classification process portion to classify the atoms into different classes each for equivalent atoms, based on the characteristic data about each atom and the bonding pair data between atoms. Then class numbers of respective classes different from each other are assigned to the respective atoms. Next, the process of canonical number assignment process portion is carried out to assign canonical numbers uniquely corresponding to the structure of the compound to the respective atoms, based on the class numbers assigned to the respective atoms and the bonding pair data between atoms. Further, the process of canonical data preparation process portion is carried out to prepare the canonical data based on the canonical numbers assigned to the respective atoms and the characteristic data about the respective atoms.

Here, preferably, said constituent atom classification process portion assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path;

said canonical number assignment process portion is arranged so that when in a process for assigning a canonical number to each atom in the ascending order from 1 the canonical number 1 is given to an atom with a highest priority of said class number and thereafter canonical numbers up to the canonical number n are assigned in that manner, said canonical number assignment process portion selects an atom with a minimum canonical number out of atoms already having their respective canonical numbers and bonding to an atom having no canonical number yet and then gives a canonical number n+1 to an atom with a highest priority of said class number out of atoms bonding to said selected atom and having no canonical number yet; and said canonical data preparation process portion gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

Next explained is the biochemical information processing method of the present invention.

The biochemical information processing method of the present invention is a biochemical information processing method using an information processing apparatus comprising storage means for storing biochemical information about compounds and enzymes, input means for accepting input of image data indicating said biochemical information or symbolic data indicating said biochemical information, and display means for indicating at least a reaction scheme diagram of a chemical reaction scheme;

wherein said storage means comprises a compound information file storing a list showing the relation between compound numbers of the compounds and canonical data corresponding to said compounds, and additional information about said compounds, an enzyme information file storing a list showing the relation among enzyme numbers of the enzymes, compound numbers of compounds being substrates for said enzymes, and compound numbers of compounds being products by said enzymes, and additional information about said enzymes, and a relation (correlation) information file storing a list showing the relation among compound numbers of compounds as a key, enzyme numbers of enzymes with either said compound being a substrate, and enzyme numbers of enzymes with either said compound being a product; and wherein said biochemical information processing method comprises a first step for, when said input means accepts data about a compound being a substrate and/or a product, preparing said canonical data uniquely indicating a chemical structure of said compound from the data, further searching said compound information file, based on the canonical data, and thereby reading out a compound number corresponding to said canonical data when said canonical data exists in said compound information file, a second step for reading an enzyme number of an enzyme with the compound being a substrate or a product out of said relation information file, based on the compound number read out in said first step, a third step for reading a compound number of another compound constituting a reaction system together with the enzyme of the enzyme number read out in said second step and said compound, and additional information about said enzyme out of said enzyme information file, and a fourth step for indicating a reaction scheme diagram of the compound accepted through said input means on said display means from the compound number read out in said first step, the enzyme number read out in said second step, and the compound number of the another compound read out in said third step, and further indicating the additional information about the enzyme read out in said third step on said display means.

With the above biochemical information processing method of the present invention, the processes of the first step to the fourth step enable to detect a reaction scheme. In the detection of reaction scheme, first, the process of the first step is carried out to prepare canonical data from the data about the compound accepted through the input means. Then the compound information file is searched based on the canonical data thus prepared, and if the canonical data exists in the compound information file, a compound number corresponding to the canonical data is read out thereof. Next, the process of the second step is carried out to read out an enzyme number of an enzyme with the compound being a substrate or a product out of the relation information file, based on the compound number read out in the first step.

Further, the process of the third step is carried out to read a compound number of another compound constituting a reaction system together with the enzyme of the enzyme number read out in the second step and the compound, and the additional information about the enzyme out of the enzyme information file. Then the process of the fourth step is carried out to indicate the reaction scheme diagram of the compound accepted through the input means on the display means from the compound number read out in the first step, the enzyme number read out in the second step, and the compound number of the another compound read out in the third step. Similarly, the additional information about the enzyme read out in the third step is also indicated on the display means.

In the biochemical information processing method of the present invention, said storage means may further store biochemical information about a receptor, and may further comprise a receptor information file storing a list showing the relation between receptor numbers of the receptors and compound numbers of compounds being agonists and/or antagonists for said receptors, and additional information about said receptors, and in this case;

said relation information file stores a list to show the relation among the compound numbers of the compounds as a key, the enzyme numbers of the enzymes with either said compound being a substrate, the enzyme numbers of the enzymes with either said compound being a product, the receptor numbers of the receptors with either said compound being an agonist, and the receptor numbers of the receptors with either said compound being an antagonist; and said biochemical information processing method further comprises a fifth step for, when said input means accepts data about a compound, preparing said canonical data uniquely indicating a chemical structure of said compound from the data, further searching said compound information file, based on said canonical data, and thereby reading out a compound number corresponding to said canonical data when said canonical data exists in said compound information file, a sixth step for reading, based on the compound number read out in said fifth step, a receptor number of a receptor with the compound being an agonist or an antagonist out of said relation information file, a seventh step for reading at least additional information about the receptor of the receptor number read out in said sixth step out of said receptor information file, and an eighth step for indicating at least the additional information about the receptor read out in said seventh step on said display means.

In this case, in the biochemical information processing method of the present invention, the processes of the fifth step to the eighth step enable to detect receptor information. In the detection of receptor information, first, the process of the fifth step is carried out to prepare canonical data from the data about the compound accepted through the input means. Then the compound information file is searched based on the canonical data prepared, and if the canonical data exists in the compound information file, a compound number corresponding to the canonical data is read out thereof. Next, the process of the sixth step is carried out to read a receptor number of a receptor with the compound being an agonist or an antagonist, based on the compound number react out in the fifth step, out of the relation information file. Further, the process of the seventh step is carried out to read at least the additional information about the receptor of the receptor number read out in the sixth step out of the receptor information file. Then the process of the eighth step is carried out to display at least the additional information about the receptor read out in the seventh step on the display means.

The biochemical information processing method of the present invention may further comprise a ninth step for, when said input means accepts data about a predetermined compound selected from a plurality of compounds constituting a reaction path, preparing said canonical data uniquely indicating a chemical structure of said compound from the data, further searching said compound information file, based on the canonical data, and thereby reading out a compound number corresponding to said canonical data when said canonical data exists in said compound information file, a tenth step for reading, based on the compound number read out in said ninth step, an enzyme number of an enzyme with the compound being a substrate and an enzyme number of an enzyme with the compound being a product out of said relation information file, an eleventh step for reading, based on each enzyme number read out in said tenth step, a compound number of a compound being a substrate for said enzyme and a compound number of a compound being a product by said enzyme out of said enzyme information file, a twelfth step for repeating a process by said tenth step and a process by said eleventh step to obtain compounds and enzymes within the predetermined reaction path, and a thirteenth step for indicating from the enzyme numbers read out in said tenth step and compound numbers read out in said eleventh step a reaction scheme diagram of these compounds along the reaction path on said display means.

In this case, in the biochemical information processing method of the present invention, the processes of the ninth step to the twelfth step enable to detect a reaction path. In the detection of reaction path, first, the process of the ninth step is carried out to prepare canonical data from the data about the predetermined compound accepted through the input means. Then the chemical information file is searched based on the canonical data thus prepared, and if the canonical data exists in the compound information file, a compound number corresponding to the canonical data is read out thereof. Next, the process of the tenth step is carried out to read an enzyme number of an enzyme with this compound being a substrate and an enzyme number of an enzyme with this compound being a product, based on the compound number read out in the ninth step, out of the relation information file. Further, the process of the eleventh step is carried out to read, based on each enzyme number read out in the tenth step, a compound number of a compound with this enzyme being a substrate and a compound number of a compound with this enzyme being a product out of the enzyme information file. The processes of the tenth step and the eleventh step are repeated in the twelfth step.

Then the process of the thirteenth step is carried out to indicate from the enzyme numbers read out in the tenth step and the compound numbers read out in the eleventh step the reaction scheme diagram of these compounds along a reaction path on the display means.

Further, the biochemical information processing method of the present invention may be the following one. Namely, the method may be a biochemical information processing method using an information processing apparatus comprising storage means for storing biochemical information about compounds and enzymes, input means for accepting input of image data indicating said biochemical information or symbolic data indicating said biochemical information, and display means for indicating at least a reaction scheme diagram of a chemical reaction scheme;

wherein said storage means comprises a compound information file storing a list showing the relation between compound numbers of the compounds and canonical data corresponding to said compounds, and additional information about said compounds, an enzyme information file storing a list showing the relation among enzyme numbers of the enzymes, compound numbers of compounds being substrates for said enzymes, and compound numbers of compounds being products by said enzymes, and additional information about said enzymes, and a relation (correlation) information file storing a list showing the relation among compound numbers of compounds as a key, enzyme numbers of enzymes with either said compound being a substrate, and enzyme numbers of enzymes with either said compound being a product; and wherein said biochemical information processing method comprises a ninth step for, when said input means accepts data about a predetermined compound selected from a plurality of compounds constituting a reaction path, preparing said canonical data uniquely indicating a chemical structure of said compound from the data, further searching said compound information file, based on the canonical data, and thereby reading out a compound number corresponding to said canonical data when said canonical data exists in said compound information file, a tenth step for reading, based on the compound number read out in said ninth step, an enzyme number of an enzyme with the compound being a substrate and an enzyme number of an enzyme with the compound being a product out of said relation information file, an eleventh step for reading, based on each enzyme number read out in said tenth step, a compound number of a compound being a substrate for said enzyme and a compound number of a compound being a product by said enzyme out of said enzyme information file, a twelfth step for repeating a process by said tenth step and a process by said eleventh step to obtain compounds and enzymes within the predetermined reaction path, and a thirteenth step for indicating from enzyme numbers read out in said tenth step and compound numbers read out in said eleventh step a reaction scheme diagram of these compounds along the reaction path on said display means.

In this case, in the biochemical information processing method of the present invention, said storage means may further store biochemical information about receptors, and may further comprise a receptor information file storing a list showing the relation between receptor numbers of the receptors and compound numbers of compounds being agonists and/or antagonists for said receptors, and additional information about said receptors, and in this case;

said relation information file stores a list to show the relation among the compound numbers of the compounds as a key, the enzyme numbers of the enzymes with either said compound being a substrate, the enzyme numbers of the enzymes with either said compound being a product, the receptor numbers of the receptors with either said compound being an agonist, and the receptor numbers of the receptors with either said compound being an antagonist; and said biochemical information processing method further comprises a fifth step for, when said input means accepts data about a compound, preparing said canonical data uniquely indicating a chemical structure of said compound from the data, further searching said compound information file, based on said canonical data, and thereby reading out a compound number corresponding to said canonical data when said canonical data exists in said compound information file, a sixth step for reading, based on the compound number read out in said fifth step, a receptor number of a receptor with the compound being an agonist or an antagonist out of said relation information file, a seventh step for reading at least additional information about the receptor of the receptor number read out in said sixth step out of said receptor information file, and an eighth step for indicating at least the additional information about the receptor read out in said seventh step on said display means.

Further, in the biochemical information processing method of the present invention, preferably, said input means accepts input of characteristic data about each of atoms constituting a compound and bonding pair data between atoms; and said biochemical information processing method further comprises a constituent atom classification step for classifying, based on each data accepted through said input means, the atoms into different classes each for equivalent atoms and assigning, to each atom, a different class number for each class, a canonical number assignment step for assigning canonical numbers uniquely corresponding to the structure of said compound to the respective atoms, based on the class numbers assigned to the respective atoms in said constituent atom classification step, and a canonical data preparation step for preparing said canonical data enabling to uniquely specify a chemical structure of said compound, based on the canonical numbers assigned to the respective atoms in said canonical number assignment step.

By the various steps for preparing the canonical data according to the present invention having such structure, the canonical data is prepared based on the characteristic data about each atom and the bonding pair data between atoms accepted through the input means.

Namely, first, in the constituent atom classification step, the atoms are classified into different classes each for equivalent atoms, based on the characteristic data about each atom and the bonding pair data between atoms. Then a different class number for each class is assigned to each atom. Next, in the canonical number assignment step, the canonical numbers uniquely corresponding to the structure of the compound are assigned to the respective atoms, based on the class numbers given to the respective atoms and the bonding pair data between atoms. Further, in the canonical data preparation step, the canonical data is prepared based on the canonical numbers given to the respective atoms and the characteristic data about each atom.

Here, preferably, said constituent atom classification step assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path;

said canonical number assignment step is arranged so that when in a process for assigning a canonical number to each atom in the ascending order from 1 the canonical number 1 is given to an atom with a highest priority of said class number and thereafter canonical numbers up to the canonical number n are assigned in that manner, said canonical number assignment step selects an atom with a minimum canonical number out of atoms already having their respective canonical numbers and bonding to an atom having no canonical number yet and then gives a canonical number n+1 to an atom with a highest priority of said class number out of atoms bonding to said selected atom and having no canonical number yet; and said canonical data preparation step gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

Next explained is the biochemical information computer program product (biochemical information recording medium) of the present invention.

The biochemical information computer program product of the present invention is a biochemical information computer program product used with an information processing apparatus comprising input means for accepting input of image data indicating biochemical information or symbolic data indicating biochemical information, display means for indicating at least a reaction scheme diagram of a chemical reaction scheme, and reading means for reading information out of a computer-usable medium;

said computer program product comprising the computer-usable medium having a file area for recording a file and a program area for recording a program and having computer-readable file and program embodied in said medium, for letting at least a reaction scheme diagram efficiently be searched for and be indicated by said display means, based on data input through said input means;

said computer program product having, in said file area, a computer-readable compound information file for storing a list showing the relation between compound numbers of compounds and canonical data corresponding to said compounds, and additional information about said compounds, a computer-readable enzyme information file for storing a list showing the relation among enzyme numbers of enzymes, compound numbers of compounds being substrates for said enzymes, and compound numbers of compounds being products by said enzymes, and additional information about said enzymes, and a computer-readable relation (correlation) information file for storing a list showing the relation among the compound numbers of the compounds as a key, enzyme numbers of enzymes with either said compound being a substrate, and enzyme numbers of enzymes with either said compound being a product, and having, in said program area, a computer-readable reaction scheme detection program for, when said input means accepts data about a compound being a substrate and/or a product, detecting a chemical reaction scheme involving said compound, based on the data;

wherein said reaction scheme detection program comprises a first computer-readable process routine for preparing from the data about a compound accepted through said input means said canonical data uniquely indicating a chemical structure of said compound, further searching said compound information file, based on the canonical data, and thereby reading out a compound number corresponding to said canonical data when said canonical data exists in said compound information file, a second computer-readable process routine for reading an enzyme number of an enzyme with the compound being a substrate or a product out of said relation information file, based on the compound number read out in said first process routine, a third computer-readable process routine for reading a compound number of another compound constituting a reaction system together with the enzyme of the enzyme number read out in said second process routine and said compound, and additional information about said enzyme out of said enzyme information file, and a fourth computer-readable process routine for indicating a reaction scheme diagram of the compound accepted through said input means on said display means from the compound number read out in said first process routine, the enzyme number read out in said second process routine, and the compound number of the another compound read out in said third process routine, and further indicating the additional information about the enzyme read out in said third process routine on said display means.

In the above biochemical information computer program product of the present invention, the compound information file etc. are recorded in the file area and the reaction scheme detection program is recorded in the program area.

The reaction scheme detection program can be executed using the information processing apparatus. By this execution, first, the process of the first process routine is carried out to prepare the canonical data from the data about the compound accepted through the input means. Then the compound information file is searched based on the canonical data thus prepared, and if the canonical data exists in the compound information file, a compound number corresponding to the canonical data is read out thereof.

Next, the process of the second process routine is carried out to read an enzyme number of an enzyme with this compound being a substrate or a product, based on the compound number read out in the first process routine, out of the relation information file. Further, the process of the third process routine is carried out to read a compound number of another compound constituting a reaction system together with the enzyme of the enzyme number read out in the second process routine and the compound, and the additional information about the enzyme out of the enzyme information file. Then the process of the fourth process routine is carried out to indicate the reaction scheme diagram of the compound accepted through the input means on the display means from the compound number read out in the first process routine, the enzyme number read out in the second process routine, and the compound number of the another compound read out in the third process routine. Further, the additional information about the enzyme read out in the third process routine is also indicated on the display means.

The biochemical information computer program product of the present invention may further have, in said file area, a computer-readable receptor information file storing a list showing the relation between receptor numbers of the receptors and compound numbers of compounds being agonists and/or antagonists for said receptors, and additional information about said receptors;

said relation information file stores a list to show the relation among the compound numbers of the compounds as a key, the enzyme numbers of the enzymes with either said compound being a substrate, the enzyme numbers of the enzymes with either said compound being a product, the receptor numbers of the receptors with either said compound being an agonist, and the receptor numbers of the receptors with either said compound being an antagonist; and said computer program product further has, in said program area, a computer-readable receptor information detection program for, when said input means accepts data about a compound, detecting additional information about a receptor with said compound being an agonist and/or an antagonist, based on the data; and said receptor information detection program comprises a fifth computer-readable process routine for preparing from data about a compound accepted through said input means said canonical data uniquely indicating a chemical structure of said compound, further searching said compound information file, based on said canonical data, and thereby reading out a compound number corresponding to said canonical data when said canonical data exists in said compound information file, a sixth computer-readable process routine for reading, based on the compound number read cut in said fifth process routine, a receptor number of a receptor with the compound being an agonist or an antagonist out of said relation information file, a seventh computer-readable process routine for reading at least additional information about the receptor of the receptor number read out in said sixth process routine out of said receptor information file, and an eighth computer-readable process routine for indicating at least the additional information about the receptor read out in said seventh process routine on said display means.

In this case, in the above biochemical information computer program product of the present invention, the receptor information detection program is recorded in addition to the reaction scheme detection program in the program area.

The receptor information detection program can be executed using the information processing apparatus.

By this execution, first, the process of the fifth process routine is carried out to prepare the canonical data from the data about the compound accepted through the input means. Then the compound information file is searched based on the canonical data thus prepared, and if the canonical data exists in the compound information file, a compound number corresponding to the canonical data is read out thereof.

Next, the process of the sixth process routine is carried out to read a receptor number of a receptor with this compound being an agonist or an antagonist, based on the compound number read out in the fifth process routine, out of the relation information file. Further, the process of the seventh process routine is carried out to read at least the additional information about the receptor of the receptor number read out in the sixth process routine out of the receptor information file. Then the process of the eighth process routine is carried out to indicate at least the additional information about the receptor read out in the seventh process routine on the display means.

The biochemical information computer program product of the present invention may further have, in said program area, a computer-readable reaction path detection program for, when said input means accepts data about a predetermined compound selected from a plurality of compounds constituting a reaction path, detecting the reaction path of said plurality of compounds, based on the data, and in this case;

said reaction path detection program comprises a ninth computer-readable process routine for preparing from the data about the compound accepted through said input means said canonical data uniquely indicating a chemical structure of said compound, further searching said compound information file, based on the canonical data, and thereby reading cut a compound number corresponding to said canonical data when said canonical data exists in said compound information file, a tenth computer-readable process routine for reading, based on the compound number read cut in said ninth process routine, an enzyme number of an enzyme with the compound being a substrate and an enzyme number of an enzyme with the compound being a product out of said relation information file, an eleventh computer-readable process routine for reading, based on each enzyme number read out in said tenth process routine, a compound number of a compound being a substrate for said enzyme and a compound number of a compound being a product by said enzyme out of said enzyme information file, a twelfth computer-readable process routine for repeating a process by said tenth process routine and a process by said eleventh process routine to obtain compounds and enzymes within the predetermined reaction path, and a thirteenth computer-readable process routine for indicating from enzymes numbers read out in said tenth process routine and compound numbers read out in said eleventh process routine a reaction scheme diagram of these compounds along the reaction path on said display means.

In this case, in the above biochemical information computer program product of the present invention, the reaction path detection program is recorded in addition to the reaction scheme detection program and the receptor information detection program in the program area.

The reaction path detection program can be executed using the information processing apparatus.

By this execution, first, the process of the ninth process routine is carried out to prepare the canonical data from the data about the predetermined compound accepted through the input means. Then the compound information file is searched based on the canonical data thus prepared, and if the canonical data exists in the compound information file, a compound number corresponding to the canonical data is read out thereof.

Next, the process of the tenth process routine is carried out to read an enzyme number of an enzyme with the compound being a substrate and an enzyme number of an enzyme with the compound being a product, based on the compound number read out in the ninth process routine, out of the relation information file. Further, the process of the eleventh process routine is carried out to read, based on each enzyme number read out in the tenth process routine, a compound number of a compound being a substrate of the enzyme and a compound number of a compound being a product of the enzyme out of the enzyme information file. The processes of the tenth process routine and the eleventh process routine are repeated in the twelfth process routine.

Then the process of the thirteenth process routine is carried out to indicate a reaction scheme diagram of these compounds along a reaction path on the display means from the enzyme numbers read out in the tenth process routine and the compound numbers read out in the eleventh process routine.

Further, the biochemical information computer program product of the present invention may be the following one. Namely, the product may be a biochemical information computer program product used with an information processing apparatus comprising input means for accepting input of image data indicating biochemical information or symbolic data indicating biochemical information, display means for indicating at least a reaction scheme diagram of a chemical reaction scheme, and reading means for reading information out of a computer-usable medium;

said computer program product comprising the computer-usable medium having a file area for recording a file and a program area for recording a program and having computer-readable file and program embodied in said medium, for letting at least a reaction scheme diagram efficiently be searched for and be indicated by said display means, based on data input through said input means;

said computer program product having, in said file area, a computer-readable compound information file for storing a list showing the relation between compound numbers of compounds and canonical data corresponding to said compounds, and additional information about said compounds, a computer-readable enzyme information file for storing a list showing the relation among enzyme numbers of enzymes, compound numbers of compounds being substrates for said enzymes, and compound numbers of compounds being products by said enzymes, and additional information about said enzymes, and a computer-readable relation (correlation) information file for storing a list showing the relation among the compound numbers of the compounds as a key, enzyme numbers of enzymes with either said compound being a substrate, and enzyme numbers of enzymes with either said compound being a product, and having, in said program area, a computer-readable reaction path detection program for, when said input means accepts data about a predetermined compound selected from a plurality of compounds constituting a reaction path, detecting the reaction path of said plurality of compounds, based on the data;

wherein said reaction path detection program comprises a ninth computer-readable process routine for preparing from the data about the compound accepted through said input means said canonical data uniquely indicating a chemical structure of said compound, further searching said compound information file, based on the canonical data, and thereby reading out a compound number corresponding to said canonical data when said canonical data exists in said compound information file, a tenth computer-readable process routine for reading, based on the compound number read out in said ninth process routine, an enzyme number of an enzyme with the compound being a substrate and an enzyme number of an enzyme with the compound being a product out of said relation information file, an eleventh computer-readable process routine for reading, based on each enzyme number read out in said tenth process routine, a compound number of a compound being a substrate for said enzyme and a compound number of a compound being a product by said enzyme out of said enzyme information file, a twelfth computer-readable process routine for repeating a process by said tenth process routine and a process by said eleventh process routine to obtain compounds and enzymes within the predetermined reaction path, and a thirteenth computer-readable process routine for indicating from enzyme numbers read out in said tenth process routine and compound numbers read out in said eleventh process routine a reaction scheme diagram of these compounds along the reaction path on said display means.

In this case, the biochemical information computer program product of the present invention may further have, in said file area, a computer-readable receptor information file storing a list showing the relation between a receptor number of a receptor and a compound number of a compound being an agonist and/or an antagonist of said receptor, and additional information about said receptor, and in this case;

said relation information file stores a list to show the relation among a compound number of a compound as a key, an enzyme number of an enzyme with said compound being a substrate, an enzyme number of an enzyme with said compound being a product, a receptor number of a receptor with said compound being an agonist, and a receptor number of a receptor with said compound being an antagonist; and said computer program product further has, in said program area, a computer-readable receptor information detection program for, when said input means accepts data about a compound, detecting additional information about a receptor with said compound being an agonist and/or an antagonist, based on the data; and said receptor information detection program comprises a fifth computer-readable process routine for preparing from data about a compound accepted through said input means said canonical data uniquely indicating a chemical structure of said compound, searching said compound information file, based on this canonical data, and reading out a compound number corresponding to said canonical data when said canonical data exists in said compound information file, a sixth computer-readable process routine for reading, based on the compound number read out in said fifth process routine, a receptor number of a receptor with the compound being an agonist or an antagonist out of said relation information file, a seventh computer-readable process routine for reading at least additional information about a receptor of the receptor number read out in said sixth process routine out of said receptor information file, and an eighth computer-readable process routine for indicating at least the additional information about the receptor read out in said seventh process routine on said display means.

Further, in the biochemical information computer program product of the present invention, preferably, said input means accepts input of characteristic data about each of atoms constituting a compound and bonding pair data between atoms; and said computer program product further has, in said program area, a computer-readable canonical data preparation program for preparing canonical data capable of uniquely specifying a chemical structure of said compound, based on each data accepted through said input means. Namely, said canonical data preparation program comprises a computer-readable constituent atom classification routine for classifying the atoms into different classes each for equivalent atoms and assigning, to each atom, a different class number for each class, a computer-readable canonical number assignment routine for assigning canonical numbers uniquely corresponding to the structure of said compound to the respective atoms, based on the class numbers assigned to the respective atoms in said constituent atom classification routine, and a computer-readable canonical data preparation routine for preparing said canonical data, based on the canonical numbers assigned to the respective atoms in said canonical number assignment routine.

By setting the biochemical information computer program product according to the present invention having such structure in a predetermined information processing apparatus and reading the canonical data preparation program stored in the program area, the canonical data preparation program can be executed by the information processing apparatus. By start of the canonical data preparation program, the constituent atom classification routine is first carried out to classify the atoms into different classes each for equivalent atoms, based on the characteristic data about each atom and the bonding pair data between atoms. Then a different class number for each class is assigned to each atom. Then the canonical number assignment routine is carried out to assign canonical numbers uniquely corresponding to the structure of the compound to the respective atoms, based on the class numbers given to the respective atoms and the bonding pair data between atoms. Further, the canonical data preparation routine is carried out to prepare the canonical data based on the canonical numbers given to the respective atoms and the characteristic data about each atom.

Here, preferably, said constituent atom classification routine assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path;

said canonical number assignment routine is arranged so that when in a process for assigning a canonical number to each atom in the ascending order from 1 the canonical number 1 is given to an atom with a highest priority of said class number and thereafter canonical numbers up to the canonical number n are assigned in that manner, said canonical number assignment routine selects an atom with a minimum canonical number out of atoms already having their respective canonical numbers and bonding to an atom having no canonical number yet and then gives a canonical number n+1 to an atom with a highest priority of said class number out of atoms bonding to said selected atom and having no canonical number yet; and said canonical data preparation routine gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

The computer-usable medium according to the present invention is preferably a disk type recording medium or a tape type recording medium.

BRIEF DESCRIPTION OF DRAWINGS

FIG. 3 is a drawing to show the structure of a compound information file.

FIG. 4 is a drawing to show the structure of an enzyme information file.

FIG. 6 is a drawing to show the structure of an example of the relation information file according to the present invention.

FIGS. 10A–10C are drawings to show the relationship between image data and canonical data.

FIG. 16 is a drawing to show an example of indication on a display.

FIG. 17 is a drawing to show another example of indication on the display.

FIG. 18A is a drawing to show the contents of an atomic table in the bond table, and FIG. 18B is a drawing to show the contents of an atomic pair table in the bond table.

FIG. 22A is a drawing to show the contents of an atomic table in the bond table, and FIG. 22B is a drawing to show the contents of an atomic pair table in the bond table.

FIG. 25 is a drawing to show three types of attributes ($a_i$, $b_{ij}$, $d_{ij}$) given to each of the atoms constituting 3,5-dimethyl-2,3,4,5-tetrahydropyridine.

FIG. 31 is a drawing to show attributes $V_{ij}^1$ given to the respective atoms constituting 3,5-dimethyl-2,3,4,5-tetrahydropyridine.

FIG. 32 is a drawing to show attributes $V_{ij}^2$ given to the respective atoms constituting 3,5-dimethyl-2,3,4,5-tetrahydropyridine.

FIG. 36A is a drawing to show the contents of an atomic table in the bond table, and FIG. 36B is a drawing to show the contents of an atomic pair table in the bond table.

FIG. 37 is a drawing to show the data contents of canonical tree structure data.

FIG. 42 is a drawing to show the structure of another example of the relation information file according to the present invention.

BEST MODE FOR CARRYING OUT THE INVENTION

Figure 1:
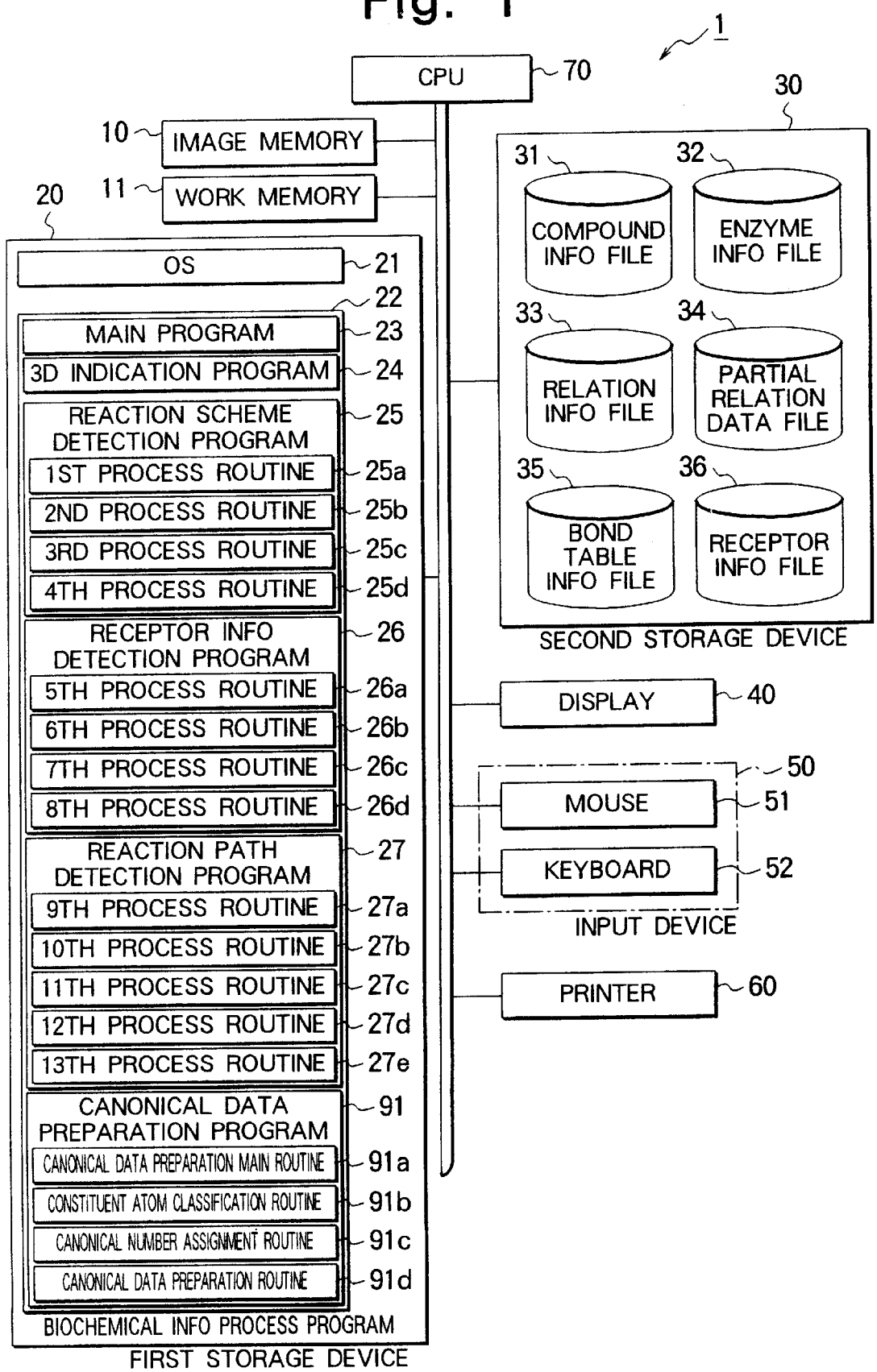
FIG. 1 is a block diagram to show the structure of an example of the biochemical information processing apparatus of the present invention.

The preferred embodiments of the present invention will be described with reference to the accompanying drawings. FIG. 1 is a block diagram to show the structure of the biochemical information processing apparatus 1 according to an embodiment of the present invention. Referring to the drawing, the biochemical information processing apparatus 1 of the present embodiment comprises an image memory 10 for storing image data to indicate a molecular structure diagram or the like of a compound, a work memory 11 for temporarily storing data, a first storage device 20 for storing an operating system (OS) 21 and a biochemical information processing program 22, and a second storage device 30, being storage means, for storing various files. Further, it comprises a display 40 being display means, an input device 50, which is input means, having a mouse 51 for accepting input of image data and a keyboard 52 for accepting input of symbolic data, a printer 60 for outputting the image data or the like, and a CPU 70 for controlling execution or the like of the biochemical information processing program 22.

The biochemical information processing program 22 comprises a main program 23 for generally controlling processing, a three-dimensional indication program 24 for effecting three-dimensional indication of image data, a reaction scheme detection program 25 being reaction scheme detection means, a receptor information detection program 26 being receptor information detection means, and a reaction path detection program 27 being reaction path detection means. The reaction scheme detection program 25 is a program for detecting a chemical reaction scheme concerning a compound as being a substrate and/or a product, which comprises first process routine 25a to fourth process routine 25d. The receptor information detection program 26 is a program for detecting additional information about a receptor, which comprises fifth process routine 26a to eighth process routine 26d. Further, the reaction path detection program 27 is a program for detecting a reaction path of plural compounds, which comprises ninth process routine 27a to thirteenth process routine 27e.

The receptor information detection program 26 can handle not only receptors intrinsic to living bodies, such as hormone receptors, but also receptors of drugs or the like, and conceptual receptors existence of which is not confirmed yet.

The second storage device 30 comprises a compound information file 31, an enzyme information file 32, a relation (correlation) information file 33, a partial correlation data file 34, a bond table file (which will also be referred to as a bond table information file) 35, and a receptor information file 36. Among them, the compound information file 31 stores a list to show the relationship between compound numbers of compounds and canonical data corresponding to the compounds, and additional information (for example, the reference data of FIG. 3) about the compounds. The enzyme information file 32 stores a list to show the relationship among enzyme numbers of enzymes, compound numbers of compounds being substrates of the enzymes, and compound numbers of compounds being products by the enzymes, and additional information (for example, the reference data of FIG. 4) about the enzymes. Further, the relation information file 33 stores a list to show the relationship among compound numbers of compounds, enzyme numbers of enzymes with a relevant compound being a substrate, enzyme numbers of enzymes with a relevant compound being a product, receptor numbers of receptors with a relevant compound being an agonist, and receptor numbers of receptors with a relevant compound being an antagonist. Furthermore, the partial correlation data file 34 is prepared to store the reaction path information while the bond table file 35 to store the bond table data, respectively. Moreover, the receptor information file 36 stores a list to show the relationship among receptor numbers of receptors, compound numbers of compounds being agonists of the receptors, and compound numbers of compounds being antagonists of the receptors, and additional information (for example, the reference data of FIG. 5) about the receptors.

Figure 2:
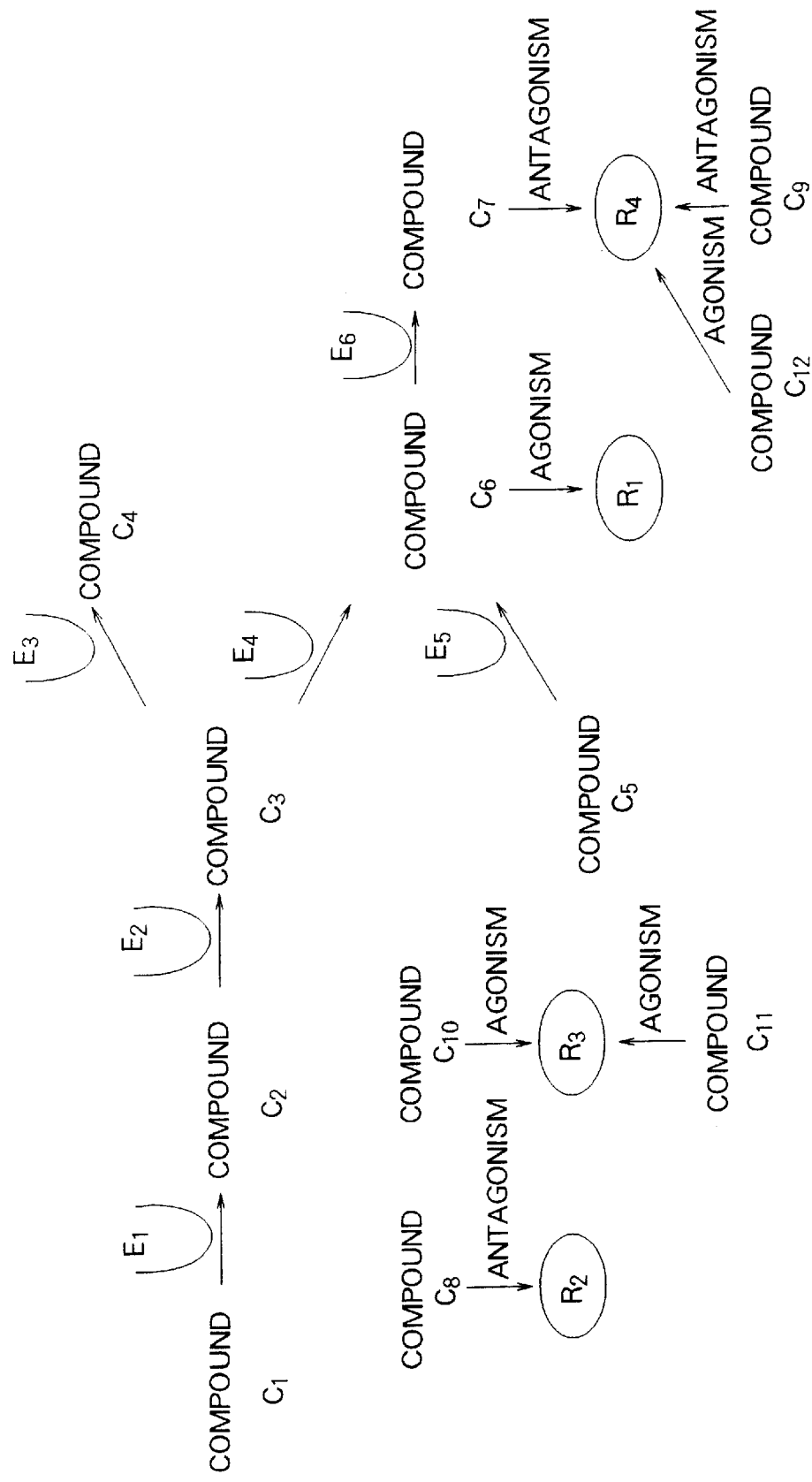
FIG. 2 is an example of a reaction path diagram to show a path in which a compound of compound number $C_1$ changes up to a compound of compound number $C_7$.

Next explained is the detailed structure of the compound information file 31, enzyme information file 32, relation information file 33, and receptor information file 36. FIG. 2 is an example of a reaction path diagram to show a path through which a compound of compound number $C_1$ changes in order to compounds of compound numbers $C_2$, $C_3$, ... with plural enzymes of enzyme numbers $E_1$ to $E_6$ as a catalyst, finally changing into a compound of compound number $C_7$, and is also an example of a drawing to show circumstances in which compounds $C_6$–$C_{12}$ serve as an agonist or as an antagonist to receptors $R_1$–$R_4$.

The compound numbers $C_1$–$C_7$ described in this example of reaction path diagram are recorded in the compound information file 31 shown in FIG. 3. The compound information file 31 includes a record of canonical data corresponding to each compound of compound number $C_1$–$C_7$, and the reference data (name, literature, physical properties, etc.) about each compound of compound number $C_1$–$C_7$ in the form of a list corresponding to the compound numbers $C_1$–$C_7$. When access is made to the compound information file 31, using the compound number $C_1$–$C_7$ as a key, the canonical data and reference data can be read out as to each compound of compound number $C_1$–$C_7$. Here, the canonical data is a plurality of symbolic data for uniquely specifying the chemical structure of each compound. The details of the canonical data will be described hereinafter.

The enzyme numbers $E_1$–$E_6$ described in the example of reaction path diagram of FIG. 2 are recorded in the enzyme information file 32 shown in FIG. 4. The enzyme information file 32 includes a record of the compound numbers $C_1$–$C_6$ of compounds being substrates of the respective enzymes of enzyme numbers $E_1$–$E_6$, the compound numbers $C_2-C_7$ of compounds being products by the respective enzymes of enzyme numbers $E_1-E_6$, and the reference data (name, literature, physical properties, inhibitor, inducer, activator, etc.) about each enzyme of enzyme number $E_1-E_6$ in the form of a list corresponding to the enzyme numbers $E_1-E_6$.

Therefore, when access is made to the enzyme information file 32 using the enzyme number $E_1-E_6$ as a key, the compound numbers $C_1-C_7$ being the substrate and product, and the reference data can be read out as to each enzyme of enzyme number $E_1-E_6$. It is also possible to similarly handle reactions by enzymes not subjected to enzyme classification or to identification of enzyme yet, nonenzymatic reactions involving light, heat, acid, base, metal ion, or the like, and multi-step reactions by a plurality of enzymes.

Figure 5:
FIG. 5 is a drawing to show the structure of a receptor information file.

Further, the receptor numbers $R_1-R_4$ are recorded in the receptor information file 36 shown in FIG. 5. The receptor information file 36 includes a record of the compound numbers $C_6$, $C_{10}-C_{12}$ of the compounds being agonists of the respective receptors of receptor numbers $R_1-R_4$, the compound numbers $C_7-C_9$ of the compounds being antagonists of the respective receptors of receptor numbers $R_1-R_4$, and the reference data (name, literature, physical properties, action, etc.) about each receptor of receptor number $R_1-R_4$ in the form of a list corresponding to the receptor numbers $R_1-R_4$.

Therefore, when access is made to the receptor information file 36, using the receptor number $R_1-R_4$ as a key, the compound numbers $C_6-C_{12}$ being the agonist and antagonist, and the reference data can be read out as to each receptor of the receptor number $R_1-R_4$.

Furthermore, the mutual relation among compound numbers $C_1-C_{12}$, enzyme numbers $E_1-E_6$, and receptor numbers $R_1-R_4$ is recorded in the relation information file 33 shown in FIG. 6. Describing in more detail, the enzyme numbers $E_1-E_6$ of enzymes with each compound of compound number $C_1-C_6$ being a substrate, the enzyme numbers $E_1-E_6$ of enzymes with each compound of compound number $C_2-C_7$ being a product, and the enzyme number $E_4$ of the enzyme inhibited by the compound of compound number $C_6$ are recorded in the form of a list corresponding to the compound numbers $C_1-C_7$. In addition, the receptor numbers $R_1-R_4$ of receptors with each compound of compound number $C_6$, $C_{10}-C_{12}$ being an agonist, and the receptor numbers $R_2$, $R_4$ of receptors with each compound of compound number $C_7-C_9$ being an antagonist are recorded in the form of a list corresponding to the compound numbers $C_6-C_{12}$.

Therefore, when access is made to the relation information file 33, using the compound number $C_1-C_7$ as a key, it is possible to read out the enzyme numbers $E_1-E_6$ of the enzymes with each compound of compound number $C_1-C_7$ being a substrate or a product, and the enzyme number $E_4$ of the enzyme inhibited by the compound of compound number $C_6$. When access is made to the relation information file 33, using the compound number $C_6-C_{12}$ as a key, it is possible to read out the receptor numbers $R_1-R_4$ of the receptors with each compound of compound number $C_6-C_{12}$ being an agonist or an antagonist.

Next, the data contents of the enzyme information file 32 will be explained specifically. First, from the reaction path diagram of FIG. 2, a compound number of a compound being a substrate for the enzyme of enzyme number $E_1$ is $C_1$. A compound number of a compound being a product by the enzyme of the enzyme number $E_1$ is $C_2$. Therefore, $C_1$ is recorded in the column of (substrate) compound number corresponding to the enzyme number $E_1$ in the enzyme information file 32 of FIG. 4. In addition, $C_2$ is recorded in the column of (product) compound number corresponding to the enzyme number $E_1$.

Similarly, from the reaction path diagram of FIG. 2, a compound number of a compound being a substrate for the enzyme of enzyme number $E_2$ is $C_2$. Further, a compound number of a compound being a product by the enzyme of enzyme number $E_2$ is $C_3$. Therefore, $C_2$ is recorded in the column of (substrate) compound number corresponding to the enzyme number $E_2$ in the enzyme information file 32 of FIG. 4. Also, $C_3$ is recorded in the column of (product) compound number corresponding to the enzyme number $E_2$.

Such relation also holds for the enzyme numbers $E_3-E_6$ similarly, so that the compound numbers $C_3-C_7$ along the reaction path diagram of FIG. 2 are recorded in each of the columns of (substrate) compound number and (product) compound number corresponding to the enzyme numbers $E_3-E_6$.

Next, the data contents of the receptor information file 36 will be described specifically. As shown in FIG. 5, the compound number $C_6$ of the compound being an agonist for a receptor of receptor number $R_1$ is recorded in the column of (agonist) compound number. Also, a compound number $C_8$ of a compound being an antagonist for a receptor of receptor number $R_2$ is recorded in the column of (antagonist) compound number. Further, compound numbers $C_{10}$, $C_{11}$ of compounds being agonists for a receptor of receptor number $R_3$ are recorded in the column of (agonist) compound number. Furthermore, a compound number $C_{12}$ of a compound being an antagonist for a receptor of receptor number $R_4$ is recorded in the column of (agonist) compound number while compound numbers $C_7$, $C_9$ of compounds being antagonists for the receptor of receptor number $R_4$ are recorded in the column of (antagonist) compound number. The relation between these receptor numbers and compound numbers is apparent from the reaction path diagram of FIG. 2.

Next, the data contents of the relation information file 33 will be described specifically. First, from the reaction path diagram of FIG. 2, the enzyme number of the enzyme with the compound of compound number $C_1$ being a substrate is $E_1$. Therefore, $E_1$ is recorded in the column of (substrate) enzyme number corresponding to the compound number $C_1$ in the relation information file 33 of FIG. 6.

Similarly, from the reaction path diagram of FIG. 2, the enzyme number of the enzyme with the compound of compound number $C_2$ being a substrate is $E_2$. Also, the enzyme number of the enzyme with the compound of compound number $C_2$ being a product is $E_1$. Therefore, $E_2$ is recorded in the column of (substrate) enzyme number corresponding to the compound number $C_2$ in the relation information file 33 of FIG. 6. Also, $E_1$ is recorded in the column of (product) enzyme number corresponding to the compound number $C_2$.

Such relation also holds for the compound numbers $C_3-C_7$ similarly, so that the enzyme numbers $E_2-E_6$ along the reaction path diagram of FIG. 2 are recorded in each of the columns of (substrate) enzyme number and (product) enzyme number corresponding to the compound numbers $C_3-C_7$ (which are used as a key upon search using the relation information file 33). Further, the compound of compound number $C_6$ is a substrate for the enzyme number $E_6$ and a product for the enzyme number $E_6$, while being an inhibitor for the enzyme number $E_4$, and thus, $E_4$ is recorded in the column of (inhibition) enzyme number.

Furthermore, the receptor number $R_1$ of an agonist for the compound of compound number $C_6$ is recorded in the column of (agonism) receptor number. Also, the receptor number $R_4$ of an antagonist for the compound of compound number $C_7$ is recorded in the column of (antagonism) receptor number. Following in the similar fashion, the receptor numbers $R_2$–$R_4$ of agonist/antagonist for the compounds of compound numbers $C_8$–$C_{12}$ are recorded in each column of (agonism) receptor number/(antagonism) receptor number.

Figure 7:
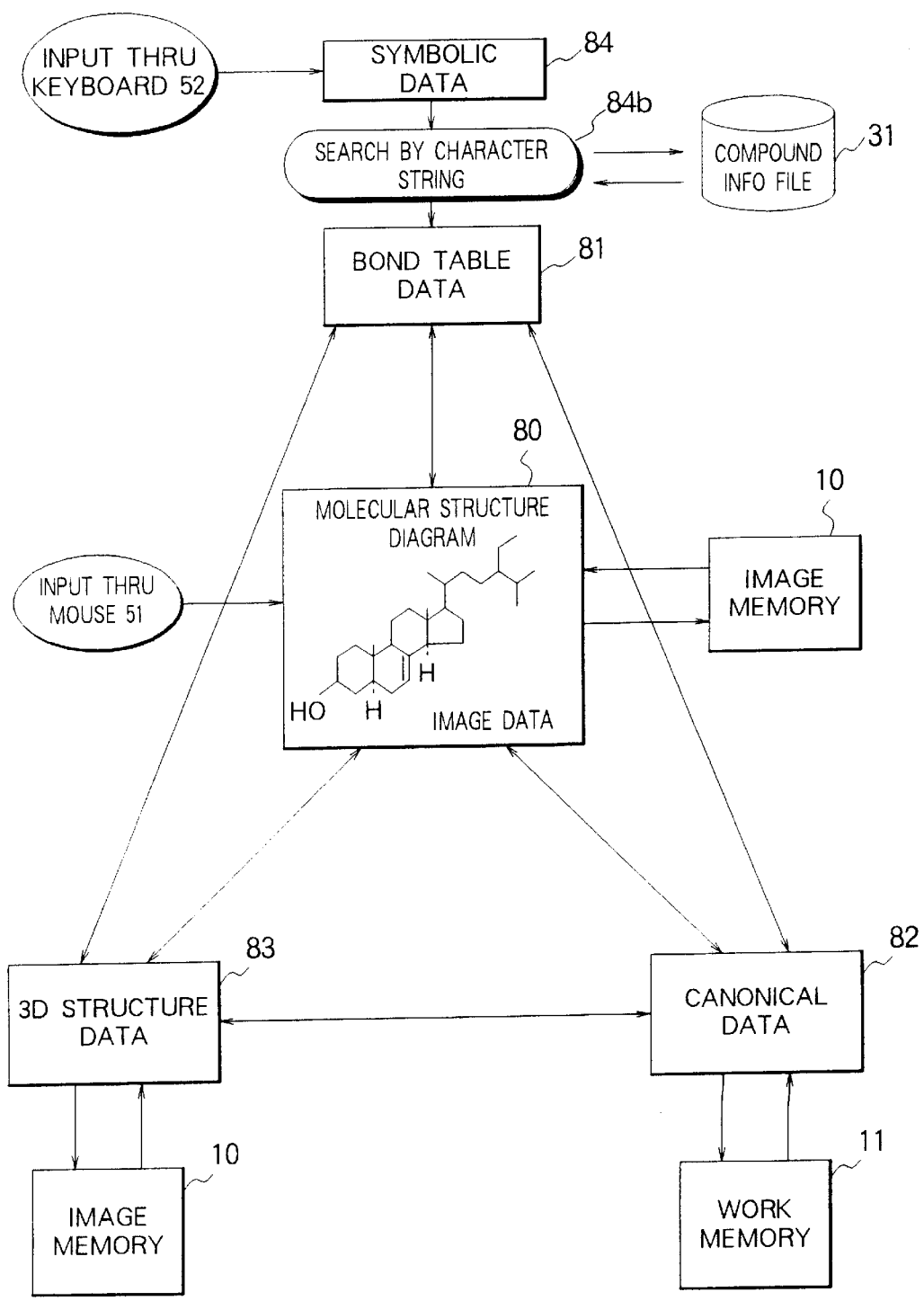
FIG. 7 is a drawing to show the flow of data in the biochemical information processing apparatus.

Next, the flow of data in the biochemical information processing apparatus 1 is shown in FIG. 7. First, an operator draws a molecular structure diagram on the display 40 using the mouse 51, and then this molecular structure diagram is stored as image data 80 in the image memory 10. This image data 80 can be converted into either one of bond table data 81, canonical data 82, and three-dimensional data 83.

Conversion between the image data 80 and the bond table data 81 can be made using a graphic library corresponding to the OS used. The conversion algorithm between the bond table data 81 and the canonical data 82 will be described in detail hereinafter. The conversion algorithm between the bond table data 81 and the three-dimensional data 83 is described in "Abstracts, The 13th symposium of information science, p 25" by the present inventor.

The bond table data 81 after conversion is stored in the bond table file 35, the canonical data 82 in the work memory 11, and the three-dimensional data 83 in the image memory 10, respectively. When the operator gives input of symbolic data 84 indicating a name or the like, using the keyboard 52, a search process 84b by a character string is carried out to the compound information file 31, and compound table data 81 is made from canonical data of a relevant compound. This bond table data 81 can also be converted similarly into either of the image data 80 and the three-dimensional data 83. In contrast, when the symbolic data 84 indicating an enzyme name or the like is input, the search process 84b by a character string is carried out to the enzyme information file 32 to read a corresponding enzyme number out thereof, which can be used for the subsequent processes.

Figures 8A, 8B, 8C:
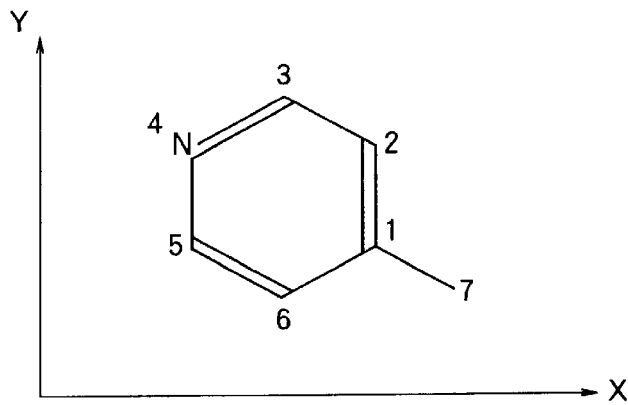
FIG. 8A is a drawing to show a specific example of image data.
FIG. 8B a specific example of bond table data.
FIG. 8C a specific example of canonical data, respectively.

FIG. 8A to FIG. 8C show a specific example of image data 80a, bond table data 81a, and canonical data 82a. FIG. 8A is the image data 80a to show the molecular structure of compound "4-methylpyridine". This image data 80a can be converted into the bond table data 81a shown in FIG. 8B. The bond table data 81a is a table in which the number of atoms, the number of bonds, coordinates of each atom, an element symbol of each element, and so on are recorded. Using this bond table data 81a, structures of all compounds can be expressed as numerical data.

Further, the bond table data 81a can be converted into the canonical data 82a shown in FIG. 8C. The canonical data 82a is a symbolic string including an array of numerals, marks, and so on. As shown in FIG. 8C, the canonical data 82a of compound "4-methylpyridine" "1%1%1-2%3%5% N/6%7/". In this way, the canonical data 82a can express the structure of a compound in the form of a very short symbolic string. Because of it, if this canonical data 82a is applied, for example, to a compound search system, the search speed can be increased and the storage resource can be effectively utilized.

Figures 9A, 9B, 9C:
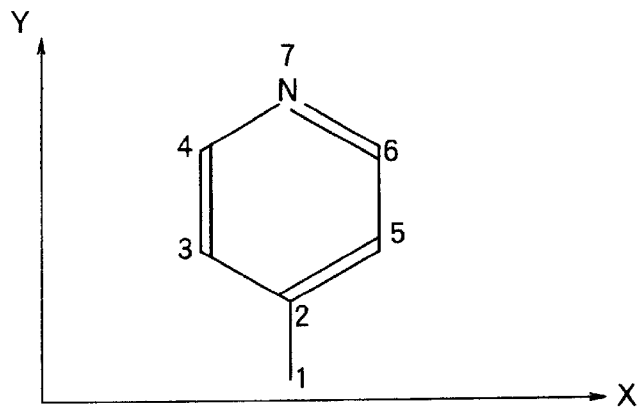
FIG. 9A is a drawing to show a specific example of image data.
FIG. 9B a specific example of bond table data.
FIG. 9C a specific example of canonical data, respectively.

It is, however, not easy to uniquely specify a compound with the bond table data described above, and it is thus not suitable to apply the bond table data to the compound search system. Namely, as shown in FIG. 9A to FIG. 9C, the image data 80b is the data expressing the same compound as the image data 80a, but the bond table data 81b is utterly different from the bond table data 81a. It is seen from this that a compound cannot be uniquely specified from the bond table data. In contrast with it, the canonical data 82b obtained by converting the bond table data 81b is the same as the canonical data 82a, and can uniquely specify the compound.

In the bond table data 81a and 81b, the table with each data recorded is separated into a table of from atom number to mass and a table of from bonding atom pair to UP/DOWN. Accordingly, for example in the bond table data 81a, the atom number (4) and the element symbol (N) correspond to each other, but the atom number (4) does not correspond to the bonding atom pair (4 5), the type of bond (1) and UP/DOWN (0).

Particularly, as shown in FIG. 10A to FIG. 10C, two image data 80c, 80d are completely different from each other when looked at, though the both are image data indicating a same compound. The canonical data 82c resulting from conversion of such image data 80c, 80d is the same, thus proving that the canonical data can uniquely specify a compound.

As described, the canonical data is more excellent than the bond table data in that it can uniquely specify a compound, and therefore, the canonical data is mainly used in each process of the biochemical information processing apparatus 1 of the present embodiment.

On the other hand, since the bond table data has the coordinate data, it is useful to display a molecular structure diagram of compound on the display 40. Further, the two-dimensional coordinate data (X-coordinate and Y-coordinate) can be obtained by calculation from other data in the bond table data (though it is of course necessary to preliminarily designate the lengths of bonds, angles between bonds, the position of the center when displayed on the display, and so on).

Next, the biochemical information processing method according to the embodiment of the present invention will be explained. The biochemical information processing apparatus 1 is used for this processing method. First, under control of OS 21, the main program 23 of the biochemical information processing program 22 is started.

Figure 11:
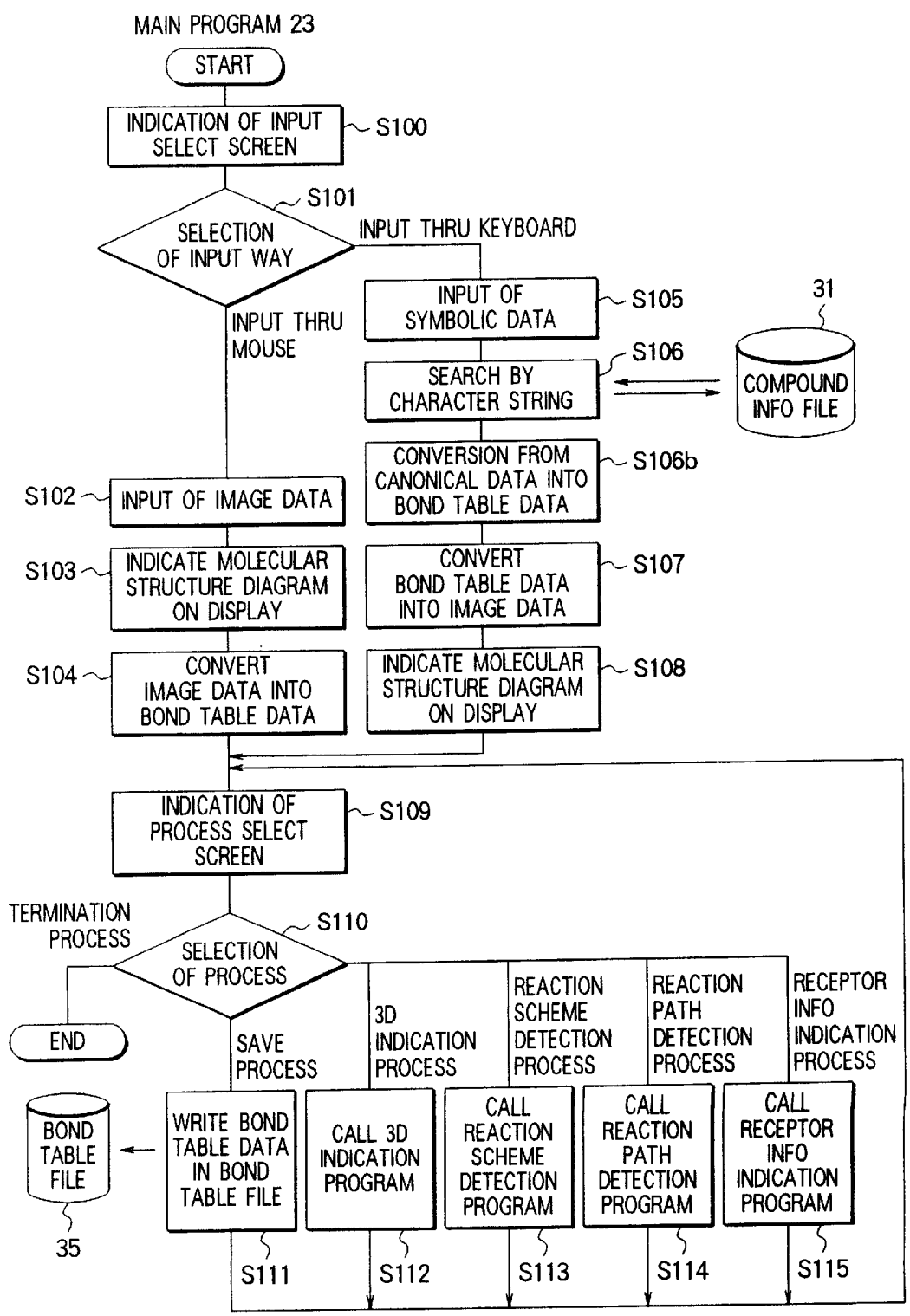
FIG. 11 is a flowchart to show the flow of process of a main routine.

In the main program 23, as shown in the flowchart of FIG. 11, a selection screen of input method is first indicated on the display 40 (S100). When in accordance with this screen indication the operator selects input through the mouse 51 (S101), a screen for drawing of molecular structure diagram is indicated on the display 40. When the operator next inputs a molecular structure diagram indicating the structure of a predetermined compound using the mouse 51, this graphic image is accepted as image data to be stored in the image memory 10 (S102). This image data is also indicated on the display 40 (S103). Then this image data is converted into bond table data in accordance with the conversion algorithm discussed above (S104).

When in accordance with the screen indication of S100 the operator selects input through the keyboard 52 (S101), a symbolic string input screen is indicated on the display 40. When the operator next gives input of a symbolic string of a compound name, a chemical formula, or the like for specifying a predetermined compound using the keyboard, this input is accepted (S105), search of a compound specified by this symbolic string (S106) is carried out to the compound information file 31, and the bond table data 81 is prepared from the canonical data 82 of the pertinent compound (S106b). Then the bond table data is converted into image data, based on the aforementioned two-dimensional coordinate data (S107), and this image data is indicated on the display 40 (S108).

On the other hand, when through input by the keyboard 52 symbolic data 84 indicating an enzyme name or the like is given, search by a character string (S106) is carried out to the enzyme information file 32 and a pertinent enzyme number is read out thereof to be used in similar processing.

After completion of processing at S104 and at S108, a selection screen for selecting either one of the following processes is indicated on the display 40 (S109). When in accordance with this screen indication the operator selects a save process of the bond table data, the bond table data is written into the bond table file 35 (S111). After completion of writing into the bond table file 35, the processing returns to S109. When in accordance with the screen indication of S109 the operator selects a three-dimensional indication process, the three-dimensional indication program 24 is called out (S112). The three-dimensional indication program 24 is a processing program for three-dimensionally indicating a molecular structure diagram of compound. After completion of the process of three-dimensional indication program 24, the processing then returns to S109.

Further, when in accordance with the screen indication of S109 the operator selects a reaction scheme detection process, the reaction scheme detection program 25 is called (S113). The reaction scheme detection program 25 is a processing program for searching the relation information file 33 or the like and detecting a reaction scheme involving the compound. After completion of the process of reaction scheme detection program 25, the processing then returns to S109. Furthermore, when in accordance with the screen indication of S109 the operator selects a reaction path detection process, the reaction path detection program 27 is called (S114). The reaction path detection program 27 is a processing program for searching the relation information file 33 or the like and detecting a reaction path of plural compounds. After completion of the process of reaction path detection program 27 the processing then returns to S109.

Moreover, when in accordance with the screen indication of S109 the operator selects a receptor information indication process, the receptor information detection program 26 is called (S115). The receptor information detection program 26 is a processing program for searching the relation information file 33 to read out an agonism receptor number and/or an antagonism receptor number of a specific compound (the sixth process routine 26b), searching the receptor information file 36 to detect the reference data for the receptor of the receptor number thus read out (the seventh process routine 26c), and further indicating the reference data thus detected (the eighth process routine 26d). After completion of the process of receptor information detection program 26, the processing then returns to S109. Furthermore, when in accordance with the screen indication of S109 the operator selects a termination process, the entire processing of the main program is terminated.

Figure 12:
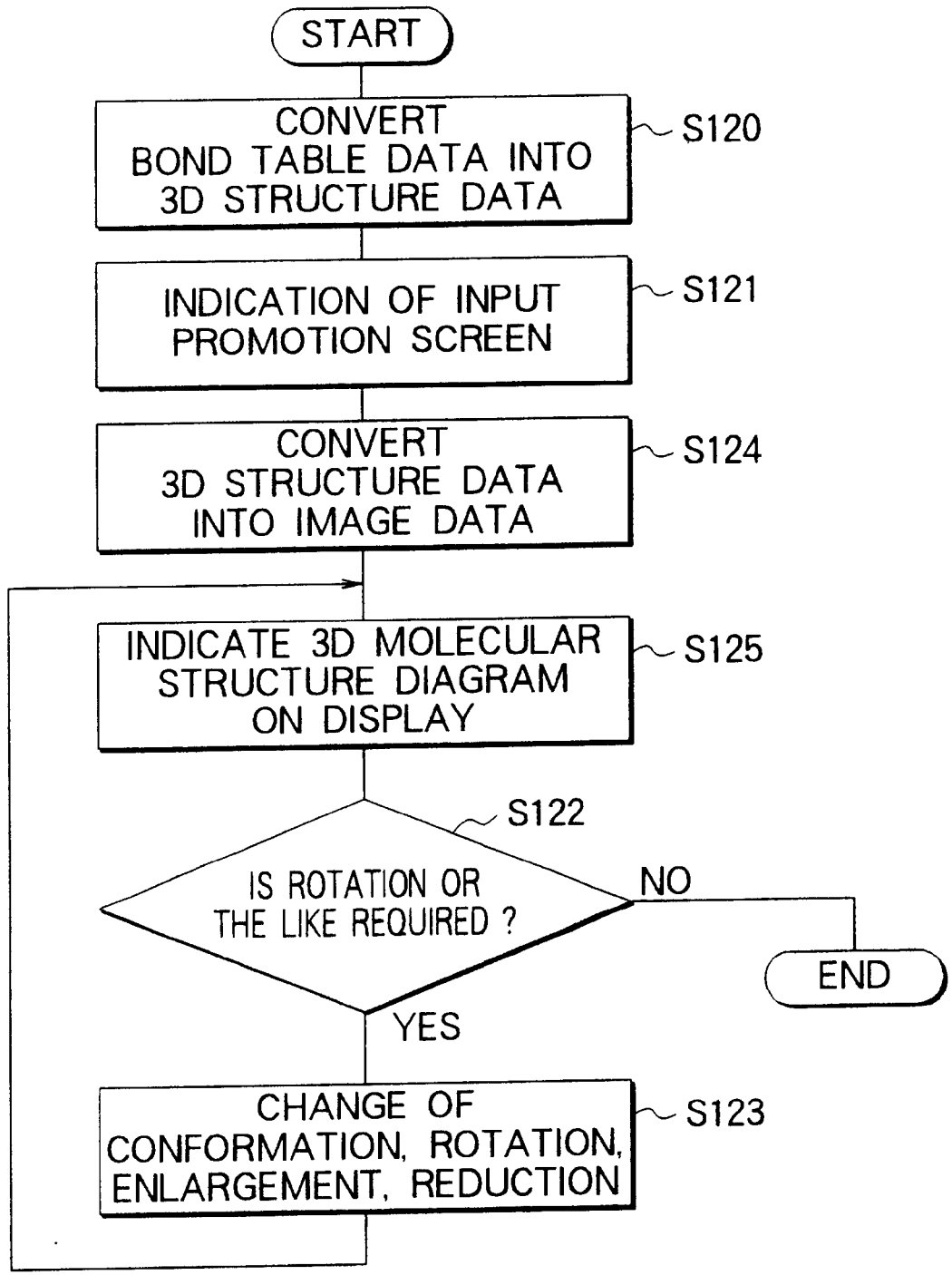
FIG. 12 is a flowchart to show the flow of process of a three-dimensional indication routine.

Next explained using the flowchart of FIG. 12 is the process of three-dimensional indication program 24 called at S112. In this process, first, the bond table data is converted into the three-dimensional data of molecular structure diagram in accordance with the above-described conversion algorithm (S120). Then an input promotion screen as to whether rotation indication or the like of this three-dimensional data is required is indicated on the display 40 (S121). When start of the three-dimensional indication program 24 is selected on this screen, the three-dimensional data is converted into image data, using the graphic library corresponding to the OS used (S124), and this image data is indicated on the display 40 (S125). Further, when in accordance with this the screen indication the operator selects either one of a change process of conformation, a rotation process, an enlargement process, and a reduction process (S122), either of these processes is carried out by ordinary formation techniques of three-dimensional graphics (S123).

Figure 13:
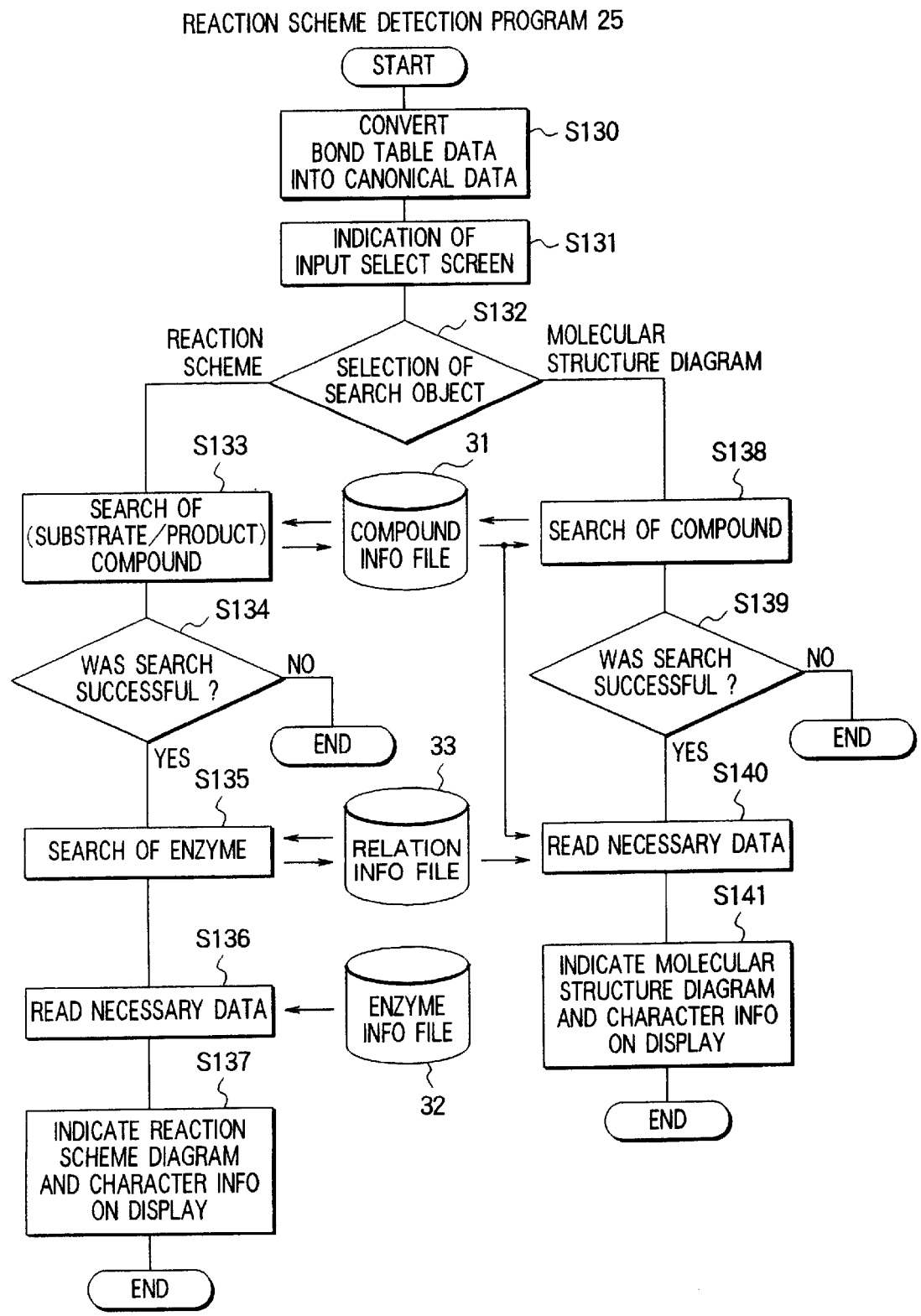
FIG. 13 is a flowchart to show the flow of process of a reaction scheme detection routine.

Next explained using the flowchart of FIG. 13 is the process of reaction scheme detection program 25 called at S113. In this process, first, the bond table data is converted into canonical data in accordance with the conversion algorithm as discussed hereinafter (S130). Then a selection screen of search object is indicated on the display 40 (S131). Here, in the case of the operator selecting a reaction scheme, it is preferable that the compound input have preliminarily been designated as either a substrate or a product at previous S102 or S105. Alternatively, immediately before the process of S130 input of designation of either a substrate or a product may be accepted together with the bond table data for the compound.

Under such conditions, when in accordance with the screen indication of S131 the operator selects a reaction scheme (S132), the following reaction scheme detection process is carried out. In this process, first, access is made to the compound information file 31 to search for a compound (S133). This search process is carried out based on the canonical data of the compound converted into at S130. When this search process ends with the result that the same canonical data as the canonical data of the compound does not exist in the compound information file 31 (S134), the process is terminated. If the same canonical data as the canonical data of the compound exists in the compound information file 31, the compound number corresponding to this canonical data is read out of the compound information file 31.

Based on the compound number (a key) read out at S133, an enzyme number (according to the aforementioned designation) with the compound being a substrate or a product is read out of the relation information file 33 (S135). Further, based on the enzyme number read out at S135, a (substrate) compound number, a (product) compound number, and reference data corresponding to this enzyme number are read out of the enzyme information file 32 (S136).

In this manner a reaction scheme diagram involving the compound is prepared from the compound number read out at S133 and the enzyme number read out at S135, and the image data of this reaction scheme diagram is indicated on the display 40. Also, the reference data about the enzyme read out at S136 is indicated on the display 40 (S137).

The image data of reaction scheme diagram is indicated on the display 40 preferably in such an arrangement that an arrow combines a molecular structure diagram of the compound of the (substrate) compound number obtained with a molecular structure diagram of the compound of (product) compound number and that the reference data of enzyme (especially, the name) is placed near the arrow. Conversion from the compound number to the molecular structure diagram may be carried out, for example, in the order of the compound number, the bond table data (making access to the bond table file), and the molecular structure diagram (using the two-dimensional coordinates).

Here, the first process routine 25a performs the processes of from S130 to S133, and these processes correspond to the first step. Also, the second process routine 25b performs the process of S135, and this process corresponds to the second step. Further, the third process routine 25c performs the process of S136, and this process corresponds to the third step. Yet further, the fourth process routine 25d performs the process of S137, and this process corresponds to the fourth step.

In the present invention, the first process portion, step and process routine, the fifth process portion, step and process routine, and the ninth process portion, step and process routine may be the same process portion, step and process routine, respectively.

Next, when in accordance with the screen indication of S131 the operator selects a molecular structure diagram (S132), the following molecular structure diagram detection process is carried out. In this process, first, access is made to the compound information file 31 to search for a compound of detection object (S138). The search process is carried out based on the canonical data of the compound converted into at S130. If this search process ends with the result that the same canonical data as the canonical data of the detection object does not exist in the compound information file 31 (S139), the process is terminated. If the same canonical data as the canonical data of the detection object exists in the compound information file 31, the compound number of the compound corresponding to this canonical data is read out of the compound information file 31.

Based on the compound number read out al S138, the reference data etc. is read out of the compound information file 31 and relation information file 33 (S140). In this manner a molecular structure diagram of the compound being a detection object is prepared from the compound number read out at S138, and the image data of this molecular structure diagram is indicated on the display 40. The reference data for this compound read out at S140 is also indicated on the display 40 (S141).

Figure 14:
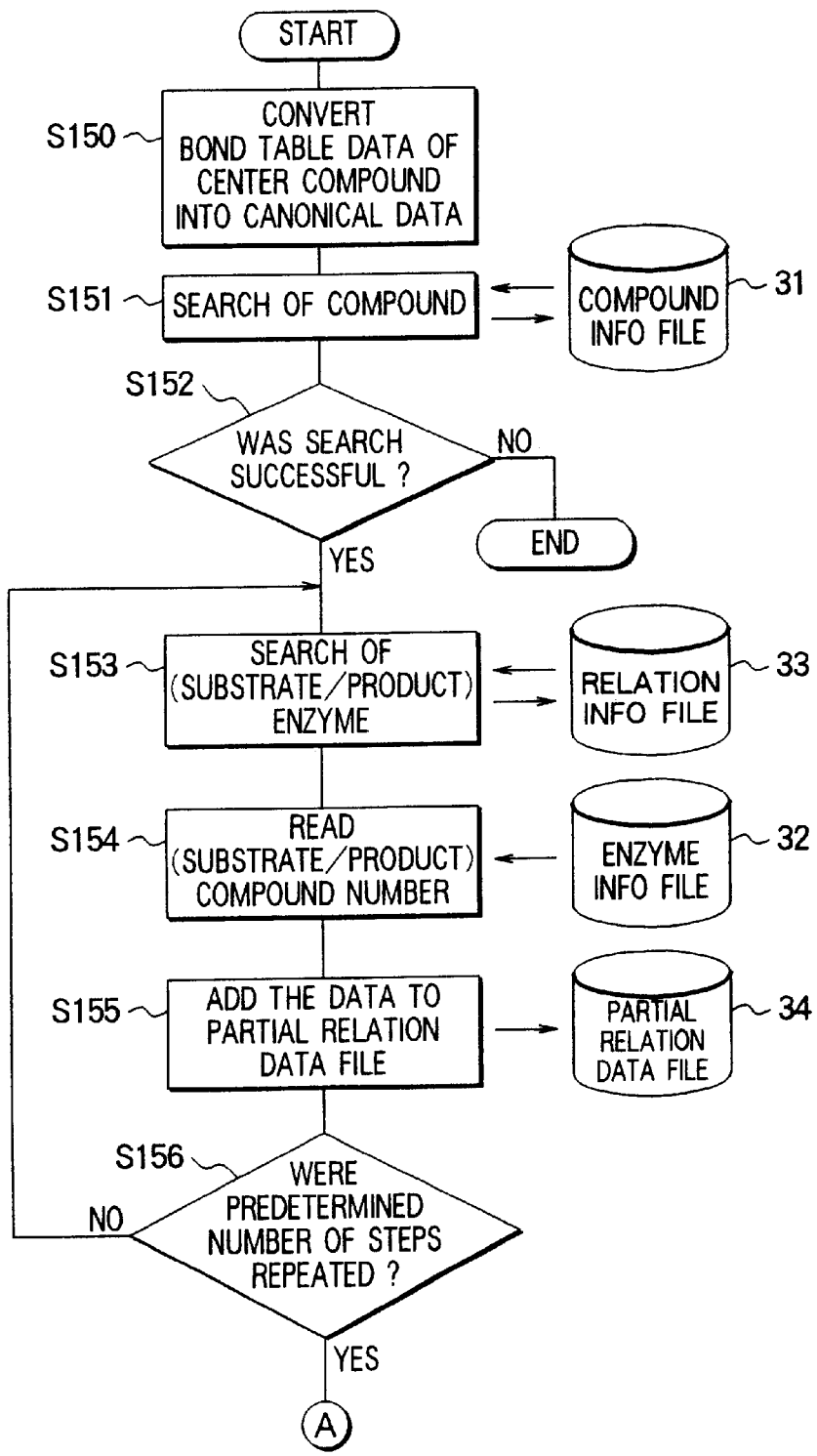
FIG. 14 is a flowchart to show the flow of process of a reaction path detection routine.
Figure 15:
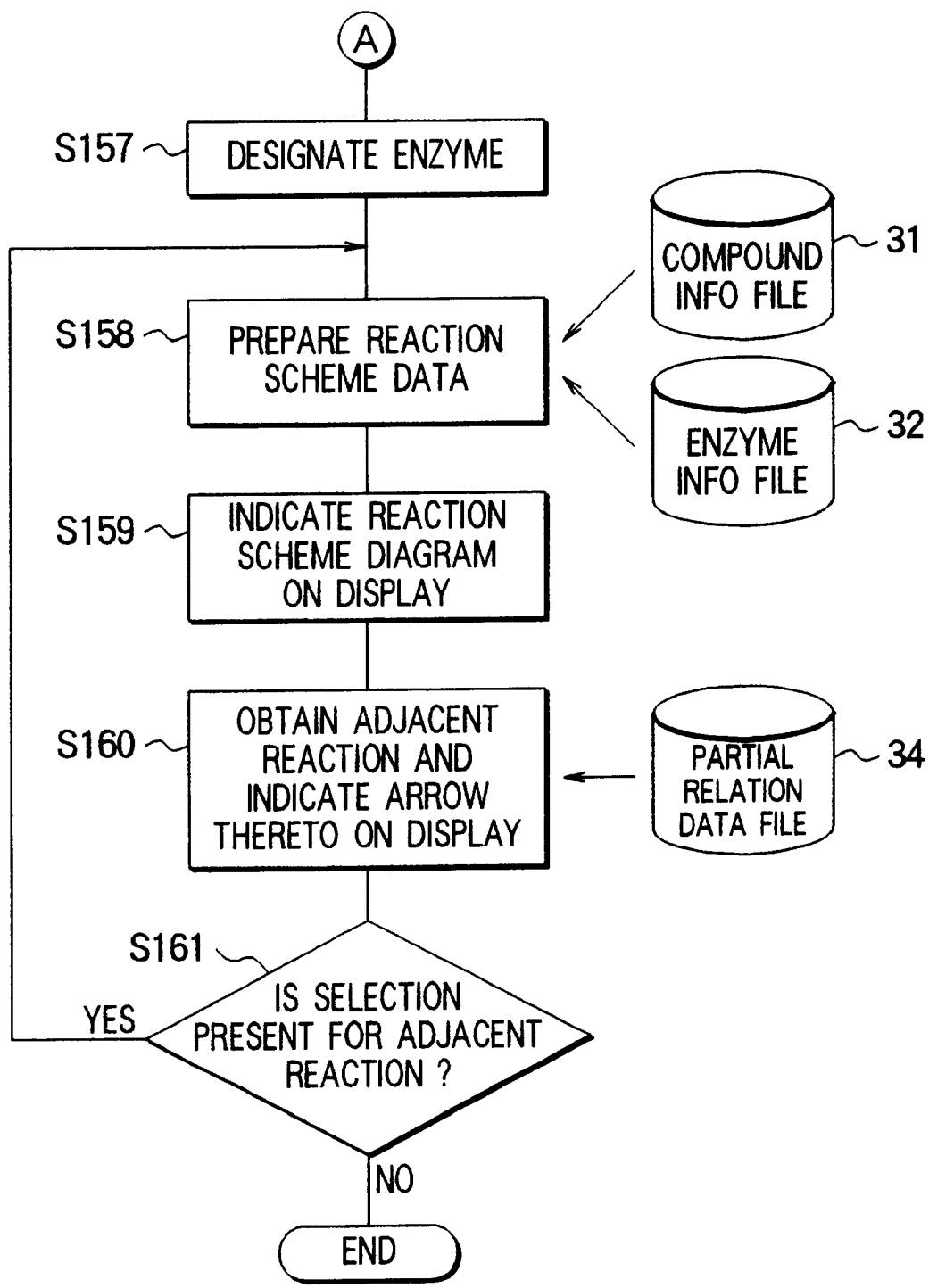
FIG. 15 is a flowchart to show the flow of process of the reaction path detection routine.

Next explained using the flowcharts of FIG. 14 and FIG. 15 is the process of reaction path detection program 27 called at S114. In this process, first, the bond table data of the center compound is converted into canonical data in accordance with the conversion algorithm discussed hereinafter, and subsequently, in order to determine a reaction path area to be detected, input of the number of predetermined reaction steps (for example, three reaction steps on the upstream side and five reaction steps on the downstream side with respect to the center compound at the center) is accepted (S150).

Next, access is made to the compound information file 31 to search for the center compound, based on the canonical data converted into at S150 (S151). If this search process ends with the result that the same canonical data as the canonical data of the center compound does not exist in the compound information file 31 (S152), the process is terminated. If the same canonical data as the canonical data of the center compound exists in the compound information file 31, the compound number corresponding to this canonical data is read out of the compound information file 31.

Based on the compound number (a key) read out at S151, an enzyme number of an enzyme with this compound being a substrate and an enzyme number of an enzyme with this compound being a product are read out of the relation information file 33 (S153). Further, based on each enzyme number read out at S153, a compound number of a compound being a substrate for this enzyme and a compound number of a compound being a product by this enzyme are read out of the enzyme information file 32 (S154). Then the enzyme numbers read out at S153 and the compound numbers read out at S154 are successively added into the partial correlation data file 34 (S155).

The processes of from S153 to S155 are repeated for each compound number newly read out at S154, and compound numbers of all compounds and enzyme numbers of all enzymes within the reaction path of the predetermined number of steps are written into the partial correlation data file 34 (S156).

Next, when a predetermined enzyme is designated in the reaction path in accordance with an instruction of the operator (S157), a compound being a substrate for this enzyme and a compound being a product by this enzyme are read out of the compound information file 31 and the enzyme information file 32, and reaction scheme data is prepared from these compounds and enzyme (S158). Then this reaction scheme data is indicated on the display 40 (S159). Further, access is made to the partial correlation data file 34 to obtain all adjacent reactions of this reaction scheme, and arrows indicating these adjacent reactions are indicated on the display 40 (S160).

When the operator selects an indication of either one adjacent reaction, based on the reaction scheme data thus indicated on the display 40 (S161), the flow returns to the process of S157 to prepare the reaction scheme data for the adjacent reaction.

Here, the ninth process routine 27a performs the processes of S150 and S151, and these processes correspond to the ninth step. Also, the tenth process routine 27b performs the process of S153, and this process corresponds to the tenth step. Further, the eleventh process routine 27c performs the process of S154, and this process corresponds to the eleventh step. Furthermore, the twelfth process routine 27d performs the process of S156, and this process corresponds to the twelfth step. Moreover, the thirteenth process routine 27e performs the processes of from S157 to S161, and these processes correspond to the thirteenth step.

Examples of indications on the display 40 by the processes of S159 and S160 are shown in FIG. 16 and FIG. 17. From these drawings, the image data 80f, 80g each indicating the reaction scheme data is displayed on the display 40 and arrows indicating adjacent reactions are added to the both ends of the reaction scheme data. Selection of adjacent reaction at S161 is effected by clicking a portion of either one arrow by the mouse 51. In this example, when the arrow at the left end of the image data 80f is clicked by the mouse 51, the image data 80g, which is a reaction one step before, is indicated. Any reaction scheme within the reaction path can be freely indicated by such switching of screen.

Next explained are canonical data preparation means and method suitably applicable to the present invention.

Algorithms applicable as the aforementioned conversion algorithm between the bond table data 81 and the canonical data 82 in either way include the known Morgan algorithm (H. L. Morgan, J. Chem. Doc., 5(2), 107 (1965)) and the conversion algorithm by the present inventor, as described in Atsushi TOMONAGA "A Program Library for Chemical Information and Its Applications" Abstracts, The 13$^{th}$ symposium of information science, pages 25–28 (1990). However, the conventional conversion algorithm by the present inventor was able to obtain the canonical data more quickly than the Morgan algorithm without intervention of a process for classifying atoms into equivalent atoms, but because an attribute of an atom used therein was the number of atoms located at a specific minimum distance from the pertinent atom, it lacked preciseness of determination of equivalent atom and reliability of canonical data obtained was not sufficient yet. Accordingly, the present invention particularly preferably employs the canonical data preparation means and method described in detail in the following.

First explained is the canonical data preparation means suitably applicable to the present invention. The biochemical information processing apparatus 1, being the embodiment of the present invention shown in FIG. 1, comprises the canonical data preparation means according to the present invention; that is, it comprises the image memory 10 for storing the image data of molecular structure diagram, the work memory 11 for temporarily storing the symbolic data or the like, the first storage device 20 storing the operating system (OS) 21 and canonical data preparation program 91, and the second storage device 30 storing the bond table file 35 and compound information file 31.

The biochemical information processing apparatus 1 comprises the display 40 for indicating the molecular structure diagram, the mouse 51 being a pointing device for accepting input of hand-drawn graphic image, the keyboard 52 for accepting input of symbolic data such as a chemical formula, the printer 60 for outputting the molecular structure diagram, and the CPU 70 for controlling execution or the like of the canonical data preparation program 91. The pointing devices include a tablet, a digitizer, a light pen, and so on as well as the mouse 51, and either one of these devices may replace the mouse 51.

The canonical data preparation program 91 is a program for preparing the canonical data based on characteristic data about each of atoms constituting a compound and bond pair data between atoms. This canonical data preparation program 91 comprises a main routine 91a for generally controlling the processing, and a constituent atom classification routine (constituent atom classification process portion) 91b for assigning class numbers to the respective atoms constituting the compound. The canonical data preparation program 91 also comprises a canonical number assignment routine (canonical number assignment process portion) 91c for assigning canonical numbers to the respective atoms, based on the class numbers, and a canonical data preparation routine (canonical data preparation process portion) 91d for preparing canonical data, based on the canonical numbers of the respective atoms. The second storage device 30 is provided with the bond table file 35 capable of storing a plurality of bond tables 81. A bond table 81 includes a record of characteristic data about each of the atoms constituting the compound and bond pair data between atoms, and the canonical data preparation program 91 can make access to these data through the bond table 81.

As shown in FIG. 18A and FIG. 18B, a bond table 81 comprises an atomic table 81c including a record of characteristic data about the respective atoms, and an atomic pair table 81d including a record of bonding pair data between atoms. Specifically, the atomic table 81c is provided with columns for input number (also referred to as a number of atom), two-dimensional coordinates (X-coordinate and Y-coordinate) of atom, element symbol (which is generally an element name), attribute, the number of atoms, and the number of bonds to be written wherein (see FIG. 18A), and the atomic pair table 81d is provided with columns for bond atom pair data, the type of bond (for example, 1 for single bond and 2 for double bond), and the structure (a column for distinction as to whether each atom belongs to a cyclic part or to a chain part of molecular structure diagram) to be written therein (see FIG. 18B). Here, the input numbers are numbers for the computer to identify the atoms constituting the compound, and are numerals in the example of FIG. 18A, but may be symbols. The bonding atom pair data is preferably expressed as a combination of input numbers.

The preparation of canonical data does not require the all data in the above atomic table 81c and atomic table 81d, but sufficient data includes the number and element symbol of each atom as characteristic data and the bonding atom pair data and type of bond as bonding pair data.

The second storage device 30 stores the compound information file 31 including a record of a list to show the relation between a compound number of a compound and canonical data corresponding to the compound. As shown in FIG. 3, the compound information file 31 is a file including a record of the canonical data corresponding to each compound of compound number $C_1$–$C_7$ and the reference data (name, literature, physical properties, etc.) about each compound of compound $C_1$–$C_7$ in the form of a list corresponding to the compound numbers $C_1$–$C_7$. Therefore, if access is made to the compound information file 31 using the compound number $C_1$–$C_7$ as a key, the canonical data and reference data can be read out for each compound of compound number $C_1$–$C_7$. Here, the canonical data is data comprised of a plurality of symbols for uniquely specifying the chemical structure of each compound.

The constituent atom classification routine 91b corresponds to the constituent atom classification step, the canonical number assignment routine 91c to the canonical number assignment step, and the canonical data preparation routine 91d to the canonical data preparation step, respectively.

Figure 19:
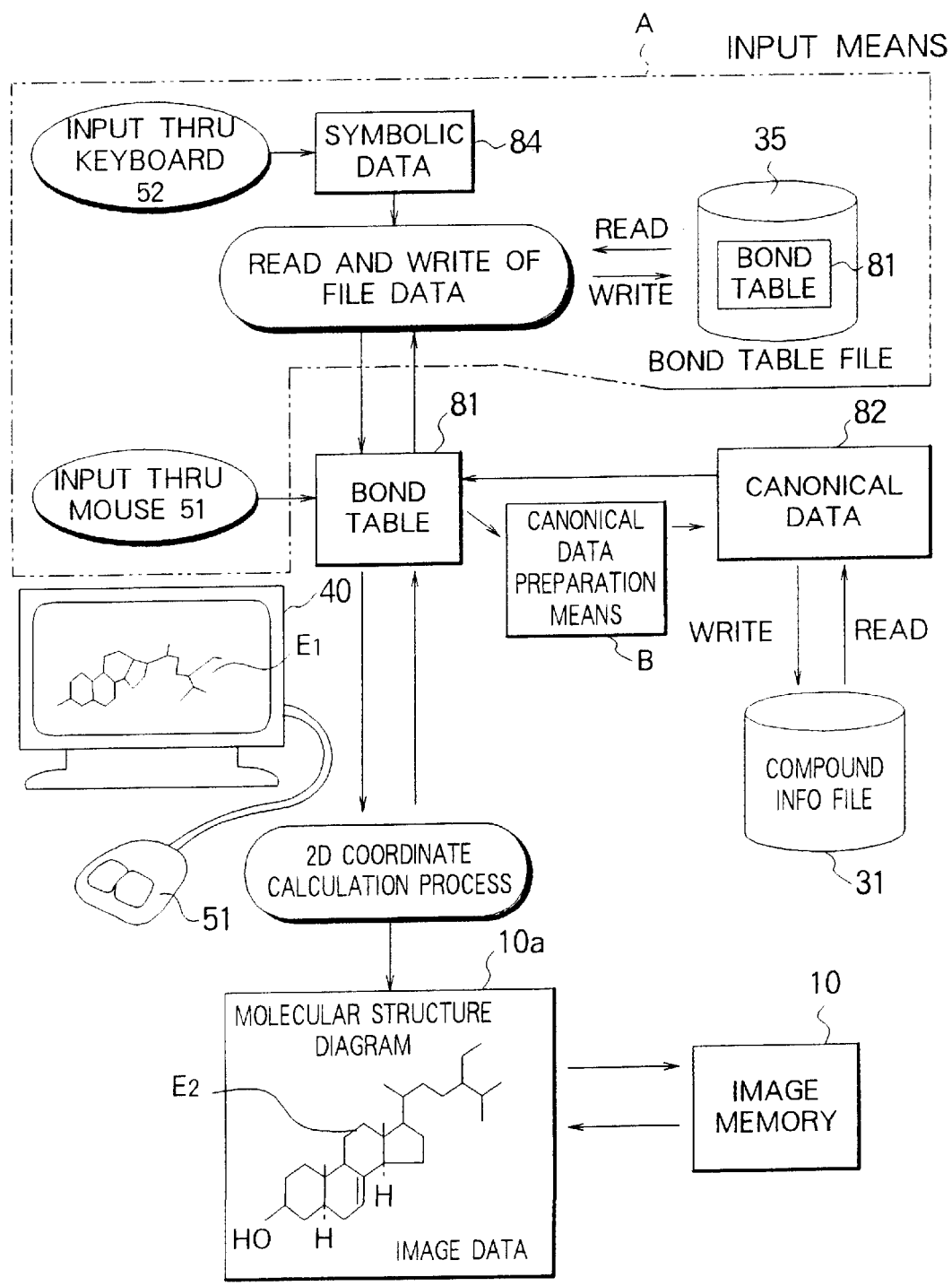
FIG. 19 is a schematic drawing to show the schematic operation of a canonical data preparing apparatus.

Next explained is the schematic operation of the canonical data preparation means. As shown in FIG. 19, the operator manipulates the mouse 51 or the keyboard 52 to prepare a bond table 81 of a compound to become a preparation object of canonical data in the bond table file 35.

Input through the mouse 51 is handwritten input of the molecular structure diagram of a compound on the display 40 with the mouse 51, and an input number of each atom defined in the input order is written in the column of input number in the bond table 81 prepared in the second storage device 30. Further, bonding atom pair data indicating the bond relation of each atom of this molecular structure diagram $E_1$ is written into the column of bonding atom pair in the bond table 81. As described, in the case of the input through the mouse 51, the bond table 81 for specifying a compound is prepared from the handwritten molecular structure diagram $E_1$.

Input through the keyboard 52 is input of a symbolic string for specifying a bond table name corresponding to a predetermined compound using the keyboard 52, and, based on input symbolic data 11a, a bond table 81 specified by this bond table name is read out of the bond table file 35.

As described, the mouse 51 and keyboard 52 compose input means A (50), and a bond table 81 is obtained using either one of the mouse 51 and keyboard 52. Then the canonical data preparation program 91, being canonical preparation means B, is carried out to prepare the canonical data 82, based on each data in the bond table 81. The canonical data 82 thus prepared is written into the compound information file 31 to be saved therein. Here, a reason why the canonical data 82 is prepared from the bond table 81 to be saved is that a storage area thereof is smaller than that when the bond table 81 itself is saved and a compound can be uniquely specified. Namely, the canonical data 82 prepared based on the bond table 81 shown in FIGS. 18A and 18B is "1%1%1-2%3%5% N/6%7/", and can express the structure of the compound by a very short string of character, numeral, and symbol and uniquely. By employing such a short symbolic string as an object of save, the storage resource can be effectively utilized, which can contribute to size and weight reductions of apparatus.

The two-dimensional coordinate calculation process is carried out based on each data in the bond table 81, thereby obtaining two-dimensional coordinate data of each atom. A molecular structure diagram $E_2$, excellent in an aesthetic sense, is prepared from the two-dimensional coordinate data thus obtained. The molecular structure diagram $E_2$ thus prepared can be indicated on the display 40 or can be output from the printer 60.

The input through the keyboard 52 may be arranged to directly write the aforementioned data or the like to indicating bonding states of atoms into the bond table 81 prepared in the second storage device 30. Input of bond table data may be accepted using a device for optically reading graphics or characters, such as an image scanner or an optical card reader (OCR), as the input device of the present invention.

Next explained is the canonical data preparation method being the embodiment according to the present invention. The canonical data preparation means described above is used for this preparation method. First, the main routine 91a of the canonical data preparation program 91 is started under control of OS 21.

Figure 20:
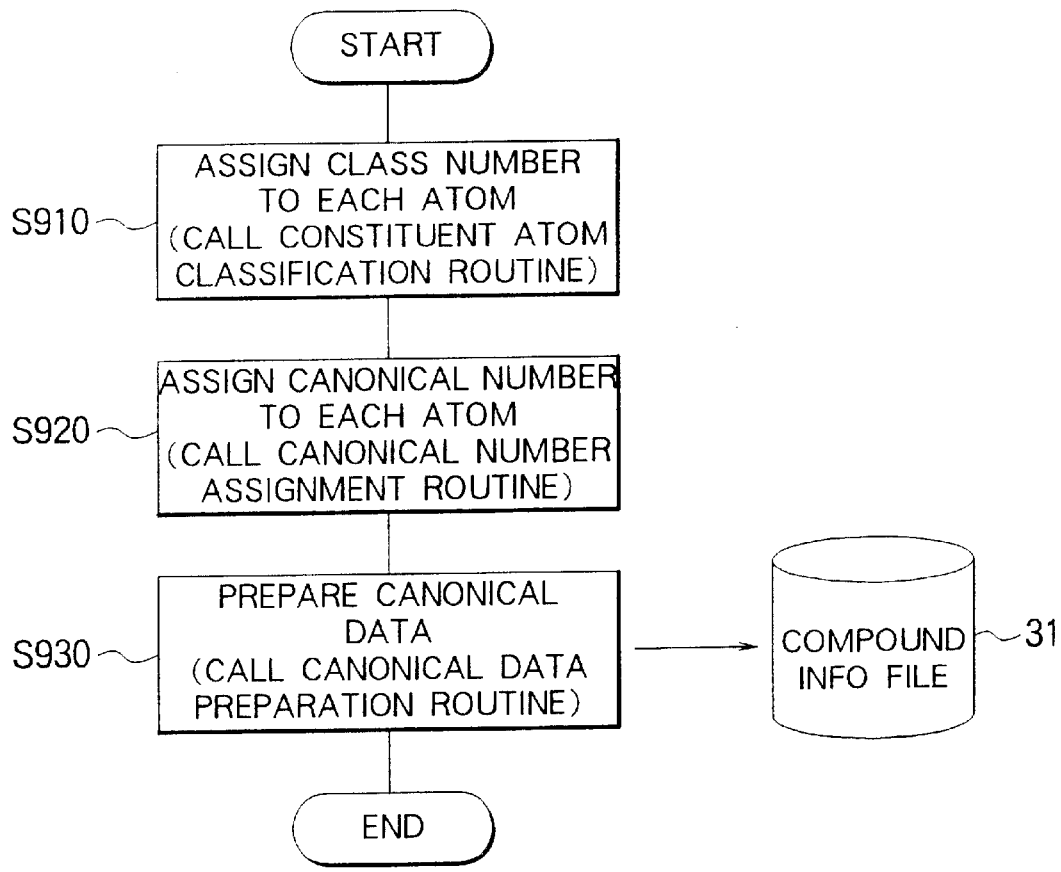
FIG. 20 is a flowchart to show the schematic process of the main routine.

As shown in the flowchart of FIG. 20, the main routine 91a first calls the constituent atom classification routine 91b to assign a class number to each of atoms forming a compound (S910). Next, the canonical number assignment routine 91c is called to assign a canonical number to each atom, based on the class numbers assigned to the respective atoms (S920). Further, the canonical data preparation routine 91d is called to prepare canonical data, based on the canonical numbers assigned to the respective atoms (S930). The canonical data thus prepared is written into the compound information file 31 to be saved therein.

Next explained is the process of constituent atom classification routine 91b called at S910. This process is a process for classifying each of the atoms constituting the compound into different classes each for equivalent atoms and giving each atom a class number corresponding to a class to which the each atom belongs. For example, since all atoms of benzene are equivalent, a same class number is given to the all. In contrast, since each atom of toluene is not equivalent to each other, different class numbers are given to the respective atoms.

Figure 21:
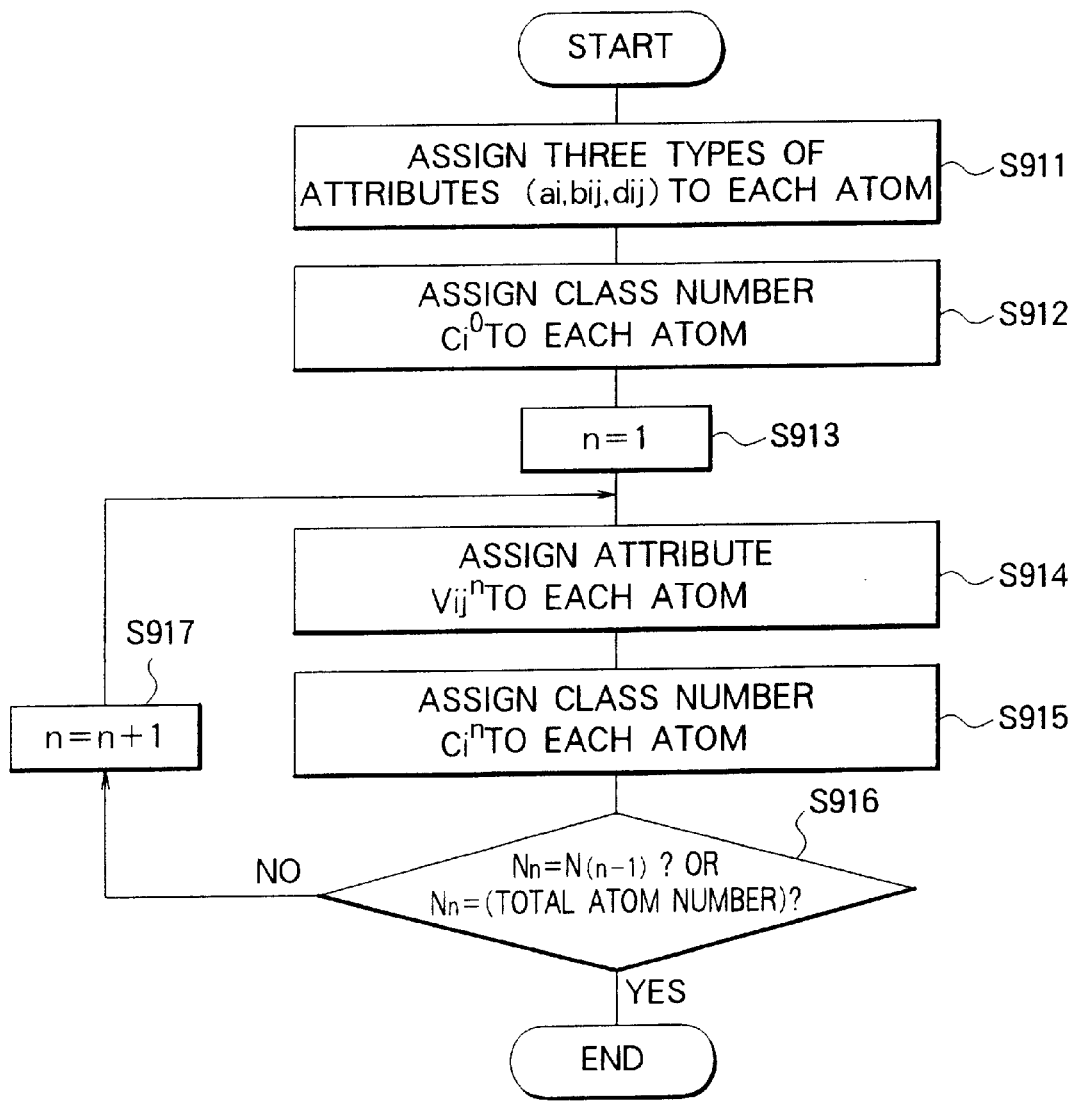
FIG. 21 is a flowchart to show the schematic process of the constituent atom classification routine.

As shown in the flowchart of FIG. 21, first, three types of attributes ($a_i$, $b_{ij}$, $d_{ij}$) are given to each of the atoms constituting the compound, based on the bond table 81 (S911). Here, attribute $a_i$ is a kind number of an atom of input number i (which is an atomic number in this example). Also, attribute $b_{ij}$ is the number (vector quantity) of bonds that are bonds adjacent to an atom of input number i and bonds with a kind number thereof (which is a type of bond in this example (1 for single bond, 2 for double bond, 3 for triple bond, 4 for aromatic bond, . . . )) being j. Further, attribute $d_{ij}$ is the number (vector quantity) of routes that can be traced from an atom of input number i via j bonds in the shortest path.

Next, the attributes ($a_i$, $b_{ij}$, $d_{ij}$) are arranged for each atom to obtain a 9-digit numeral string, class numbers $C_i^0$ are given to the atoms in the ascending order of the numeral strings from the smallest, and then the atoms are classified into a plurality of classes (S912). The class numbers $C_i^0$ given herein are zeroth-degree class numbers, and first-degree class numbers $C_i^1$, second-degree class numbers $C_i^2$, . . . are successively obtained in the loop process after S913.

Next, the degree n is set to 1 (S913). Then attribute $V_{ij}^1$ is given to each atom (S914). The attribute $V_{ij}^n$ is the number of atoms bonding to an atom of input number i and having a class number j in the degree n−1. Further, attributes ($a_i$, $b_{ij}$, $d_{ij}$, $V_{ij}^n$) are arranged for each atom, class numbers $C_i^n$ are given in the ascending order of the numeral strings from the smallest, and the atoms are classified into a plurality of classes (S915). Then it is checked whether the number $N_n$ of classes is equal to $N_{(n-1)}$, and the process is terminated if equal. Or, it is checked whether the number $N_n$ of classes is equal to the total atom number, and the process is terminated if equal (S916). When neither is equal, 1 is added to n and the processing returns to S914 (S917).

Next, the process in each step of constituent atom classification routine 91b will be explained in detail with an example of 3,5-dimethyl-2,3,4,5-tetrahydropyridine.

Figure 23:
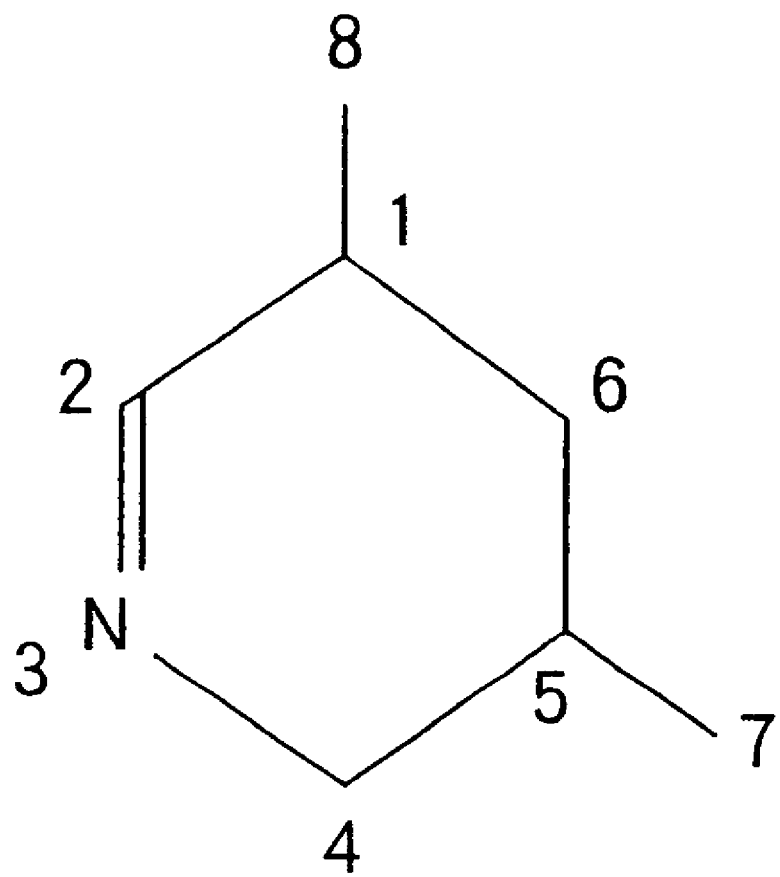
FIG. 23 is a drawing to show the relationship between each of the atoms constituting 3,5-dimethyl-2,3,4,5-tetrahydropyridine and an input number thereof.

First executed is the process of S911. Upon execution of this process the data as shown in FIGS. 22A and 22B has already been written in the bond table 81 and, based on each data written in the bond table 81, the three types of attributes ($a_i$, $b_{ij}$, $d_{ij}$) are given to each atom. Here, the input numbers recorded in this bond table 81 are arbitrary numbers given in the order of handwritten input of each atom, as shown in FIG. 23.

The attribute $a_i$ is gained as follows. As described previously, the attribute $a_i$ is a kind number of atom of input number i. Here, an element symbol of each atom is recorded in the bond table 81, and the kind numbers can be attained from these element symbols. Therefore, by reading an element symbol out of the bond table 81, the attribute $a_i$ corresponding to this element symbol can be obtained. As a result, we obtain $a_1$, $a_2$, $a_4$–$a_8$=6, and $a_3$=7.

The attribute $a_{ij}$ is obtained as follows. As discussed previously, the attribute $b_{ij}$ is the number of bonds adjoining an atom of input number i and having a bond kind number thereof being j. A type of bond of each atom is recorded in the bond table 81, and the attribute $b_{ij}$ can be attained by reading this type of bond out of the bond table 81. As a result, we obtain $b_{1j}$=(3, 0, 0, 0), $b_{2j}$=(1, 1, 0, 0), $b_{3j}$=(1, 1, 0, 0), $b_{4j}$=(2, 0, 0, 0), $b_{5j}$=(3, 0, 0, 0), $b_{6j}$=(2, 0, 0, 0), $b_{7j}$=(1, 0, 0, 0), and $b_{8j}$=(1, 0, 0, 0).

Figure 24A:
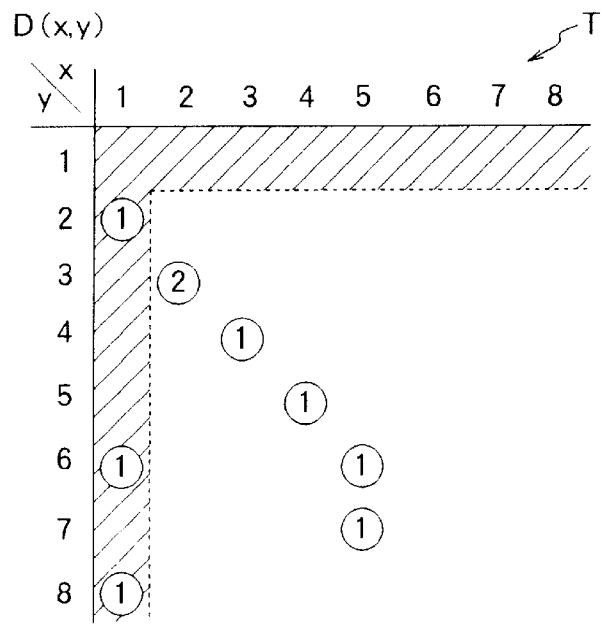
FIGS. 24A and 24B are drawings each showing the data contents of the reference table.
Figure 24B:
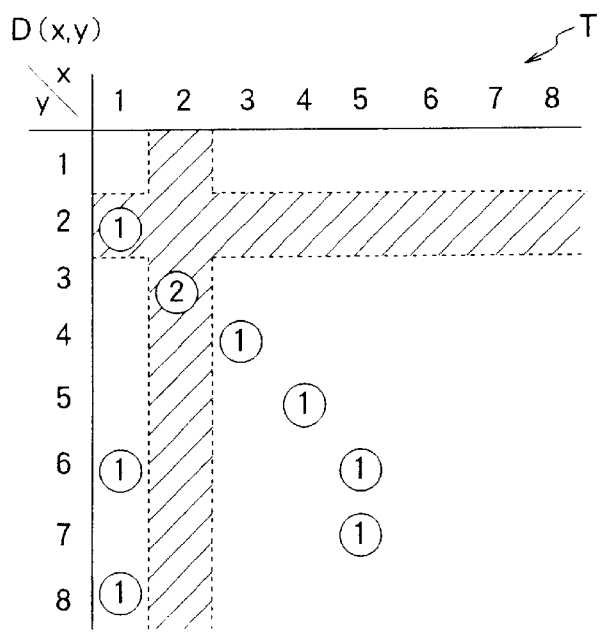

Specifically, the attribute $b_{ij}$ is obtained using the reference table T shown in FIGS. 24A and 24B. The reference table T is formed as a matrix D(x, y) indicating the bond relation between two atoms, and is prepared based on the data of bonding atom pair and type of bond in the bond table 81. Namely, a type of bond j is written in a matrix element indicated by each bonding atom pair, thus preparing the reference table T.

Extraction of attribute $b_{ij}$ using this reference table T is carried out as follows. First, matrix elements satisfying x=1 or y=1 (the matrix elements hatched in FIG. 24A) are checked among those of the reference table T to extract data (type of bond) j written in the matrix elements. As a result, we obtain D(1, 2)=1, D(1, 6)=1, and D(1, 8)=1. Since all data j of the three matrix elements thus obtained are 1, we obtain $b_{11}$=3. Since there is no matrix element with data j being two or more, we obtain $b_{12}$–$b_{14}$=0.

Next, matrix elements satisfying X=2 or Y=2 (the matrix elements hatched in FIG. 24B) are checked among those of the reference table T to extract data written in the matrix elements. As a result, we obtain D(1, 2)=1 and D(2, 3)=2. The data j of the matrix elements thus obtained is 1, 2, each of which is one, and thus, $b_{21}$=$b_{22}$=1. Since there is no matrix element with data j being 3 or more, we obtain $b_{23}$=$b_{24}$=0.

Through the same process for i=3–8, the attributes $b_{ij}$ (i=1–8, j=1–4) shown in FIG. 25 are attained.

Further, the attribute $d_{ij}$ is obtained as follows. As discussed previously, the attribute $d_{ij}$ is the number of routes that can be traced from an atom of input number i through j bonds in the shortest path. Specifically, describing it based on the molecular structure diagram of FIG. 23, routes that can be traced from the atom of input number 1 through one bond are three in total: (input number 1 to input number 2); (input number 1 to input number 6); (input number 1 to input number 8). Routes that can be traced from the atom of input 1 through two bonds are two in total: (input 1 to input number 2 to input number 3); (input 1 to input number 6 to input number 5).

Further, routes that can be traced from the atom of input 1 through three bonds in the shortest path are three in total: (input 1 to input number 2 to input number 3 to input number 4); (input 1 to input number 6 to input number 5 to input number 4); (input 1 to input number 6 to input number 5 to input number 7). Moreover, there is no route tracing from the atom of input 1 through four bonds in the shortest path. From the results of the above processes, we obtain $d_{ij}=(3, 2, 3, 0)$.

Through the same processes, we obtain $d_{2j}=(2, 3, 2, 2)$, $d_{3j}=(2, 2, 4, 0)$, $d_{4j}=(2, 3, 2, 2)$, $d_{5j}=(3, 2, 3, 0)$, $d_{6j}=(2, 4, 2, 0)$, $d_{7j}=(1, 2, 2, 3)$, and $d_{8j}=(1, 2, 2, 3)$.

Specifically, the attributes $d_{ij}$ are obtained referring to the reference table T in the same manner as the attributes $b_{ij}$. This extraction of attributes $d_{ij}$ referring to the reference table T is carried out in the order of i=1, i=2, . . . . The attribute $d_{1j}$ (i=1) is first extracted.

Figure 26A:
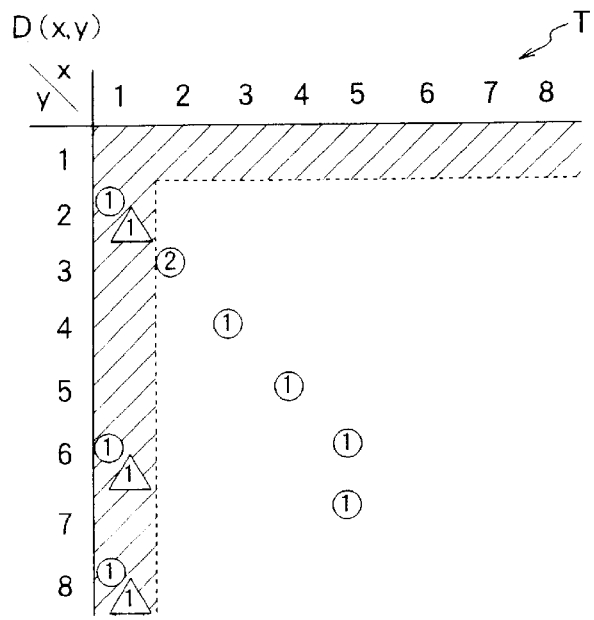
FIGS. 26A and 26B are drawings each showing the data contents of the reference table.

The extraction of attribute $d_{1j}$ (i=1) is to check matrix elements satisfying X=1 or Y=1 (the matrix elements hatched in FIG. 26A) among those of the reference table T and to extract a matrix element in which data is written. Then, 1 is written as a bond path number in each matrix element extracted. As a result, the bond path 1 is written in D(1, 2), D(1, 6), and D(1, 8) (each bond path number is shown as enclosed in a triangle in FIG. 26A).

Figure 26B:
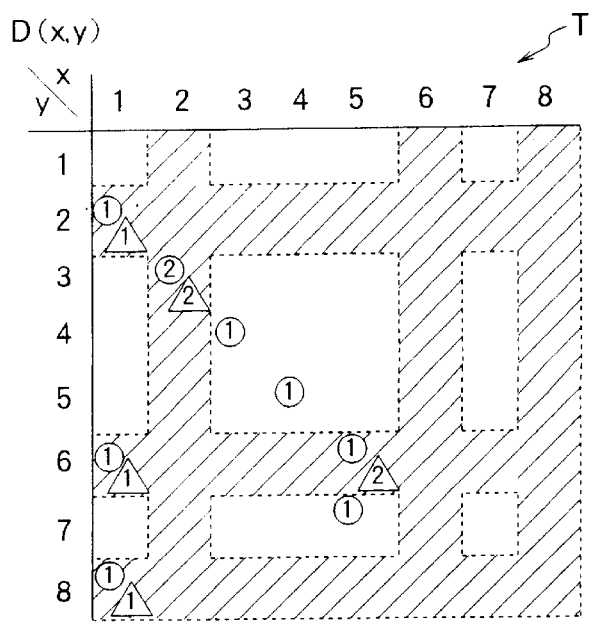

Next extracted are suffixes S=(1, 2), (1, 6), (1, 8) of the matrix elements each having the bond path number 1 written. From these suffixes S, 1, which has been used in the previous extraction process, is excluded, thus obtaining S=2, 6, 8. Based. on S=2, 6, 8 thus obtained, matrix elements satisfying X=2, 6, 8 or Y=2, 6, 8 (the matrix elements hatched in FIG. 26B) are checked to extract a matrix element with data written therein and with no bond path number written yet. Then, 2 is written as a bond path number in each matrix element extracted. As a result, the bond path number 2 is written in D(2, 3) and D(5, 6).

Figure 27:
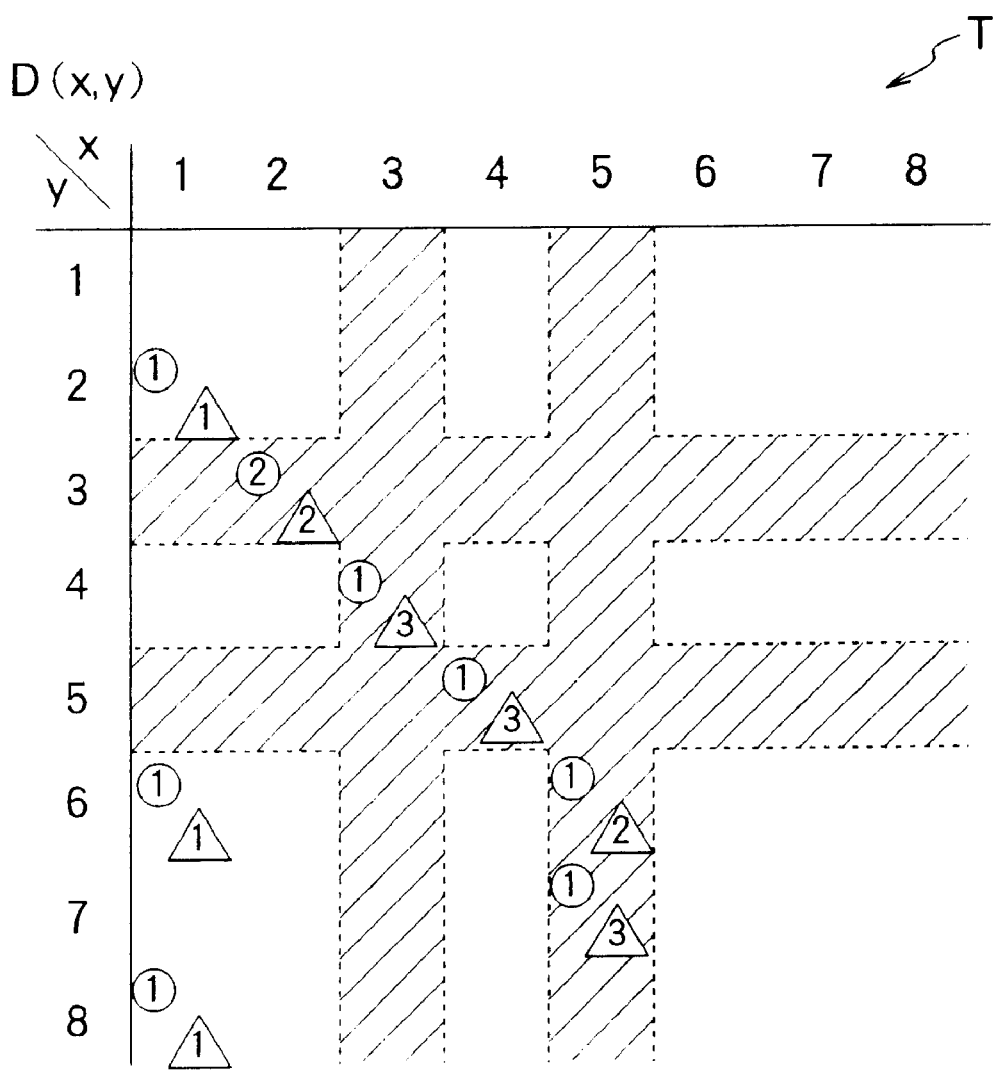
FIG. 27 is a drawing to show the data contents of the reference table.

Further, extracted are suffixes S=(2, 3), (5, 6) of the matrix elements with the bond path number 2 written therein. From these suffixes S, 2, 6, having already been used in the previous extraction process, are excluded, thus obtaining S=3, 5. Based on S=3, 5 thus obtained, matrix elements satisfying X=3, 5 or Y=3, 5 (the matrix elements hatched in FIG. 27) are checked to extract a matrix element with data written therein and without no bond path number written yet. Then, 3 is written as a bond path number in each matrix element extracted. As a result, the bond path number 3 is written in D(3, 4), D(4, 5), and D(5, 7).

Through the above processes, the bond path numbers are written in the all matrix elements. As a result, there are three matrix elements with the bond path number 1, two matrix elements with the bond path number 2, three matrix elements with the bond path number 3, and no matrix element with the bond path number 4, thus attaining $d_{1j}=(3, 2, 3, 0)$.

Figure 28A:
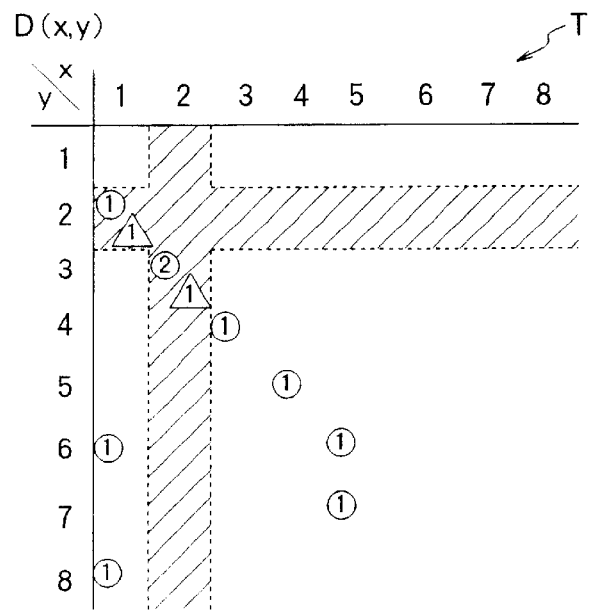
FIGS. 28A and 28B are drawings each showing the data contents of the reference table.

Next, the attribute $d_{2j}$ (i=2) is extracted. The extraction of attribute $d_{2j}$ (i=2) is to check matrix elements satisfying X=2 or Y=2 (the matrix elements hatched in FIG. 28A) among those of the reference table T and to extract a matrix element with data written therein. Then, 1 is written as a bond path number in each matrix element extracted. As a result, the bond path 1 is written in D(1, 2) and D(2, 3) (each bond path number is shown as enclosed in a triangle in FIG. 28A).

Figure 28B:
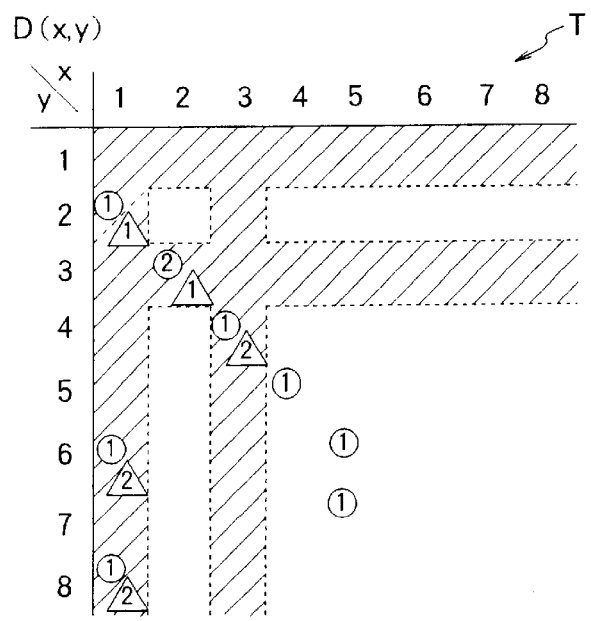

Next extracted are suffixes S=(1, 2), (2, 3) of matrix elements each with the bond path number 1 written therein. Excluding 2, having already been used in the previous extraction process, from these suffixes S, we obtain S=1, 3. Based on S=1, 3 thus obtained, matrix elements satisfying X=1, 3 or Y=1, 3 (the matrix elements hatched in FIG. 28B) are checked to extract a matrix element with data written therein and with no bond path number written yet. Then, 2 is written as a bond path number in each matrix element extracted. As a result, the bond path number 2 is written in D(1, 6), D(1, 8), and D(3, 4).

Figure 29A:
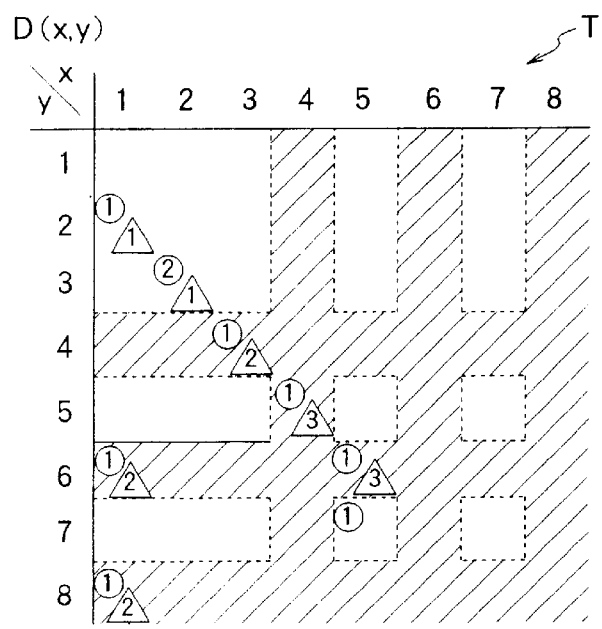
FIGS. 29A and 29B are drawings each showing the data contents of the reference table.

Further, extracted are suffixes S=(1, 6), (1, 8), (3, 4) of the matrix elements with the bond path number 2 written therein. Excluding 1, 3, having already been used in the previous extraction process, from these suffixes S, we obtain S=4, 6, 8. Based on S=4, 6, 8 thus obtained, matrix elements satisfying X=4, 6, 8 or Y=4, 6, 8 (the matrix elements hatched in FIG. 29A) are checked to extract a matrix element with data written therein and with no bond path number written yet. Then, 3 is written as a bond path number in each matrix element extracted. As a result, the bond path number 3 is written in D(4, 5) and D(5, 6).

Figure 29B:
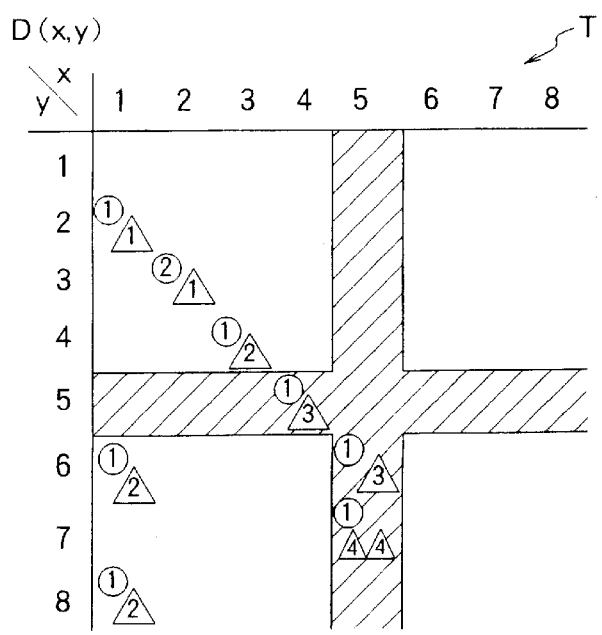

Furthermore, extracted are suffixes S=(4, 5), (5, 6) of the matrix elements with the bond path number 3 written therein. Excluding 4, 6, having already been used in the previous extraction process, from these suffixes S, we obtain S=5, 5 (which means that S=5 is doubly applied). Based on S=5, 5 thus obtained, matrix elements satisfying X=5 or Y=5 (the matrix elements hatched in FIG. 29B) are checked to extract a matrix element with data written therein and with no bond path number written therein yet. Then, 4 is written as a bond path number in each matrix element extracted. As a result, two of the bond path number 4 are written in D(5, 7).

Through the above processes, the bond path numbers are written in the all matrix elements. As a result, there are two matrix elements with the bond path number 1, three matrix elements with the bond path number 2, two matrix elements with the bond path number 3, and two matrix elements with the bond path number 4, thus attaining $d_{1j}=(2, 3, 2, 2)$.

By the same processes for i=3 to 8, $d_{ij}$ (i=1 to 8, j=1 to 4) shown in FIG. 25 are attained. The process of S911 as described above gave the three types of attributes ($a_i$, $b_{ij}$, $d_{ij}$) to each of the atoms constituting 3,5-dimethyl-2,3,4,5-tetrahydropyridine.

Next executed is the process of S912. As described above, at S912 the attributes ($a_i$, $b_{ij}$, $d_{ij}$) for each atom are arranged in a 9-digit numeral string, and class numbers $C_i^0$ are given to the atoms in the ascending order of the numeral strings from the smallest, thus classifying the atoms into a plurality of classes. The class numbers $C_i^0$ given herein are zeroth-degree class numbers.

Describing the process of S912 specifically, the numeral string of the atom of input 1 is "630003230" and the numeral string of the atom of input number 2 is "611002322". Following it in order, we obtain "711002240", "620002322", "630003230", "620002420", "610001223", and "610001223".

Figure 30A:
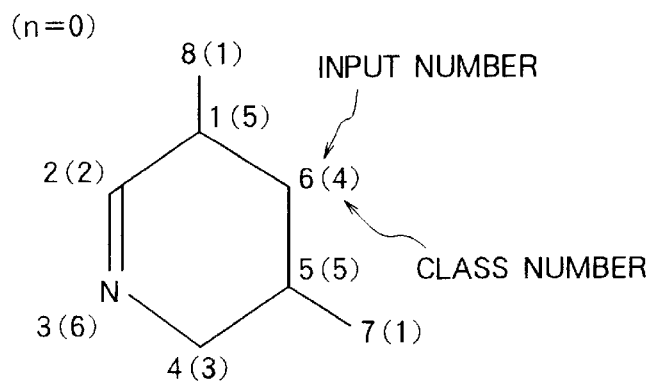
FIGS. 30A–30C are drawings to show the relationship between each of the atoms constituting 3,5-dimethyl-2,3,4,5-tetrahydropyridine and a class number thereof.

As a result, the numeral strings of the atoms of input numbers 7 and 8 are minimum, so that the class number $C_7^0=C_8^0=1$ is given to these atoms. Similarly, the class number $C_2^0=2$ is given to the atom of input number 2, and the class number $C_4^0=3$ to the atom of input number 4. Also, the class number $C_6^0=4$ is given to the atom of input number 6, and the class number $C_1^0=C_5^0=5$ to the atoms of input numbers 1 and 5. Further, the class number $C_3^0=6$ is given to the atom of input number 3 (see FIG. 30A). The atoms are classified into the six classes in this manner, and thus the number No of classes is 6.

Next, the process of S913 is carried out to set the degree n to 1.

Figure 30B:
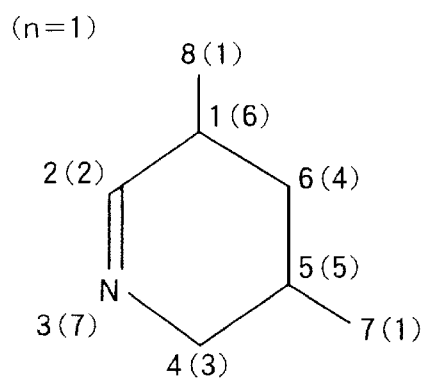

Further, the process of S914 is carried cut. As described previously, the attribute $V_{ij}^{1(n-1)}$ is given to each atom at S914. Here, the attribute $V_{ij}^n$ is the number of atoms bonding to an atom of input number i and having a class number of j. Namely, describing it based on the molecular structure diagram of FIG. 30B, input numbers of atoms bonding to the atom of input number 1 are 2, 6, 8, and the class numbers of these atoms are $C_2^0=2$, $C_6^0=4$, and $C_8^0=1$. As a result, 1 is written in the attribute $V_{1j}^1$ of j=1, 2, 4, thus obtaining $V_{1j}^1=(1, 1, 0, 1, 0, 0)$.

Also, input numbers of atoms bonding to the atom of input number 2 are 1, 3, and the class numbers of these atoms are $C_1^0=5$ and $C_3^0=6$. As a result, 1 is written in the attribute $V_{2j}^1$ of j=5, 6, thus obtaining $V_{2j}^1=(0, 0, 0, 0, 1, 1)$. The same processes for the atoms of input numbers 3 to 8 will result in obtaining $V_{3j}^1=(0, 1, 1, 0, 0, 0)$, $V_{4j}^1=(0, 0, 0, 1, 1, 0)$, $V_{5j}^1=(1, 0, 1, 1, 0, 0)$, $V_{6j}^1=(0, 0, 0, 0, 2, 0)$, $V_{7j}^1=(0, 0, 0, 0, 1, 0)$, and $V_{8j}^1=(0, 0, 0, 0, 1, 0)$.

Specifically, the attributes $V_{ij}^0$ are obtained using the reference table T shown in FIGS. 24A and 24B. Extraction of attributes $V_{ij}^1$ using this reference table T is carried out in the order of i=1, i=2, . . . . First, attribute $V_{1j}^1$ (i=1) is extracted. Extraction of attribute $V_{1j}^1$ (i=1) is to check the matrix elements satisfying x=1 or y=1 (the matrix elements hatched in FIG. 24A) among the matrix elements of the reference table T and to extract suffixes S=(1, 2), (1, 6), (1, 8) of the matrix elements with data written therein. Excluding i=1 from these suffixes S, we obtain S=2, 6, 8. Substituting the values of S thus obtained into the class number $C_i^0$, we obtain $C_2^0=2$, $C_6^0=4$, and $C_8^0=1$. Then, 1 is written in the attribute $V_{1j}^1$ of j=1, 2, 4, thus obtaining $V_{1j}^1=(1, 1, 0, 1, 0, 0)$.

Next, the attribute $V_{2j}^1$ (i=2) is extracted. The extraction of attribute $V_{2j}^1$ (i=2) is to check the matrix elements satisfying X=2 or Y=2 (the matrix elements hatched in FIG. 24B) among the matrix elements of the reference table T and to extract suffixes S=(1, 2), (2, 3) of the matrix elements with data written therein. Excluding i=2 from these suffixes S, we obtain S=1, 3. The values of S thus obtained are substituted into the class number $C_i^0$, thus obtaining $C_1^0=5$ and $C_3^0=6$. Then 1 is written in the attribute $V_{2j}^1$ of j=5, 6, thus attaining $V_{2j}^1=(0, 0, 0, 0, 1, 1)$.

The same processes for i=3 to 8 will result in obtaining the attributes $V_{ij}^1$ (i=1 to 8, j=1 to 6) shown in FIG. 31.

Next executed is the process of S915. As described previously, at S915 the attributes ($C_i^{n-1}$, $V_{ij}^n$) are arranged for each atom, and class numbers $C_i^n$ are given to the atoms in the ascending order of the numeral strings from the smallest, thus classifying the atoms into a plurality of classes.

Specifically, the numeral string of the atom of input number 1 is "5110100" and the numeral string of the atom of input number 2 is "2000011". Following it in order, we obtain "6011000", "3000110", "5101100", "4000020", "1000010", and "1000010".

As a result, the numeral strings of the atoms of input numbers 7 and 8 are minimum, and the class number $C_7^1=C_8^1=1$ is given to these atoms. Similarly, the class number $C_2^1=2$ is given to the atom of input number 2, and the class number $C_4^1=3$ to the atom of input number 4. Further, the class number $C_6^1=4$ is given to the atom of input number 6, and the class number $C_5^1=5$ to the atom of input number 5. Furthermore, the class number $C_1^1=6$ is given to the atom of input number 1, and the class number $C_3^1=7$ to the atom of input number 3. The atoms are classified into the seven classes in this manner, and the number $N_1$ of classes is 7.

The process of S916 is next executed to check whether the number $N_n$ of classes is equal to $N_{(n-1)}$, and the process is terminated if equal. Also, whether the number $N_n$ of classes is equal to the total atom number is checked, and the process is terminated if equal. Here, since the number $N_1$ of classes is 7 and the number $N_0$ of classes is 6, $N_1$ is not equal to $N_0$. Also, since the total number of atoms is 8, the number $N_1$ of classes is not equal to the total number of atoms. Since neither is equal in this way, the process of S917 is executed to set n to 2.

Further, the process returns to S914 to give the attribute $V_{ij}^2$ to each atom. As a result, as shown in FIG. 32, we obtain $V_{1j}^2=(1, 1, 0, 1, 0, 0, 0)$, $V_{2j}^2=(0, 0, 0, 0, 0, 1, 1)$, $V_{3j}^2=(0, 1, 1, 0, 0, 0, 0)$, $V_{4j}^2=(0, 0, 0, 0, 1, 0, 1)$, $V_{5j}^2=(1, 0, 1, 1, 0, 0, 0)$, $V_{6j}^2=(0, 0, 0, 0, 1, 1, 0)$, $V_{7j}^2=(0, 0, 0, 0, 1, 0, 0)$, and $V_{8j}^2=(0, 0, 0, 0, 0, 1, 0)$.

Figure 30C:
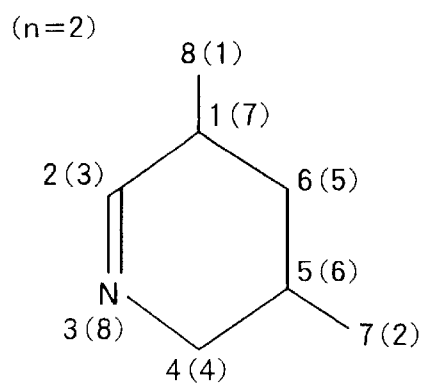

Then the process of S915 is carried out to give the class number $C_i^2$ to each atom. As a result, as shown in FIG. 30C, we obtain $C_1^2=7$, $C_2^2=3$, $C_3^2=8$, $C_4^2=4$, $C_5^2=6$, $C_6^2=5$, $C_7^2=2$, and $C_8^2=1$. The atoms are classified into the eight classes in this manner, and the number $N_2$ of classes is 8. Since the number of classes $N_2=8$ is equal to the total number of atoms, the process is terminated by determination at S916.

Figure 33:
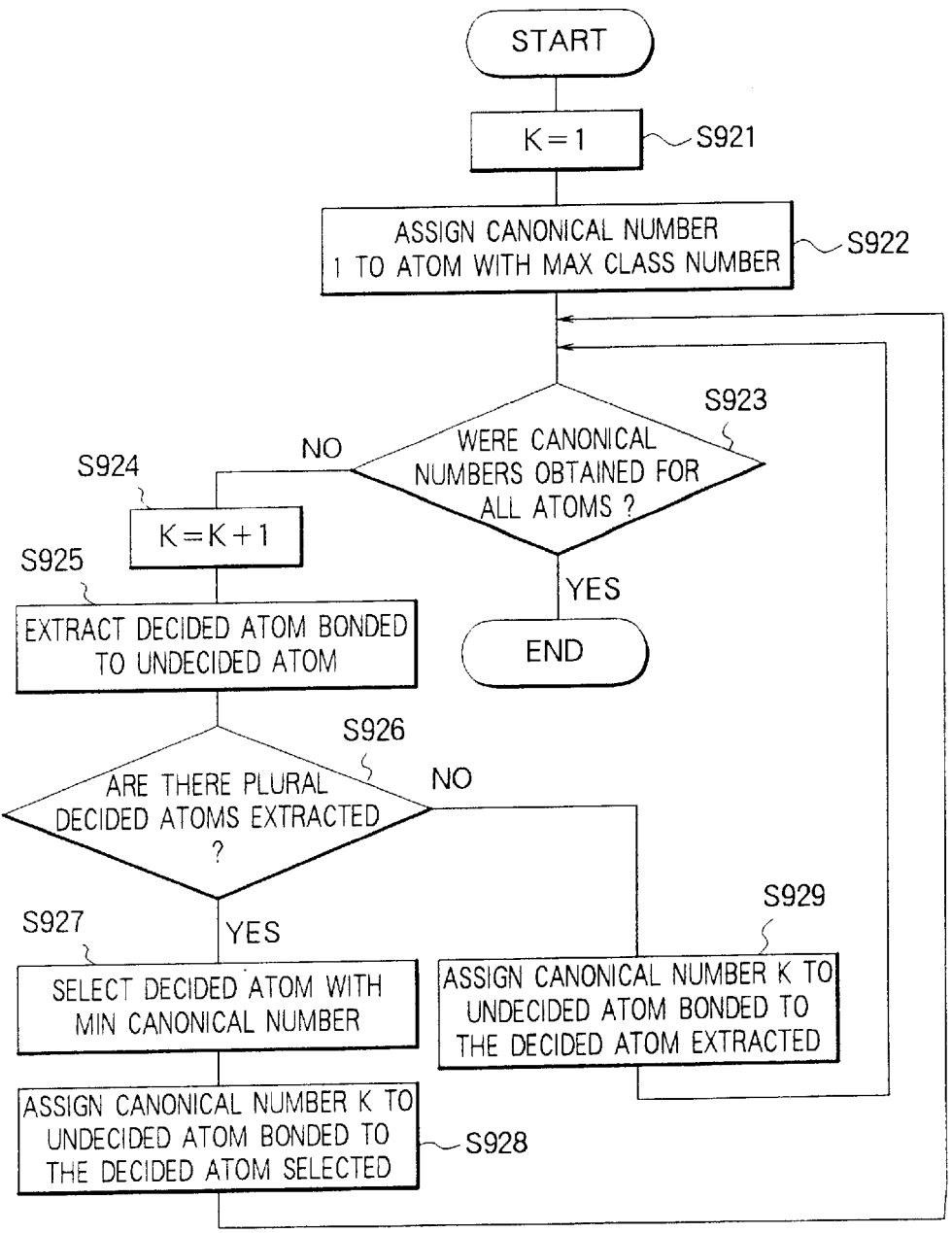
FIG. 33 is a flowchart to show the schematic process of a canonical number assignment routine.

Next explained using the flowchart of FIG. 33 is the process of canonical number assignment routine 91c called at S920 of FIG. 20. Here, a canonical number is a number of each atom uniquely determined depending upon the structure of a compound. Namely, an input number given by handwritten input of molecular structure diagram is an arbitrary number changing depending upon change of input order. In contrast with it, the canonical data 82 is unique data depending only on the structure of compound. Therefore, it is difficult to directly make the unique canonical data 82 from the arbitrary input numbers. Thus, the canonical data preparation program 91 enables smooth preparation of canonical data 82 by converting the input numbers once into canonical numbers and preparing the canonical data 82 based on the unique canonical numbers.

In the process of canonical number assignment routine 91c, first, 1 is given to variable k (S921). Next, the final class numbers $C_i^f$ obtained in the constituent atom classification routine 91b are checked, and a canonical number k (k=1 herein) is given to the atom with the maximum class number (S922). If there are a plurality of maximum atoms, an arbitrary atom is selected out of these atoms, and the canonical number k is given to this atom. After canonical numbers have been assigned to all atoms, then the process is terminated (S923).

Next, 1 is added to the variable k (S924), and, out of the atoms for each of which the canonical number is decided (which will be referred to as decided atoms), a decided atom to which an atom for which a canonical number is not decided (which will be referred to as an undecided atom) bonds is extracted (S925). Then whether there are plural decided atoms extracted is determined (S926), and if there are plural decided atoms extracted, a decided atom with the minimum canonical number is selected out of these decided atoms (S927). Then an undecided atom with the maximum class number $C_i^f$ is extracted out of the undecided atoms bonding to the decided atoms thus selected, and the canonical number of this undecided atom is determined as k (S928). If there are plural decided atoms with the maximum class number $C_i^f$, an arbitrary one is selected out of these decided atoms.

When one decided atom is determined at S926, an undecided atom with the maximum class number $C_i^f$ is selected out of the undecided atoms bonding to this decided atom and is given the canonical number k (S929). After completion of the processes of S928 and S929 the processing returns to S923, and the loop of S923 to S929 is repeated until the canonical numbers are assigned to the all atoms.

Next, the process of canonical number assignment routine 91c is explained with a specific example using 3,5-dimethyl-2,3,4,5-tetrahydropyridine. First, 1 is given to the variable k in the process of S921 and then the process of S922 is carried out. In the process of S922, since the atom of input number 3 has maximum $C_3^f=8$, the canonical number k=1 is given to the atom of input number 3. Next, the process of S924 is executed to change the variable k to 2, and the process of S925 is then carried out to extract the atom of input number 3 as a decided atom.

Since there is one decided atom thus extracted, the process of S929 is then carried out. Since undecided atoms bonding to the atom of input number 3 are the atoms of input numbers 2, 4, an atom with the maximum class number $C_i^f$ is selected out of these atoms. Namely, the class number of the atom of input number 2 is $C_2^f=3$, and the class number of the atom of input number 4 is $C_4^f=4$. Thus, the atom of input number 4 is selected, and the canonical number k=2 is given to this atom.

Next, the flow returns to the process of S924 to change the variable k to 3, and the process of S925 is carried out to extract the atoms of input numbers 3, 4 as decided atoms. Since there are plural decided atoms thus extracted, then the process of S927 is carried out to select an atom with the minimum canonical number out of the decided atoms thus extracted. Namely, the canonical number of the atom of input number 3 is 1 and the canonical number of the atom of input number 4 is 2. Thus, the atom of input number 3 is selected. Then the process of S928 is carried out to give the canonical number k=3 to the atom of input number 2 bonding to the atom of input number 3.

Further, the flow returns to the process of S924 to change the variable k to 4, and the process of S925 is carried out to extract the atoms of input numbers 2, 4 as decided atoms. Since there are plural decided atoms thus extracted, then the process of S927 is carried out to select an atom with the minimum canonical number out of the decided atoms thus extracted. Namely, the canonical number of the atom of input number 2 is 3 and the canonical number of the atom of input number 4 is 2. Thus, the atom of input number 4 is selected. Then the process of S928 is carried out to give the canonical number k=4 to the atom of input number 5 bonding to the atom of input number 4.

Repeating the same processes, the canonical number 5 is assigned to the atom of input number 1 and the canonical number 6 to the atom of input number 6, respectively. Also, the canonical number 7 is given to the atom of input number 7 and the canonical number 8 to the atom of input number 8, respectively.

Figure 34:
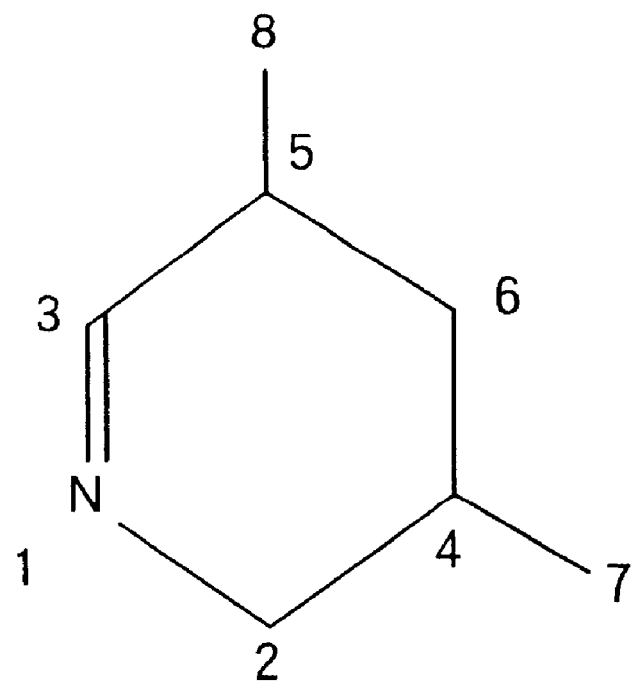
FIG. 34 is a drawing to show the relationship between each of the atoms each constituting 3,5-dimethyl-2,3,4,5-tetrahydropyridine and a canonical number thereof.

After that, the process of S923 is carried out, and because the canonical numbers are obtained for the all atoms at this stage, the process is terminated. As a result, the canonical numbers as shown in FIG. 34 are obtained.

Figure 35:
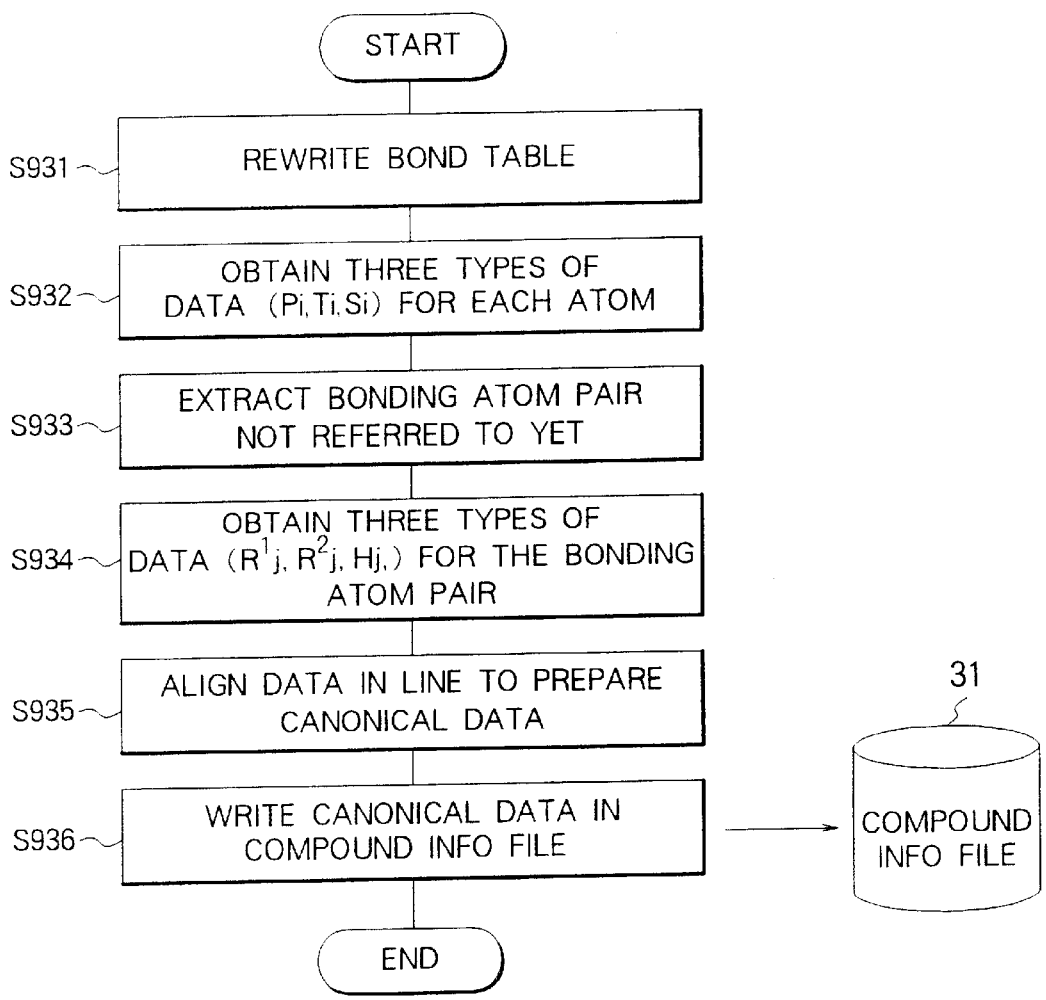
FIG. 35 is a flowchart to show the schematic process of a canonical data preparation routine.

Next explained using the flowchart of FIG. 35 is the process of canonical data preparation routine 91d called at S930. In this process, first, the input numbers are replaced by the canonical numbers, as shown in FIGS. 36A and 36B, to rewrite the bond table 81 (S931). Then, based on this bond table 81, three types of data ($P_i$, $T_i$, $S_i$) is obtained for each atom (S932). Here, $P_i$ is a canonical number of an atom bonding to an atom of canonical number i (i>1) and having a minimum number. Also, $T_i$ is a symbol of type of bond between an atom of canonical number i (i>1) and an atom of canonical number $P_i$ (— for single bond, = for double bond, # for triple bond, % for aromatic bond, and so on in this example). Further, $S_i$ is a symbol for a type of atom of canonical number i (i>0) (which is an element number in this case).

Specifically, first, an element number of the atom of canonical 1 is checked with reference to the atomic table 81g. This will result in obtaining $S_1$="N". Next, which atom bonds to the atom of canonical number 2 is checked referring to the atomic pair table 81h. As a result, the atoms of canonical numbers 1, 4 are obtained. Since the minimum canonical number is 1 out of these atoms, $P_2=1$. Since the bond between the atom of canonical number 2 and the atom of canonical number 1 is a single bond, $T_2$="—". Further, $S_2$="C" is obtained referring to the atomic table 81g.

Next, which atom bonds to the atom of canonical number 3 is checked referring to the atomic pair table 81h. As a result, the atoms of canonical numbers 1, 5 are attained. Since the minimum canonical number is 1 among these atoms, $P_3=1$. Since the bond between the atom of canonical number 3 and the atom of canonical number 1 is a double bond, $T_3$="=". Further, referring to the atomic table 81g, $S_3$="C" is obtained. The same processes to follow obtain $P_4=2$, $P_6=3$, $P_6=4$, $P_7=4$, $P_8=5$, $T_4$ to $T_8$="—", and $S_4$ to $S_8$="C".

Next extracted is a bonding atom pair which was not referred to upon obtaining Ti in the process of S932 (S933). This process is carried out referring to the atomic pair table 81h. This will result in extracting a bonding atom pair of the atom of canonical number 5 and the atom of canonical number 6. Then three types of data ($R^1_j$, $R^2_j$, $H_j$) are obtained for the bonding atom pair thus extracted (S934). Here, $R^1_j$, $R^2_j$ are canonical numbers of two atoms constituting the bond. Also, $H_j$ is a symbol for a type of the bond (the same symbols as $T_i$ are used in this example). It is assumed that $R^1_j$ and $R^2_j$ satisfy the relation of $R^1_j > R^2_j$. With another bonding atom pair ($R^1_k$, $R^2_k$), they are supposed to satisfy the relation of $R^1_j \leq R^1_k$ or the relation of $R^1_j = R^1_k$ and $R^2_j < R^2_k$.

The above processes prepared the canonical tree structure data shown in FIG. 37.

Next, the data obtained in the processes of S932 and S934 is aligned in line, thus preparing canonical data (S935). Namely, defining a delimiter F different from the symbols for the types of atom and for the types of bond, the data obtained in the processes of S932 and S934 is aligned as follows.

$S_1$, $P_2$, $T_2$, $S_2$, $P_3$, $T_3$, $S_3$, $P_4$, $T_4$, $S_4$, . . . , $P_N$, $T_N$, $S_N$, F, $R^1_1$, $H_1$, $R^2_1$, F, $R^1_2$, $H_2$, $R^2_2$, . . . , F, $R^1_M$, $H_M$, $R^2_M$, F

Here, N is the total number of atoms and M is the total number of bonding atom pairs extracted at S934.

The data string thus obtained is canonical data uniquely corresponding to the structure of compound. Specifically, using "/" as the delimiter F, the obtained data is aligned in the predetermined order as follows.

"N1=C1=C2-C3-C4-C4-C5-C/5-6/"

Then this canonical data is written into the compound information file 31 to be saved therein (S936). After that, the process is terminated.

The canonical data preparation means and method according to the present invention are not limited to the above embodiment, but may be modified within the scope not departing from the spirit of the present invention, for example as follows.

(1) The above embodiment used the data string including the symbols Si for the types of atom as the canonical data, but the symbol for the type of the atom with the highest frequency of occurrence (which is normally C for carbon) may be excluded from the data string. Namely, omitting the symbol for carbon C out of the above canonical data, we obtain the following.

"N1-1=2-3-4-4-5-/5-6/"

Shortening the data string in this manner can reduce the quantity of data written into the compound information file 31.

(2) The following processes may be added to the canonical number assignment routine 91c in the case of a plurality of undecided atoms with the maximum class number $C_i^f$ being selected in the process of S929.

(a) If an undecided atom with the maximum class number $C_i^f$ does not belong to a cyclic structure portion, an arbitrary undecided atom is selected out of the plurality of undecided atoms and k is assigned as a canonical number of this undecided atom. After that, the processing returns to S923.

(b) If an undecided atom with the maximum class number $C_i^f$ belongs to a cyclic structure portion, as to a structure obtained by cutting bonds between the undecided atoms selected at S929 (hereinafter referred to as candidate atoms) and decided atoms bonding to these candidate atoms, the following vector quantity is defined for each candidate atom.

$m_{ik}$: the minimum bond number between candidate atom i and atom with canonical number k.

The order of priority is preliminarily determined as to this attribute, and an atom i with the highest priority order is selected and k is assigned as a canonical number of the atom. After that, the process returns to S923.

Here, criteria of judgment of priority order in attribute values of atoms are as follows. First, non-vector quantities depend upon the degree of priority order. As for vector quantities, when elements of two vectors i, k are attributes $V_{ij}$, $V_{kj}$, the magnitude at minimum j among the elements with $V_{ij} \neq V_{kj}$ is employed as a criterion of judgment of priority order. By employing such criteria of judgment, priority orders of the attributes $b_{ij}$, $d_{ij}$, $V_{ij}^n$, $m_{ij}$ can be determined. In the case of priority orders being determined by a plurality of attributes, priority orders are preliminarily determined among the attribute, and priority is given to judgment in an attribute with a higher priority order.

Figures 38A, 38B:
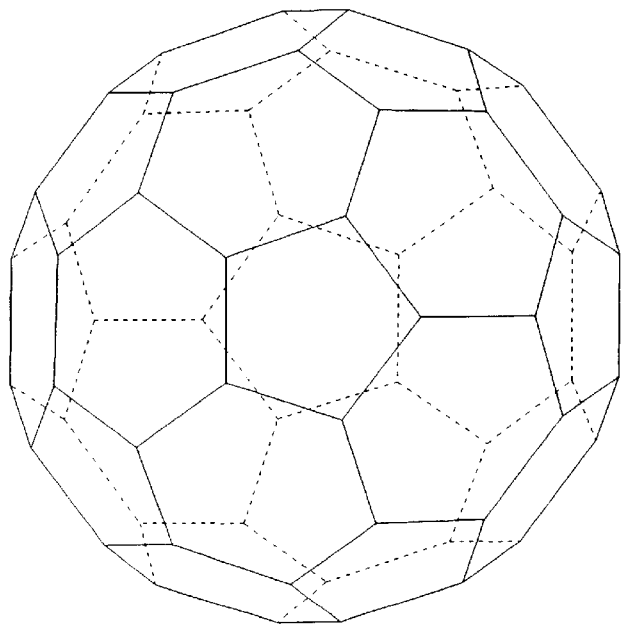
FIG. 38A is a molecular structure diagram of $C_{60}$.
FIG. 38B is canonical data thereof.

The above canonical data preparation method according to the present invention was used to obtain the canonical data of $C_{60}$ molecule shown in FIG. 38A, and the canonical data (FIG. 38B) for uniquely specifying the structure of the $C_{60}$ molecule was obtained just in 1.5 seconds. To the contrary, when the canonical data of the $C_{60}$ molecule was obtained using an information processing apparatus of same performance by the Morgan algorithm without intervention of the process for classifying the atoms into equivalent atoms, 550 seconds were needed to achieve the canonical data. Therefore, if the above canonical data preparation means and method according to the present invention are employed in the present invention, the speed of the biochemical information processing according to the present invention can be improved remarkably.

The foregoing explained the preferred embodiment of the biochemical information processing apparatus and method of the present invention, but it should be understood that the present invention is not limited to the above embodiment.

Figure 39:
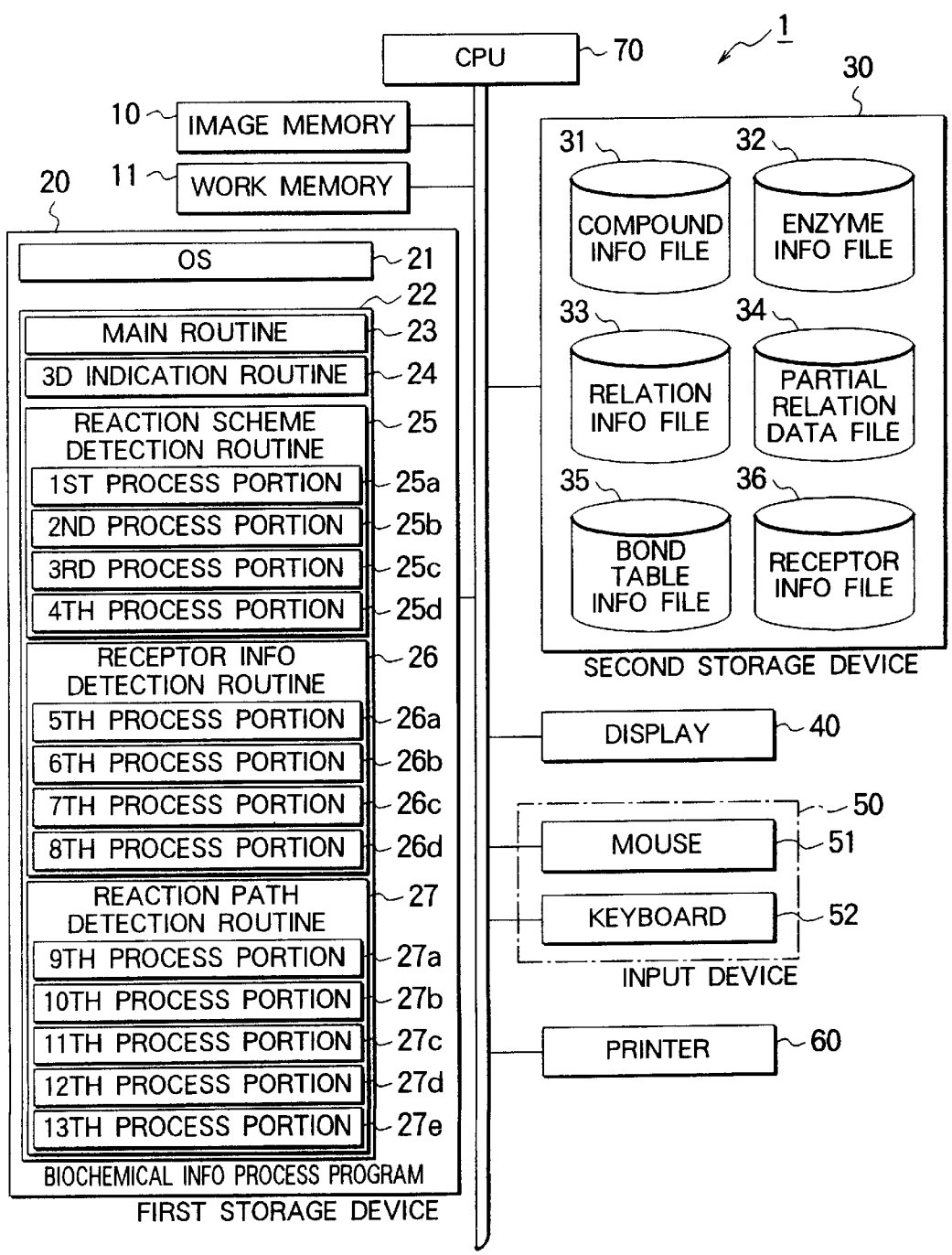
FIG. 39 is a block diagram to show the structure of another example of the biochemical information processing apparatus of the present invention.
Figure 40:
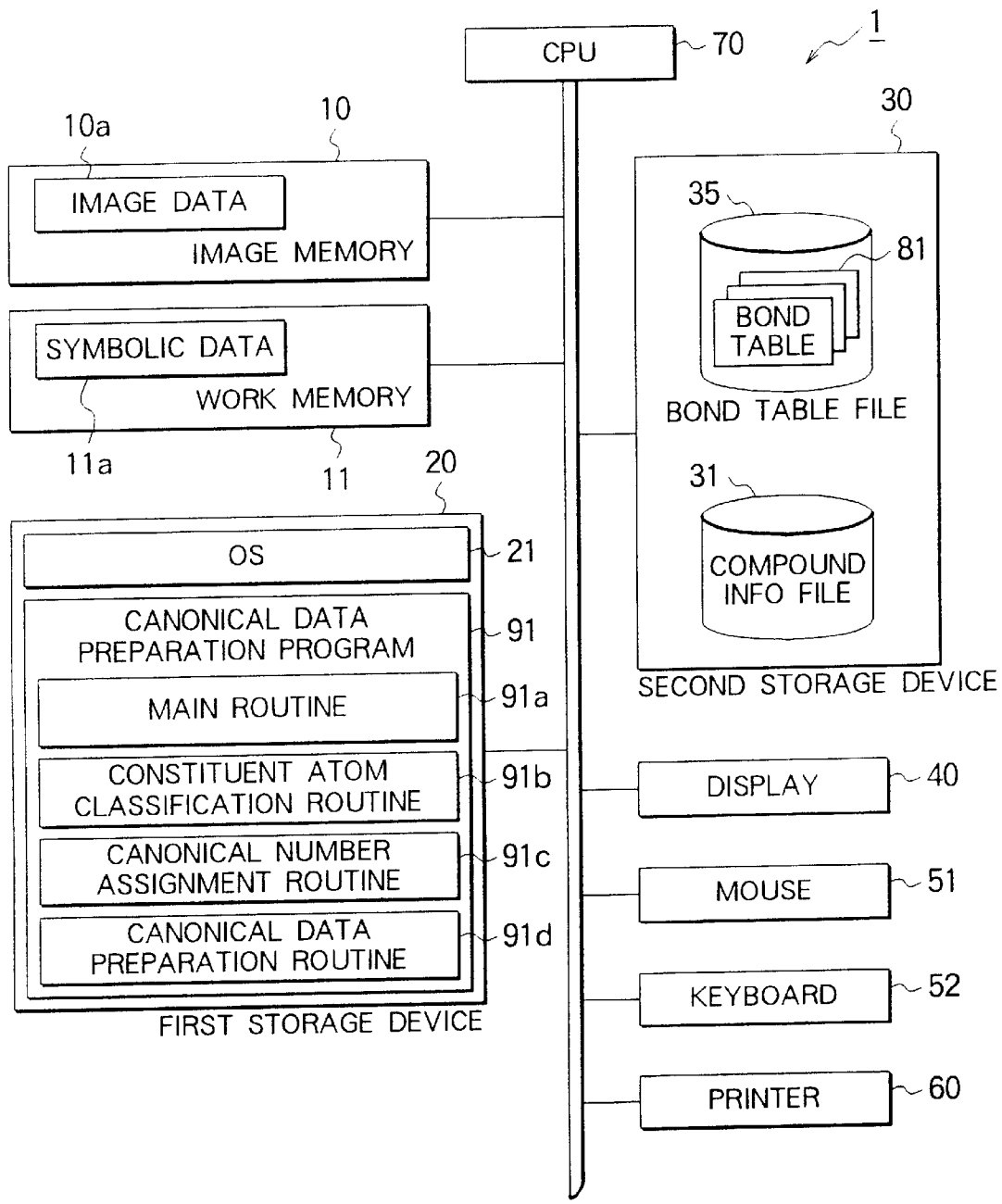
FIG. 40 is a block diagram to show the structure of an example of the canonical data preparing apparatus according to the present invention.

For example, the canonical data preparation means (the canonical data preparation program 91) according to the present invention does not have to be incorporated together with the other means (the reaction scheme detection program 25 etc.) in the first storage device in the biochemical information processing apparatus of the present invention, but, as shown in FIG. 39 and FIG. 40, the canonical data preparation means (the canonical data preparation program 91) according to the present invention and the other means (the reaction scheme detection program 25 etc.) may exist separately from each other in the first storage device 20.

Figure 41:
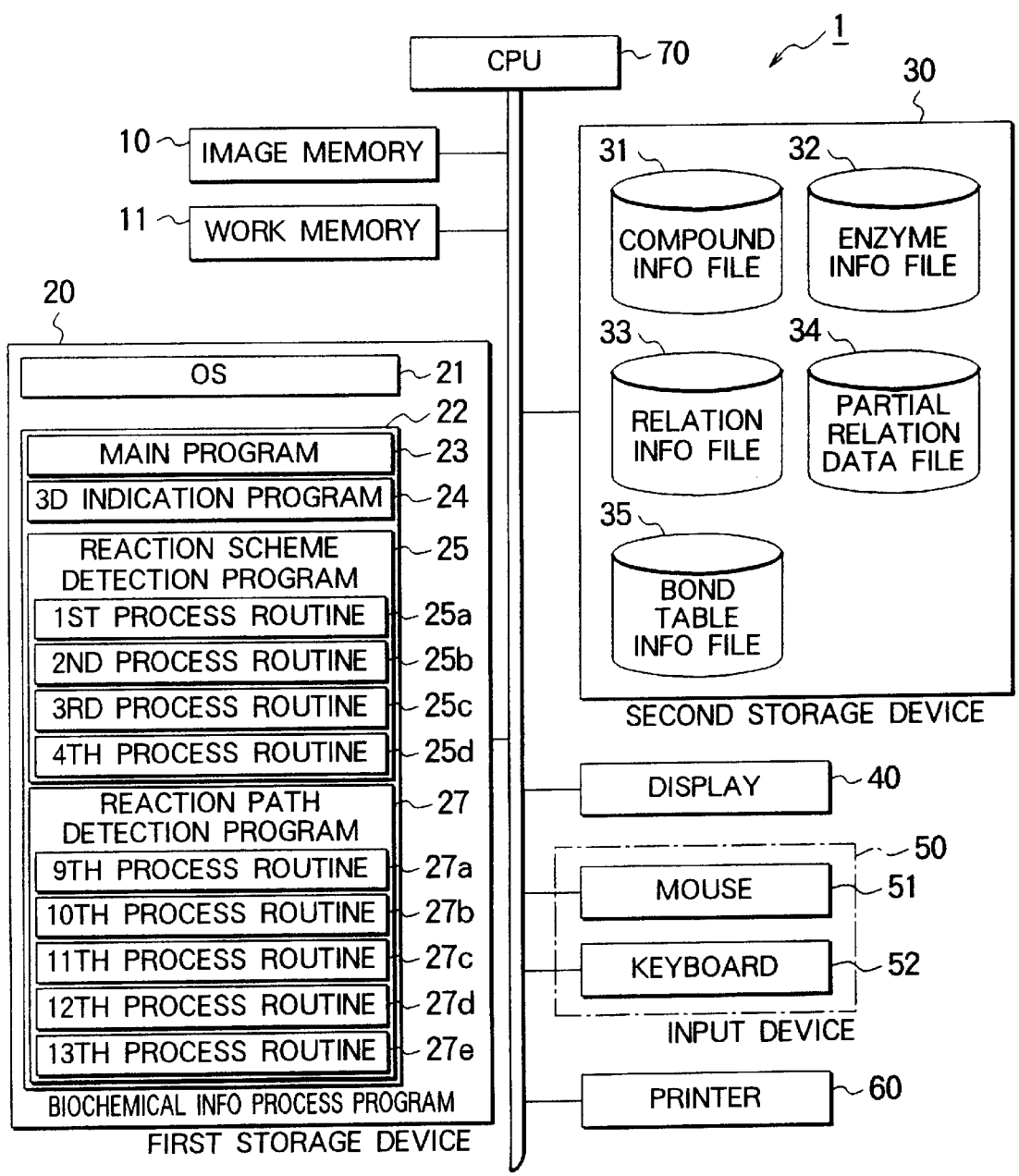
FIG. 41 is a block diagram to show the structure of still another example of the biochemical information processing apparatus of the present invention.
Figure 43:
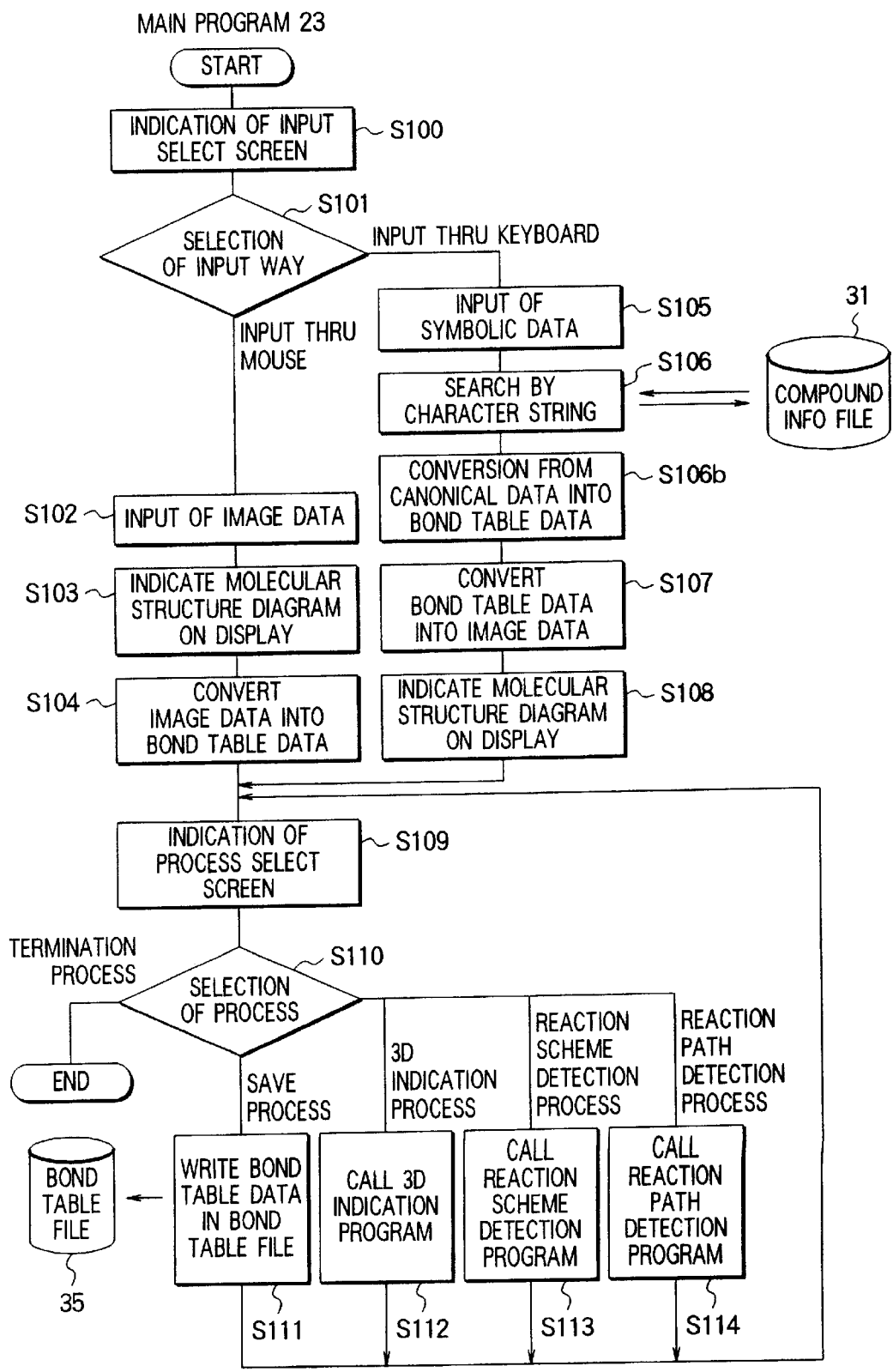
FIG. 43 is a flowchart to show the flow of process of another example of the main routine.

Also, the biochemical information processing apparatus of the present invention does not have to comprise all of the reaction scheme detection means (the reaction scheme detection program) 25, the receptor information detection means (the receptor information detection program) 26, and the reaction path detection means (the reaction path detection program) 27, but the apparatus may be arranged, for example, to be provided with the reaction scheme detection means (the reaction scheme detection program) 25 and the reaction path detection means (the reaction path detection program) 27, as shown in FIG. 41, or to be provided with only either one of them. In this case, the receptor information file 36 is not necessary, and the mutual relation between the compound numbers $C_1$–$C_7$ and the enzyme numbers $E_1$–$E_6$ described in the reaction path diagram of FIG. 2 is recorded in the relation information file 33 shown in FIG. 42. Describing in more detail, the enzyme numbers $E_1$–$E_6$ of the enzymes with each compound of compound number $C_1$–$C_6$ being a substrate, the enzyme numbers $E_1$–$E_6$ of the enzymes with each compound of compound number $C_2$–$C_7$ being a product, and the enzyme number $E_4$ of the enzyme inhibited by the compound of compound number $C_6$ are recorded in the form of a list corresponding to the compound numbers $C_1$–$C_7$. Therefore, when access is made to the relation information file 33 using the compound number $C_1$–$C_7$ as a key, the apparatus can read out the enzyme numbers $E_1$–$E_6$ of the enzymes with each compound of compound number $C_1$–$C_7$ being a substrate or a product, and the enzyme number $E_4$ of the enzyme inhibited by the compound of compound number $C_6$. The main program 23 in this case is the same as FIG. 11 except that it excludes step S115 for calling the receptor information indication program, as shown in FIG. 43.

Next explained is a biochemical information computer program product (recording medium) according to an embodiment of the present invention.

Figure 44:
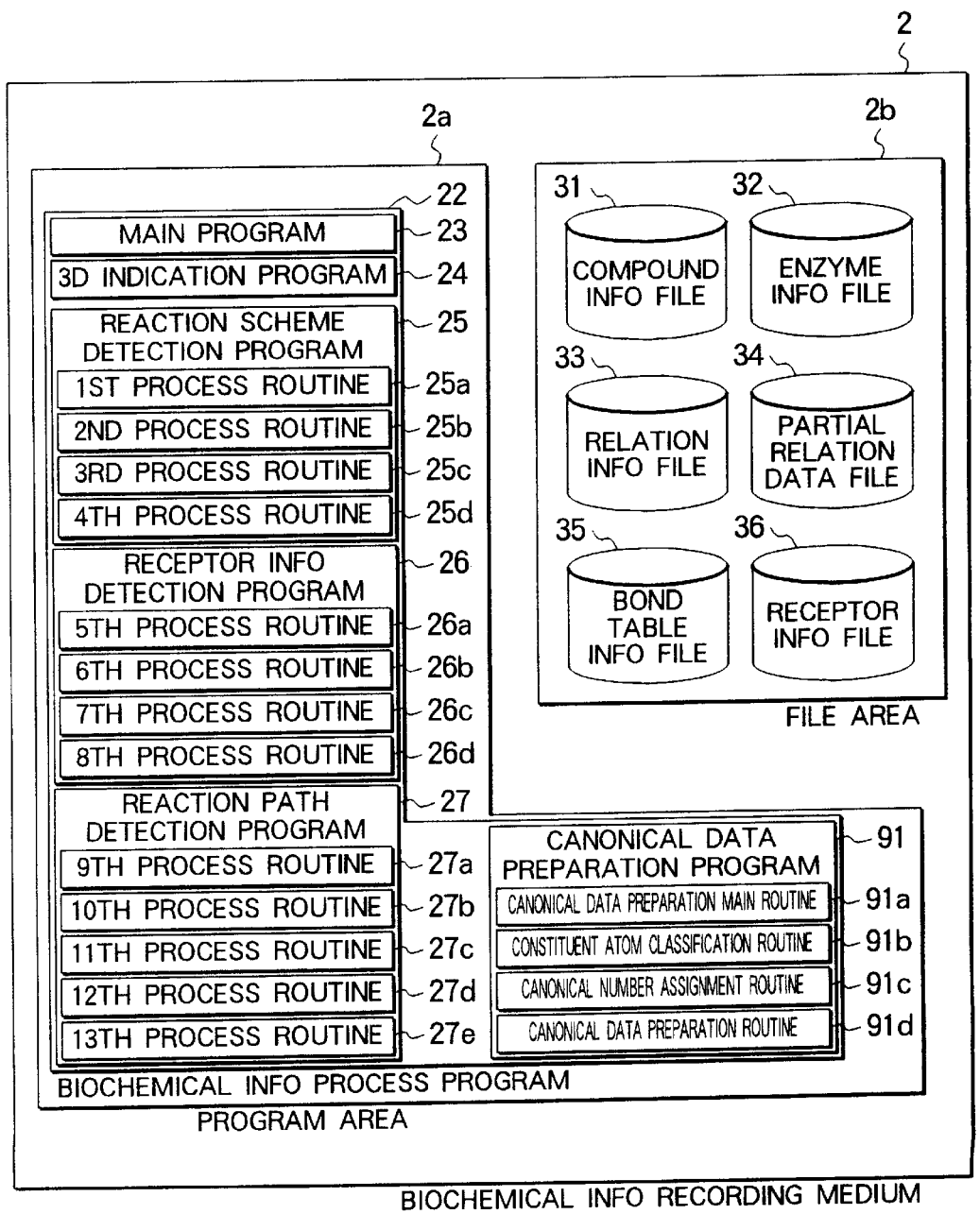
FIG. 44 is a block diagram to show the structure of an example of the biochemical information storage medium of the present invention.

FIG. 44 is a block diagram to show the structure of the biochemical information computer product (recording medium) 2 according to the embodiment of the present invention. As shown in the drawing, the biochemical information recording medium 2 of the present embodiment comprises a file area 2b for recording files, and a program area 2a for recording programs. Recorded in the file area 2b are a compound information file 31, an enzyme information file 32, a relation information file 33, a partial correlation data file 34, a bond table file 35, and a receptor information file 36.

Among them, the compound information file 31 stores a list showing the relation between compound numbers of compounds and canonical data corresponding to the compounds, and additional information (also referred to as reference data) about the compounds. The enzyme information file 32 stores a list showing the relation among enzyme numbers of enzymes, compound numbers of compounds being substrates for the enzymes, and compound numbers of compounds being products by the enzymes, and additional information about the enzymes.

Further, the relation information file 33 stores a list showing the relation among compound numbers of compounds, enzyme numbers of enzymes with a relevant compound being a substrate, enzyme numbers of enzymes with a relevant compound being a product, receptor numbers of receptors with a relevant compound being an agonist, and receptor numbers of receptors with a relevant compound being an antagonist. Furthermore, the partial correlation data file 34 is prepared to store the reaction path information, and the bond table file 35 to store the bond table data, respectively. Moreover, the receptor information file 36 stores a list showing the relation among receptor numbers of receptor, compound numbers of compounds being agonists for the receptors, compound numbers of compounds being antagonists for the receptors, and additional information about the receptors.

The biochemical information processing program 22 is recorded in the program area 2a. The biochemical information processing program 22 comprises the main program 23 for generally controlling the processing, the three-dimensional indication program 24 for three-dimensionally displaying the image data, the reaction scheme detection program 25 for detecting a chemical reaction scheme between compounds, the receptor information detection program 26 for detecting the additional information about receptor, and the reaction path detection program 27 for detecting a reaction path of plural compounds. The reaction scheme detection program 25 comprises the first process routine 25a to the fourth process routine 25d, the receptor information detection program 26 does the fifth process routine 26a to the eighth process routine 26d, and the reaction path detection program 27 the ninth process routine 27a to the thirteenth process routine 27e.

A disk type recording medium, for example, such as a flexible disk or a CD-ROM, is used as the biochemical information recording medium 2. Also, a tape type recording medium such as a magnetic tape may be applied.

Figure 45:
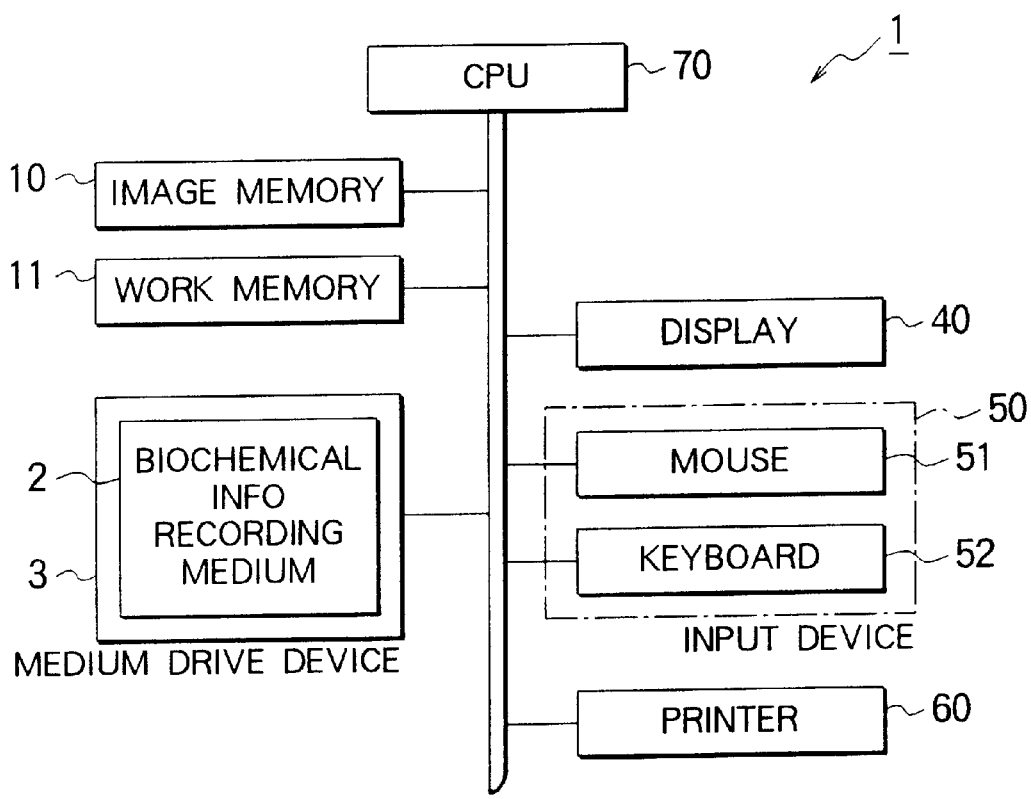
FIG. 45 is a block diagram to show the structure of an example of the biochemical information processing apparatus according to the present invention.
Figure 46:
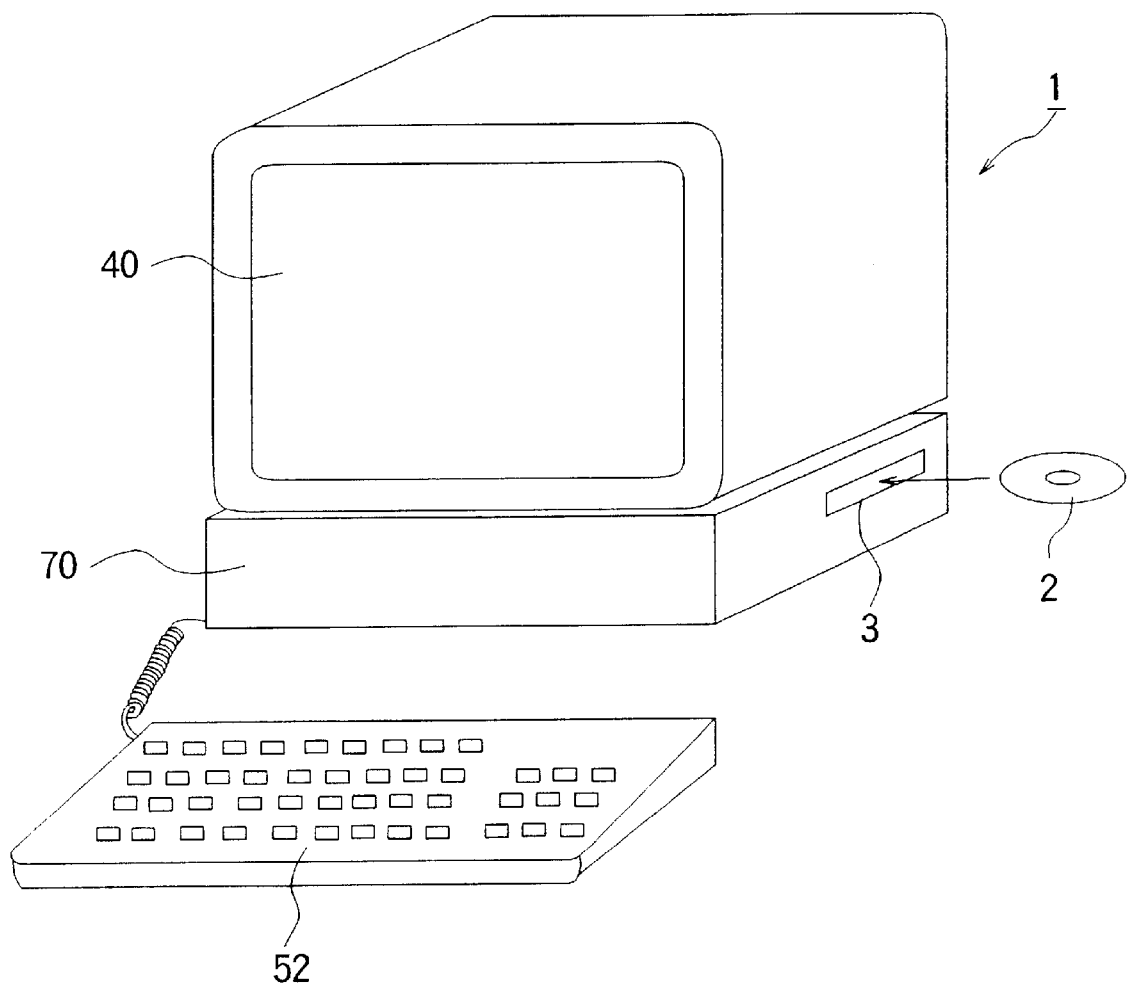
FIG. 46 is a perspective view to show an example of the biochemical information processing apparatus according to the present invention.

The biochemical information recording medium 2 of the present embodiment can be used in the information processing apparatus 1 shown in FIG. 45 and FIG. 46. In detail, the information processing apparatus 1 has a medium drive device 3 and the biochemical information recording medium 2 can be loaded in the medium drive device 3. Then this loading enables access to the biochemical information recorded in the biochemical information recording medium 2 by the medium drive device 3. This makes it possible to carry out the biochemical information processing program 22 recorded in the program area 20 by the information processing apparatus 1.

The structure of this information processing apparatus 1 is as follows. First, it is provided with the above-described medium drive device 3, the image memory 10 for storing the image data indicating the molecular structure diagram or the like of compound, the work memory (inner memory) 11 with resident operating system (OS), and the display 40 as display means. Also, it is provided with the input device 50 being input means having the mouse 51 for accepting input of image data and the keyboard 52 for accepting input of symbolic data, the printer 60 for outputting the image data or the like, and the CPU 70 for controlling execution or the like of the biochemical information processing program 22.

The medium drive device 3 applied is a flexible disk drive device, a CD-ROM drive device, a magnetic tape drive device, or the like, depending upon the biochemical information recording medium 2.

The detailed structure of the compound information file 31, enzyme information file 32, relation information file 33, partial correlation data file 34, bond table file 35, and receptor information file 36 recorded in the biochemical information recording medium 2 of the present embodiment is as described previously (FIG. 2 to FIG. 6).

The flow of data in the information processing apparatus 1 is also as described previously, the image data 80 input is converted into either of the bond table data 81, canonical data 82, and three-dimensional data 83 to be used, and the canonical data 82 is mainly used in the biochemical information program 22 recorded in the program area 2a, which is also as described previously (FIG. 7 to FIG. 10).

Next explained is the process of biochemical information processing program 22 recorded in the program area 2a of the biochemical information recording medium 1. This process is carried out by executing the biochemical information processing program 22 read out by the medium drive device 3. This execution first starts the main program 23 of the biochemical information processing program 22.

The details of the processes of main program 23, three-dimensional indication program 24, reaction scheme detection program 25, reaction path detection program 27, and receptor information detection program 26 thereafter are also as described previously (FIG. 11 to FIG. 15), and, for example as shown in FIG. 16 and FIG. 17, reaction scheme data or the like is indicated on the display 40.

Next explained is the canonical data preparation program suitably applicable to the present invention.

The biochemical information computer program product (recording medium) 2, being the embodiment of the present invention and shown in FIG. 44, is provided with the canonical data preparation program according to the present invention; that is, the biochemical information recording medium 2 is provided with the file area 2b for storing files and the program area 2a for storing programs. The bond table file 35, compound information file 31, etc. are stored in the file area 2b.

A plurality of bond tables 81 can be recorded in the bond table file 31. Recorded in a bond table 81 is characteristic data about each of atoms constituting a compound and bond pair data between atoms, and the canonical data preparation program 91 can access these data through the bond table 81.

The compound information file 31 and bond table 81 are as described previously (FIG. 3, FIG. 18A, and FIG. 18B).

The canonical data preparation program 91 is stored in the program area 2a. The canonical data preparation program 91 is a program for preparing the canonical data, based on the characteristic data about each of the atoms constituting the compound and the bond pair data between atoms. This canonical data preparation program 91 comprises the main routine 91a for generally controlling the processes and the constituent atom classification routine 91b for assigning a class number to each of atoms constituting a compound. The canonical data preparation program 91 also comprises the canonical number assignment routine 91c for assigning a canonical number to each atom, based on the class numbers, and the canonical data preparation routine 91d for preparing the canonical data based on the canonical numbers of the respective atoms.

The biochemical information recording medium 2 can be utilized in the information processing apparatus 1 shown in FIG. 45, as described previously. Pointing devices other than the mouse 51 include a tablet, a digitizer, a light pen, and so on, and the mouse 51 may be replaced by either one of these devices.

The schematic operation of the information processing apparatus 1 is also as described previously.

Next explained is the process of canonical data preparation program 91 stored in the program area 2a of biochemical information recording medium 2. This process is carried out by executing the canonical data preparation program 91 read out by the medium drive device 3. This execution first starts the main routine 91a of the canonical data preparation program 91.

The details of the processes of main routine 91a, constituent atom classification routine 91b, canonical number assignment routine 91c, and canonical data preparation routine 91d after that are also as described previously (FIG. 20 to FIG. 37), and the canonical data for uniquely specifying a compound can be attained in a short time.

The foregoing described the preferred embodiment of the biochemical information computer program product (recording medium) of the present invention, but it is noted that the present invention is not limited to the above embodiment.

Figure 47:
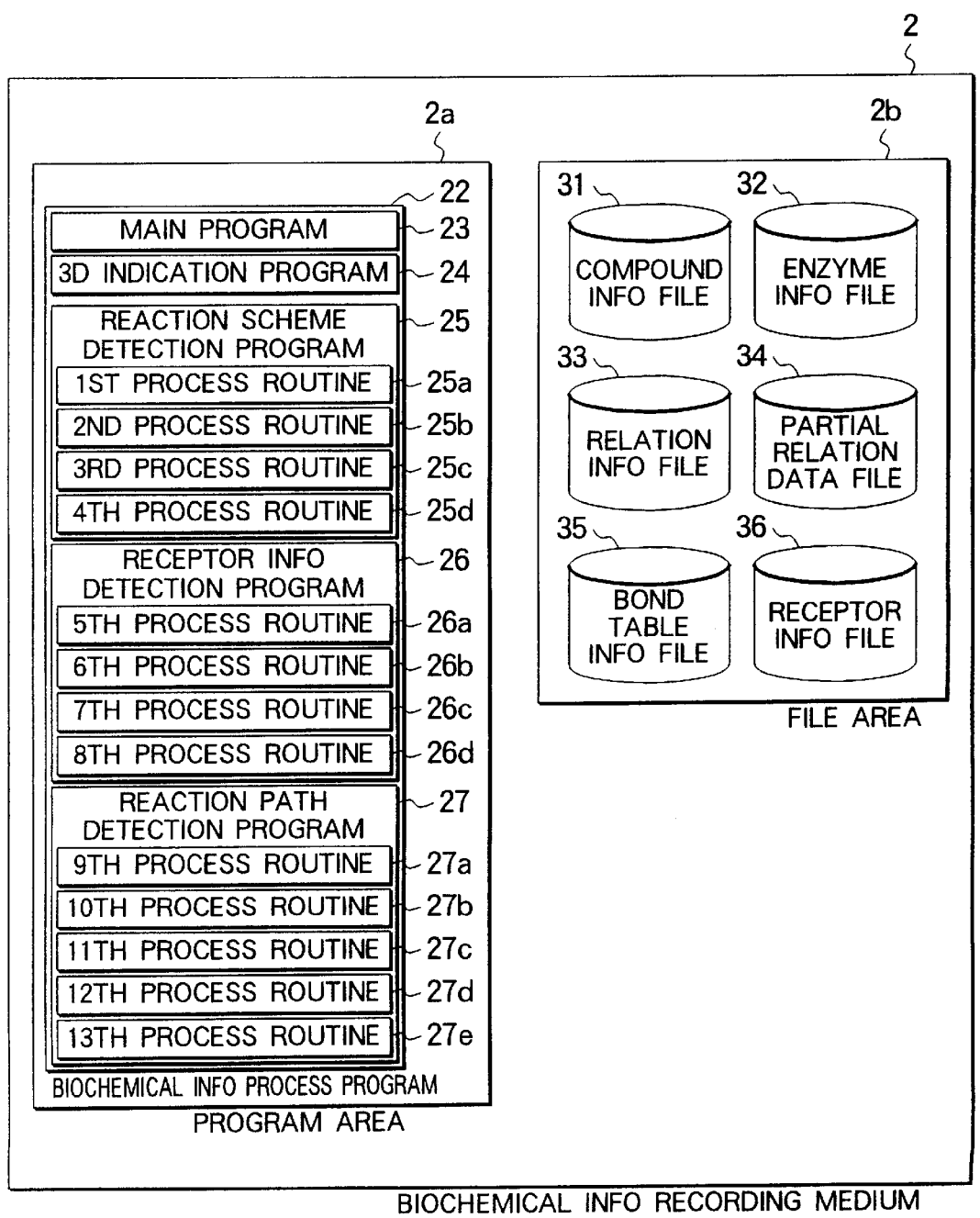
FIG. 47 is a block diagram to show the structure of another example of the biochemical information storage medium of the present invention.
Figure 48:
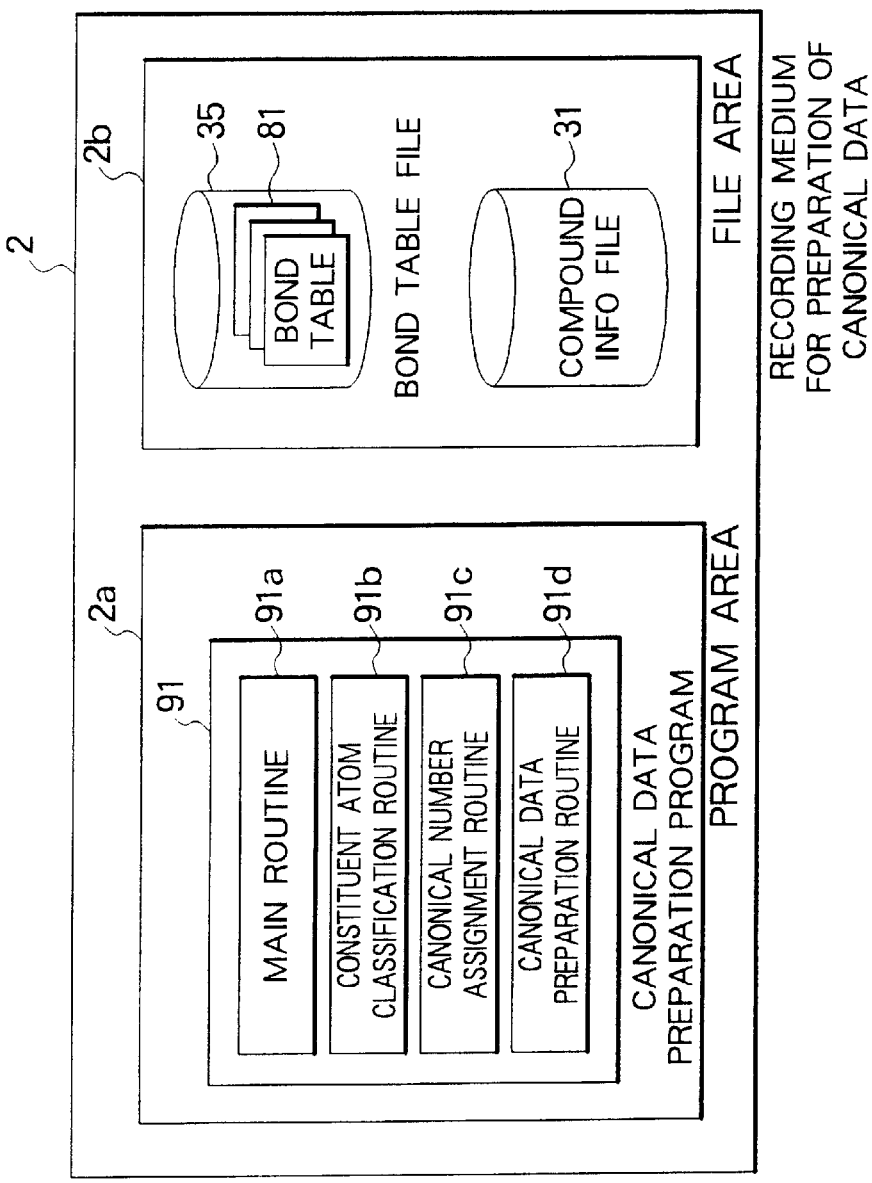
FIG. 48 is a block diagram to show the structure of an example of a recording medium for preparation of canonical data according to the present invention.

For example, the canonical data preparation program 91 according to the present invention does not have to be present together with the biochemical information processing program 22 according to the present invention in a single medium, but the canonical data preparation program 91 and biochemical information processing program 22 according to the present invention may be recorded respectively in separate media, as shown in FIG. 47 and FIG. 48.

Figure 49:
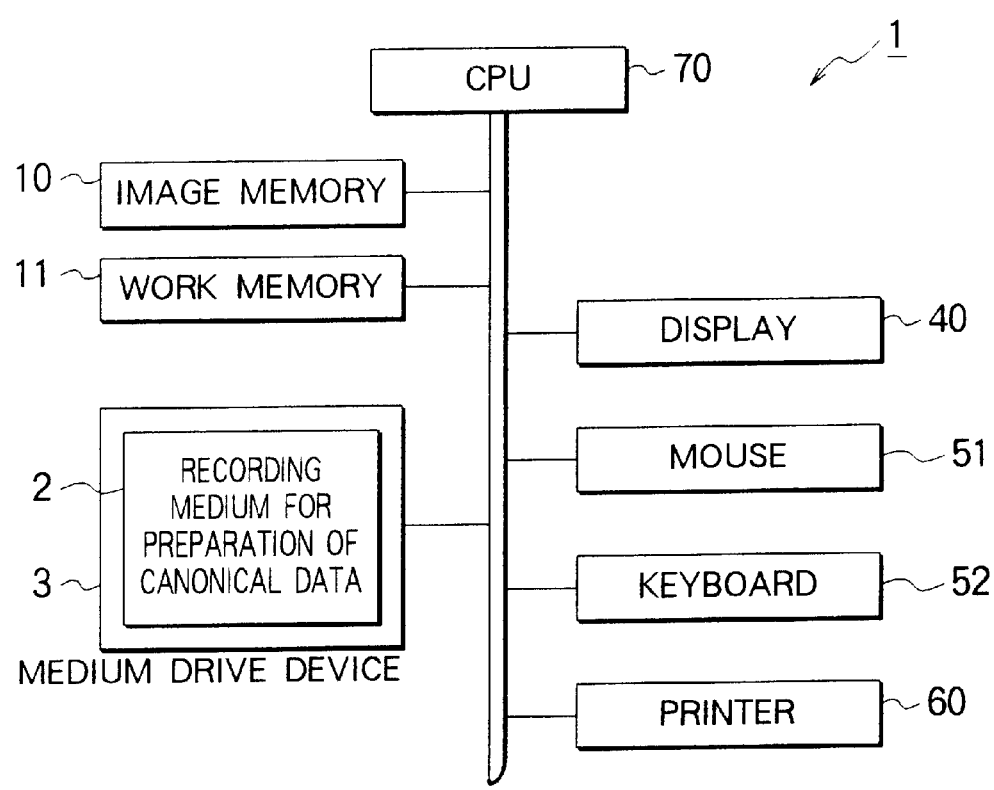
FIG. 49 is a block diagram to show the structure of another example of the canonical data preparing apparatus according to the present invention.

Namely, as shown in FIG. 48, the canonical data preparation program 91 according to the present invention may be singly formed as a storage medium 2 for preparation of canonical data. In this case, the storage medium 2 for preparation of canonical data can be utilized by the information processing apparatus 1 shown in FIG. 49. Namely, the information processing apparatus 1 is provided with the medium drive device 3, and the storage medium 2 for preparation of canonical data can be loaded in this device 3. Then this loading enables the medium drive device 3 to access the information stored in the storage medium 2 for preparation of canonical data. This enables the information processing apparatus 1 to carry out the canonical data preparation program 91 stored in the program area 2a. The storage medium 2 for preparation of canonical data applicable is, for example, a disk type storage medium such as a flexible disk or a CD-ROM, or a tape type storage medium such as a magnetic tape.

Figure 50:
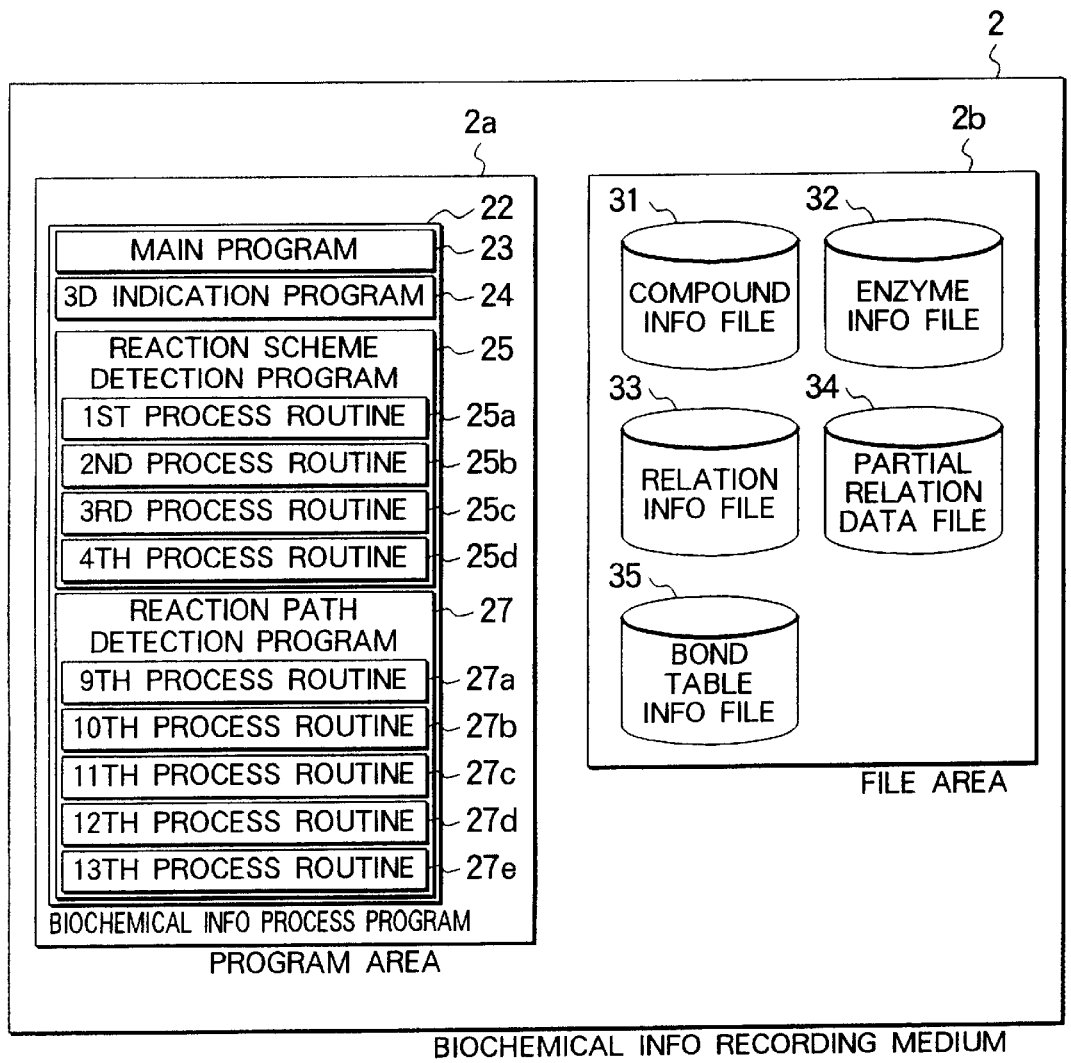
FIG. 50 is a block diagram to show the structure of still another example of the biochemical information storage medium of the present invention.

The biochemical information computer program product (recording medium) of the present invention does not have to comprise all of the reaction detection program 25, receptor information detection program 26, and reaction path detection program 27, but may be arranged, for example as shown in FIG. 50, to comprise the reaction scheme detection means (the reaction scheme detection program) 25 and the reaction path detection means (the reaction path detection program) 27, or may be arranged to comprise only either one of them. In this case, the receptor information file 36 is not necessary, and the main program 23 in this case is the same as that shown in FIG. 11 except that it excludes step S115 for calling the receptor information indication program, as shown in FIG. 43.

Without having to be limited to the above embodiments, the present invention can have a variety of modifications. For example, an amino acid sequence for defining the structure of enzyme, or a base sequence may be recorded in the column of reference data in the enzyme information file 32. Similarly, an amino acid sequence for defining the structure of receptor, or a base sequence may be recorded in the column of reference data in the receptor information file 36. Recording these sequences in the reference data makes possible utilization in connection with genetic information.

An anomaly in a function of a specific enzyme could cause a disease called as dysbolism. Thus, information about abnormal enzyme may be recorded in the column of reference data in the enzyme information file 32 to be used for search of dysbolism.

Further, the compound information file 31, enzyme information file 32, and relation information file 33 may include a record of information of conversion of foreign material occurring when a living body is dosed with the foreign material (which is a material not existing in living bodies originally).

Furthermore, the compound information file 31, enzyme information file 32, and relation information file 33 may include a record of information concerning production or conversion of substance by enzyme or micro-organism.

Furthermore, many drugs and agricultural chemicals themselves are enzyme inhibitors, agonists (agonistic materials), or antagonists (antagonistic materials). Then information about structures of drugs and agricultural chemicals or related information may be recorded as bio-related substances in the compound information file 31.

Yet further, information concerning safety, such as toxicity of chemical substance, may be recorded in the column of reference data in the compound information file 31 and may be used in connection with behavior of substance in a living body system.

Yet further, information in the field of nutrition may be recorded in the column of reference data of compound information file 31.

Furthermore, the indication method of reaction path may be modified, for example, in such a manner that the overall reaction path diagram is preliminarily prepared to be indicated in arbitrary position and scale and a desired reaction path part can be indicated by scrolling the screen top to bottom or left to right. The search of compound may adopt search by partial structure (partial identify search), search based on similarity, or the like. Further, the search of reaction path may be directed to a specific compound group, for example, such as metabolism of steroid.

The present processing apparatus or the present processing method may also be used as a compound database system, and each information of the compound database system may be recorded in the medium of the present invention. In this case, it is possible to perform search based on compound data of values of physical properties or the like. Based on the three-dimensional structure data of compound, a theoretical chemistry calculation function, such as calculation of molecular orbit or calculation of molecular force field, may be added to the present processing apparatus or the present processing method. Using the present processing apparatus or the present processing method, one can also know a reaction path when a specific enzyme is inhibited or inactivated or when an enzyme is defective.

Furthermore, the biochemical information recording medium of the present invention may include a record of information for knowing the reaction path when a specific enzyme is inhibited or inactivated or when an enzyme is defective.

INDUSTRIAL APPLICABILITY

As detailed above, the biochemical information processing apparatus and biochemical information processing method of the present invention can efficiently perform detection of reaction scheme, detection of receptor information, and detection of reaction path. Also, use of the biochemical information recording medium of the present invention enables to efficiently perform the detection of reaction scheme, detection of receptor information, and detection of reaction path.

In the detection of reaction scheme, first, reference is made to the list stored in the compound information file to read out a compound number corresponding to canonical data. Then, based on this compound number, reference is made to the relation information file to read out an enzyme number of an enzyme with this compound being a substrate or a product. Further, based on this enzyme number, reference is made to the enzyme information file to read out information about this enzyme. Then a chemical reaction scheme involving this compound is obtained from the information about the compound and enzyme thus read out.

In this way, by mutual reference to the compound information file, enzyme information file, and relation information file, various information can be efficiently acquired for an enzyme with a compound being a substrate or a product even in the case of the structure of the compound being used as a key.

Particularly, since the relation information file stores the list showing the relationship between compounds and enzymes with the compounds being substrates or products, it is easy to search for the relationship among a compound being a substrate, a compound being a product, and an enzyme for changing the substrate to the product, whereby a chemical reaction scheme can be attained efficiently In the detection of receptor information, first, reference is made to the list stored in the compound information file to read out a compound number corresponding to canonical data. Next, based on this compound number, reference is made to the relation information file to read out a receptor number of a receptor with this compound being an agonist or an antagonist. Further, based on this receptor number, reference is made to the reference information file to read out the additional information about this receptor. Then the additional information about the receptor thus read out is indicated on the display means.

In this way, by mutual reference to the compound information file, receptor information file, and relation information file, various information can be acquired efficiently for a receptor with a compound being an agonist or an antagonist even in the case of the structure of the compound being used as a key.

Particularly, since the relation information file stores the list showing the relationship between compounds and receptors with the compounds being agonists or antagonists, it is easy to search for the relationship among a compound being an agonist, a compound being an antagonist, and a receptor, whereby various information about the receptor can be obtained efficiently.

Further, in the detection of reaction path, first, reference is made to the list stored in the compound information file to read out a compound number corresponding to canonical data. Next, based on this compound number, reference is made to the relation information file to read out each of an enzyme number of an enzyme with this compound being a substrate and an enzyme number of an enzyme with this compound being a product. Further, based on these enzyme numbers, reference is made to the enzyme information file to read out a compound number of a compound being a substrate and a compound number of a compound being a product for every enzyme. Reading from the relation information file and the enzyme information file is repetitively carried out. Then, from a plurality of compound numbers and a plurality of enzyme numbers thus read out, a reaction path of these compounds is obtained.

In this way, by mutual reference to the compound information file, enzyme information file, and relation information file, it is possible to efficiently search a reaction path involving a plurality of compounds.

Particularly, since the relation information file stores the list showing the relationship between compounds and enzymes with the compounds being substrates or products, it is easy to search for the relationship among a compound being a substrate, a compound being a product, and an enzyme for changing the substrate to the product, whereby a reaction path involving a plurality of compounds can be obtained efficiently.

Further, employing the canonical data preparation means (the canonical data preparation program) according to the present invention, the characteristic data about each atom and the bonding pair data between atoms, accepted through the input means, is given to the canonical data preparation means. Then the canonical data preparation means prepares the canonical data based on these data within a short time. Also, by the canonical data preparation method according to the present invention, the canonical data is prepared within a short time, based on the characteristic data about each of atoms constituting a compound and the bonding pair data between atoms. As described, the canonical data prepared by the canonical data preparation means (the canonical data preparation program) and the canonical data preparation method according to the present invention is a very short string of character, numeral, and symbol, and the canonical data can be saved within a small storage area. Therefore, if the canonical data preparation means (the canonical data preparation program) and the canonical data preparation method according to the present invention are utilized in a compound/reaction database system, a use amount of storage area in the compound/reaction database system can be decreased remarkably.

What is claimed is:

1. A biochemical information processing apparatus comprising:

storage means for storing biochemical information about compounds and enzymes;

input means for accepting input of image data indicating said biochemical information or symbolic data indicating said biochemical information;

reaction scheme detection means for, when said input means accepts data about a compound being a substrate and/or a product, detecting a chemical reaction scheme involving said compound based on the data characterizing the compound as at least one of a substrate and a product; and display means for indicating a reaction scheme diagram of the chemical reaction scheme;

wherein said storage means comprises:

a compound information file storing a list showing a relation between compound numbers of compounds and canonical data corresponding to said compounds, and additional information about said compounds, an enzyme information file storing a list showing a relation among enzyme numbers of enzymes, compound numbers of compounds being substrates for said enzymes, and compound numbers of compounds being products by said enzymes, and additional information about said enzymes, and a relation information file storing a list showing a relation among compound numbers of compounds as a key, enzyme numbers of enzymes with said compound being a substrate, and enzyme numbers of enzymes with said compound being a product; and wherein said reaction scheme detection means comprises:

a first process portion for preparing from the data about a compound accepted through said input means said canonical data uniquely indicating a chemical structure of said compound, further searching said compound information file, based on the canonical data, and reading out a compound number corresponding to said canonical data when said canonical data exists in said compound information file, a second process portion for reading an enzyme number of an enzyme with the compound being a substrate or a product out of said relation information file, based on the compound number read out in said first process portion, a third process portion for reading a compound number of another compound constituting a reaction system together with the enzyme of the enzyme number read out in said second process portion and the compound of the compound number read out in said first process portion, and additional information about said enzyme out of said enzyme information file, and a fourth process portion for indicating a reaction scheme diagram of the compound whose image or symbolic data was accepted through said input means on said display means from the compound number read out in said first process portion, the enzyme number read out in said second process portion, and the compound number of the another compound read out in said third process portion, and further indicating the additional information about the enzyme read out in said third process portion on said display means.

2. The biochemical information processing apparatus according to claim 1, said biochemical information processing apparatus further comprising receptor information detection means for, when said input means accepts data about a compound, detecting additional information about a receptor based on the data with said compound being an agonist and/or an antagonist, wherein said storage means further stores biochemical information about receptors, and further comprises a receptor information file storing a list showing the relation between receptor numbers of receptors and compound numbers of compounds being agonists and/or antagonists for said receptors, and additional information about said receptors, wherein said relation information file stores a list to show the relation among the compound numbers of the compounds as a key, the enzyme numbers of the enzymes with said compound being a substrate, the enzyme numbers of the enzymes with said compound being a product, the receptor numbers of the receptors with said compound being an agonist, and the receptor numbers of the receptors with said compound being an antagonist; and wherein said receptor information detection means comprises:

a fifth process portion for preparing from data about a compound accepted through said input means said canonical data uniquely indicating a chemical structure of said compound, further searching said compound information file, based on said canonical data, and reading out a compound number corresponding to said canonical data when said canonical data exists in said compound information file, a sixth process portion for reading, based on the compound number read out in said fifth process portion, a receptor number of a receptor with the compound being an agonist or an antagonist out of said relation information file, a seventh process portion for reading at least additional information about the receptor of the receptor number read out in said sixth process portion out of said receptor information file, and an eighth process portion for indicating at least the additional information about the receptor read out in said seventh process portion on said display means.

3. The biochemical information processing apparatus according to claim 1, said biochemical information processing apparatus further comprising reaction path detection means for, when said input means accepts data about a predetermined compound selected from a plurality of compounds constituting a predetermined reaction path, detecting the predetermined reaction path of said plurality of compounds based on the data about the predetermined compound;

wherein said reaction path detection means comprises:

a fifth process portion for preparing from the data about the predetermined compound accepted through said input means said canonical data uniquely indicating a chemical structure of said predetermined compound, further searching said compound information file, based on the canonical data, and reading out a compound number corresponding to said canonical data when said canonical data exists in said compound information file, a sixth process portion for reading, based on the compound number read out in said fifth process portion, an enzyme number of an enzyme with the predetermined compound being a substrate and an enzyme number of an enzyme with the predetermined compound being a product out of said relation information file, a seventh process portion for reading, based on each enzyme number read out in said sixth process portion, a compound number of a compound being a substrate for said enzyme and a compound number of a compound being a product by said enzyme out of said enzyme information file, an eighth process portion for repeating said sixth process portion and said seventh process portion to obtain compounds and enzymes within the predetermined reaction path, and a ninth process portion for indicating from enzyme numbers read out in said sixth process portion and compound numbers read out in said seventh process portion a reaction scheme diagram of said plurality of compounds along the predetermined reaction path on said display means.

4. The biochemical information processing apparatus according to claim 1, wherein said input means accepts input of characteristic data about each of the atoms constituting a compound and bonding pair data between the atoms, wherein said biochemical information processing apparatus further comprises canonical data preparation means for preparing canonical data to uniquely specify a chemical structure of said compound, based on characteristic or bonding pair data accepted through said input means; and wherein said canonical data preparation means comprises:

a constituent atom classification process portion for classifying, based on the characteristic or bonding pair data accepted through said input means, the atoms into different classes each for equivalent atoms and assigning, to each atom, a different class number for each class, a canonical number assignment process portion for assigning canonical numbers uniquely corresponding to the structure of said compound to the respective atoms, based on the class numbers assigned to the respective atoms in said constituent atom classification process portion, and a canonical data preparation process portion for preparing said canonical data, based on the canonical numbers assigned to the respective atoms in said canonical number assignment process portion.

5. The biochemical information processing apparatus according to claim 4, wherein said constituent atom classification process portion assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path, wherein said canonical number assignment process portion is arranged so that when in a process for assigning a canonical number to each atom in the ascending order from 1 the canonical number 1 is given to an atom with a highest priority of said class number and thereafter canonical numbers up to the canonical number n are assigned, said canonical number assignment process portion selects an atom with a minimum canonical number out of atoms already having their respective canonical numbers and bonding to an atom having no canonical number yet and then gives a canonical number n+1 to an atom with a highest priority of said class number out of atoms bonding to a selected atom and having no canonical number yet, and wherein said canonical data preparation process portion gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

6. A biochemical information processing apparatus comprising:

storage means for storing biochemical information about compounds and enzymes;

input means for accepting input of image data indicating said biochemical information or symbolic data indicating said biochemical information;

reaction path detection means for, when said input means accepts data about a predetermined compound selected from a plurality of compounds constituting a predetermined reaction path, detecting the predetermined reaction path of said plurality of compounds based on the data about the predetermined compound; and display means for indicating a reaction scheme diagram of a chemical reaction scheme;

wherein said storage means comprises:

a compound information file storing a list showing the relation between compound numbers of compounds and canonical data corresponding to said compounds, and additional information about said compounds, an enzyme information file storing a list showing the relation among enzyme numbers of enzymes, compound numbers of compounds being substrates for said enzymes, and compound numbers of compounds being products by said enzymes, and additional information about said enzymes, and a relation information file storing a list showing the relation among compound numbers of compounds as a key, enzyme numbers of enzymes with said predetermined compound being a substrate, and enzyme numbers of enzymes with said predetermined compound being a product; and wherein said reaction path detection means comprises:

a first process portion for preparing from the data about the predetermined compound accepted through said input means said canonical data uniquely indicating a chemical structure of said predetermined compound, further searching said compound information file, based on the canonical data, and reading out a compound number corresponding to said canonical data when said canonical data exists in said compound information file, a second process portion for reading, based on the compound number read out in said first process portion, an enzyme number of an enzyme with the predetermined compound being a substrate and an enzyme number of an enzyme with the predetermined compound being a product out of said relation information file, a third process portion for reading, based on each enzyme number read out in said second process portion, a compound number of a compound being a substrate for said enzyme and a compound number of a compound being a product by said enzyme out of said enzyme information file, a fourth process portion for repeating said second process portion and said third process portion to obtain compounds and enzymes within the predetermined reaction path, and a fifth process portion for indicating from enzyme numbers read out in said second process portion and compound numbers read out in said third process portion a reaction scheme diagram of said plurality of compounds along the predetermined reaction path on said display means.

7. The biochemical information processing apparatus according to claim 6, said biochemical information processing apparatus further comprising receptor information detection means for, when said input means accepts data about a predetermined compound, detecting additional information about a receptor with said predetermined compound being an agonist and/or an antagonist based on the data about a predetermined compound;

wherein said storage means further stores biochemical information about receptors, and further comprises a receptor information file storing a list showing the relation between receptor numbers of receptors and compound numbers of compounds being agonists and/or antagonists for said receptors, and additional information about said receptors, wherein said relation information file stores a list to show the relation among the compound numbers of the compounds as a key, the enzyme numbers of the enzymes with said predetermined compound being a substrate, the enzyme numbers of the enzymes with said predetermined compound being a product, the receptor numbers of the receptors with said predetermined compound being an agonist, and the receptor numbers of the receptors with said predetermined compound being an antagonist; and wherein said receptor information detection means comprises:

a sixth process portion for preparing from data about the predetermined compound accepted through said input means said canonical data uniquely indicating a chemical structure of said predetermined compound, further searching said compound information file, based on said canonical data, and reading out a compound number corresponding to said canonical data when said canonical data exists in said compound information file, a seventh process portion for reading, based on the compound number read out in said sixth process portion, a receptor number of a receptor with the predetermined compound being an agonist or an antagonist out of said relation information file, an eighth process portion for reading at least additional information about the receptor of the receptor number read out in said seventh process portion out of said receptor information file, and a ninth process portion for indicating at least the additional information about the receptor read out in said eighth process portion on said display means.

8. The biochemical information processing apparatus according to claim 6, wherein said input means accepts input of characteristic data about each of the atoms constituting a compound and bonding pair data between the atoms, wherein said biochemical information processing apparatus further comprises canonical data preparation means for preparing canonical data to uniquely specify a chemical structure of said compound, based on the characteristic or bonding pair data accepted through said input means; and wherein said canonical data preparation means comprises:

a constituent atom classification process portion for classifying, based on each characteristic or bonding pair data accepted through said input means, the atoms into different classes each for equivalent atoms and assigning, to each atom, a different class number for each class, a canonical number assignment process portion for assigning canonical numbers uniquely corresponding to the structure of said compound to the respective atoms, based on the class numbers assigned to the respective atoms in said constituent atom classification process portion, and a canonical data preparation process portion for preparing said canonical data, based on the canonical numbers assigned to the respective atoms in said canonical number assignment process portion.

9. The biochemical information processing apparatus according to claim 8, wherein said constituent atom classification process portion assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path, wherein said canonical number assignment process portion is arranged so that when in a process for assigning a canonical number to each atom in the ascending order from 1 the canonical number 1 is given to an atom with a highest priority of said class number and thereafter canonical numbers up to the canonical number n are assigned, said canonical number assignment process portion selects an atom with a minimum canonical number out of atoms already having their respective canonical numbers and bonding to an atom having no canonical number yet and then gives a canonical number n+1 to an atom with a highest priority of said class number out of atoms bonding to a selected atom and having no canonical number yet, and wherein said canonical data preparation process portion gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

10. A biochemical information processing method, comprising:

providing an information processing apparatus having input means for accepting input of image data indicating said biochemical information or symbolic data indicating said biochemical information, display means for indicating a reaction scheme diagram of a chemical reaction scheme, and storage means for storing biochemical information about compounds and enzymes including a compound information file storing a list showing the relation between compound numbers of compounds and canonical data corresponding to said compounds, and additional information about said compounds, an enzyme information file storing a list showing the relation among enzyme numbers of enzymes, compound numbers of compounds being substrates for said enzymes, and compound numbers of compounds being products by said enzymes, and additional information about said enzymes, and a relation information file storing a list showing the relation among compound numbers of compounds as a key, enzyme numbers of enzymes with a predetermined compound being a substrate, and enzyme numbers of enzymes with said predetermined compound being a product;

in a first step, when said input means accepts data about a compound being a substrate and/or a product, preparing said canonical number data uniquely indicating a chemical structure of said compound from the data characterizing the compound as at least one of a substrate and a product, further searching said compound information file based on the canonical data, and reading out a compound number corresponding to said canonical data when said canonical data exists in said compound information file;

in a second step, reading an enzyme number of an enzyme with the compound being a substrate or a product out of said relation information file, based on the compound number read out in said first step;

in a third step, reading a compound number of another compound constituting a reaction system together with the enzyme of the enzyme number read out in said second step and said compound of the compound number read out in said first step, and additional information about said enzyme out of said enzyme information file; and in a fourth step, indicating a reaction scheme diagram of the compound whose image or symbolic data was accepted through said input means on said display means from the compound number read out in said first step, the enzyme number read out in said second step, and the compound number of the another compound read out in said third step, and further indicating the additional information about the enzyme read out in said third step on said display means.

11. The biochemical information processing method according to claim 10, further comprising:

further providing in said storage means stored biochemical information about receptors, and a receptor information file storing a list showing a relation between receptor numbers of receptors and compound numbers of compounds being agonists and/or antagonists for said receptors, and additional information about said receptors, said relation information file storing a list to show the relation among the compound numbers of the compounds as a key, the enzyme numbers of the enzymes with said predetermined compound being a substrate, the enzyme numbers of the enzymes with said predetermined compound being a product, the receptor numbers of the receptors with said predetermined compound being an agonist, and the receptor numbers of the receptors with said predetermined compound being an antagonist;

in a fifth step, when said input means accepts data about the compound, preparing said canonical data uniquely indicating a chemical structure of said compound, further searching said compound information file, based on said canonical data, and reading out a compound number corresponding to said canonical data when said canonical data exists in said compound information file;

in a sixth steps, reading, based on the compound number read out in said fifth step, a receptor number of a receptor with the compound being an agonist or an antagonist out of said relation information file;

in a seventh step, reading at least additional information about the receptor of the receptor number read out in said sixth step out of said receptor information file; and in an eighth step, indicating at least the additional information about the receptor read out in said seventh step on said display means.

12. The biochemical information processing method according to claim 10, said biochemical information processing method further comprising:

in a fifth step, when said input means accepts data about a predetermined compound selected from a plurality of compounds constituting a predetermined reaction path, preparing said canonical data uniquely indicating a chemical structure of said predetermined compound from the data about the predetermined compound, further searching said compound information file, based on the canonical data, and reading out a compound number corresponding to said canonical data when said canonical data exists in said compound information file;

in a sixth step, reading, based on the compound number read out in said fifth step, an enzyme number of an enzyme with the predetermined compound being a substrate and an enzyme number of an enzyme with the predetermined compound being a product out of said relation information file;

in a seventh step, reading, based on each enzyme number read out in said sixth step, a compound number of a compound being a substrate for said enzyme and a compound number of a compound being a product by said enzyme out of said enzyme information file;

in an eighth step, repeating said sixth step and said seventh step to obtain compounds and enzymes within the predetermined reaction path and;

in a ninth step, indicating from enzyme numbers read out in said sixth step and compound numbers read out in said seventh step a reaction scheme diagram of said plurality of compounds along the predetermined reaction path on said display means.

13. The biochemical information processing method according to claim 10, wherein said input means accepts input of characteristic data about each of the atoms constituting a compound and bonding pair data between the atoms, and wherein said biochemical information processing method further comprises:

a constituent atom classification step for classifying, based on the characteristic or bonding pair data accepted through said input means, the atoms into different classes each for equivalent atoms and assigning, to each atom, a different class number for each class;

a canonical number assignment step for assigning canonical numbers uniquely corresponding to the structure of said compound to the respective atoms, based on the class numbers assigned to the respective atoms in said constituent atom classification step; and a canonical data preparation step for preparing said canonical data enabling to uniquely specify a chemical structure of said compound, based on the canonical numbers assigned to the respective atoms in said canonical number assignment step.

14. The biochemical information processing method according to claim 13, wherein said constituent atom classification step assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path, wherein said canonical number assignment step is arranged so that when in a process for assigning a canonical number to each atom in the ascending order from 1 the canonical number 1 is given to an atom with a highest priority of said class number and thereafter canonical numbers up to the canonical number n are assigned, said canonical number assignment step selects an atom with a minimum canonical number out of atoms already having their respective canonical numbers and bonding to an atom having no canonical number yet and then gives a canonical number n+1 to an atom with a highest priority of said class number out of atoms bonding to said selected atom and having no canonical number yet, and wherein said canonical data preparation step gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

15. A biochemical information processing method, comprising:

providing an information processing apparatus having input means for accepting input of image data indicating said biochemical information or symbolic data indicating said biochemical information, display means for indicating a reaction scheme diagram of a chemical reaction scheme, and storage means for storing biochemical information about compounds and enzymes including a compound information file storing a list showing the relation between compound numbers of compounds and canonical data corresponding to said compounds, and additional information about said compounds, an enzyme information file storing a list showing the relation among enzyme numbers of enzymes, compound numbers of compounds being substrates for said enzymes, and compound numbers of compounds being products by said enzymes, and additional information about said enzymes, and a relation information file storing a list showing the relation among compound numbers of compounds as a key, enzyme numbers of enzymes with a predetermined compound being a substrate, and enzyme numbers of enzymes with said predetermined compound being a product;

in a first step, when said input means accepts data about the predetermined compound selected from a plurality of compounds constituting a predetermined reaction path, preparing said canonical data uniquely indicating a chemical structure of said predetermined compound from the data, further searching said compound information file, based on the canonical data, and reading out a compound number corresponding to said canonical data when said canonical data exists in said compound information file;

in a second step, reading, based on the compound number read out in said first step, an enzyme number of an enzyme with the predetermined compound being a substrate and an enzyme number of an enzyme with the predetermined compound being a product out of said relation information file;

in a third step, reading, based on each enzyme number read out in said second step, a compound number of a compound being a substrate for said enzyme and a compound number of a compound being a product by said enzyme out of said enzyme information file;

in a fourth step, repeating said second step and said third step to obtain compounds and enzymes within the predetermined reaction path; and in a fifth step, indicating from enzyme numbers read out in said second step and compound numbers read out in said third step a reaction scheme diagram of said plurality of compounds along the predetermined reaction path on said display means.

16. The biochemical information processing method according to claim 15, further comprising:

further providing in said storage means stored biochemical information about receptors, and a receptor information file storing a list showing a relation between receptor numbers of receptors and compound numbers of compounds being agonists and/or antagonists for said receptors, and additional information about said receptors, said relation information file storing a list to show the relation among the compound numbers of the compounds as a key, the enzyme numbers of the enzymes with said predetermined compound being a substrate, the enzyme numbers of the enzymes with said predetermined compound being a product, the receptor numbers of the receptors with said predetermined compound being an agonist, and the receptor numbers of the receptors with said predetermined compound being an antagonist;

in a sixth step, when said input means accepts data about the predetermined compound, preparing said canonical data uniquely indicating a chemical structure of said predetermined compound from the data about the predetermined compound, further searching said compound information file, based on said canonical data, and reading out a compound number corresponding to said canonical data when said canonical data exists in said compound information file;

in a seventh step, reading, based on the compound number read out in said sixth step, a receptor number of a receptor with the predetermined compound being an agonist or an antagonist out of said relation information file;

in an eighth step, reading at least additional information about the receptor of the receptor number read out in said seventh step out of said receptor information file; and in a ninth step, indicating at least the additional information about the receptor read out in said eighth step on said display means.

17. The biochemical information processing method according to claim 15, wherein said input means accepts input of characteristic data about each of the atoms constituting a compound and bonding pair data between the atoms; and wherein said biochemical information processing method further comprises:

a constituent atom classification step for classifying, based on the characteristic or bonding pair data accepted through said input means, the atoms into different classes each for equivalent atoms and assigning, to each atom, a different class number for each class, a canonical number assignment step for assigning canonical numbers uniquely corresponding to the structure of said compound to the respective atoms, based on the class numbers assigned to the respective atoms in said constituent atom classification step, and a canonical data preparation step for preparing said canonical data enabling to uniquely specify a chemical structure of said compound, based on the canonical numbers assigned to the respective atoms in said canonical number assignment step.

18. The biochemical information processing method according to claim 17, wherein said constituent atom classification step assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path, wherein said canonical number assignment step is arranged so that when in a process for assigning a canonical number to each atom in the ascending order from 1 the canonical number 1 is given to an atom with a highest priority of said class number and thereafter canonical numbers up to the canonical number n are assigned, said canonical number assignment step selects an atom with a minimum canonical number out of atoms already having their respective canonical numbers and bonding to an atom having no canonical number yet and then gives a canonical number n+1 to an atom with a highest priority of said class number out of atoms bonding to a selected atom and having no canonical number yet, and wherein said canonical data preparation step gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

19. A biochemical information computer program product used with an information processing apparatus having input means for accepting input of image data indicating biochemical information or symbolic data indicating biochemical information, display means for indicating a reaction scheme diagram of a chemical reaction scheme, and reading means for reading information out of a computer-usable medium, said computer program product comprising:

computer-usable medium, said computer-usable medium having a file area for recording a file and a program area for recording a program and having computer-readable file and program embodied in said computer-usable medium, for letting a reaction scheme diagram be searched for and be indicated by said display means, based on data input through said input means, said computer program product having, in said file area, a computer-readable compound information file for storing a list showing the relation between compound numbers of compounds and canonical data corresponding to said compounds, and additional information about said compounds, a computer-readable enzyme information file for storing a list showing the relation among enzyme numbers of enzymes, compound numbers of compounds being substrates for said enzymes, and compound numbers of compounds being products by said enzymes, and additional information about said enzymes, and a computer-readable relation information file for storing a list showing the relation among compound numbers of compounds as a key, enzyme numbers of enzymes with a compound being a substrate, and enzyme numbers of enzymes with said compound being a product, and having, in said program area, a computer-readable reaction scheme detection program for, when said input means accepts data about the compound being a substrate and/or a product, detecting a chemical reaction scheme involving said compound, based on the data characterizing the compound as at least one of a substrate and a product;

wherein said reaction scheme detection program comprises:

a first computer-readable process routine for preparing from the data about a compound accepted through said input means said canonical data uniquely indicating a chemical structure of said compound, further searching said compound information file, based on the canonical data, and reading out a compound number corresponding to said canonical data when said canonical data exists in said compound information file, a second computer-readable process routine for reading an enzyme number of an enzyme with the compound being a substrate or a product out of said relation information file, based on the compound number read out in said first computer-readable process routine, a third computer-readable process routine for reading a compound number of another compound constituting a reaction system together with the enzyme of the enzyme number read out in said second computer-readable process routine and said compound, and additional information about said enzyme out of said enzyme information file, and a fourth computer-readable process routine for indicating a reaction scheme diagram of the compound whose image or symbolic data was accepted through said input means on said display means from the compound number read out in said first computer-readable process routine, the enzyme number read out in said second computer-readable process routine, and the compound number of the another compound read out in said third computer-readable process routine, and further indicating the additional information about the enzyme read out in said third computer-readable process routine on said display means.

20. The biochemical information computer program product according to claim 19, said computer program product further having, in said file area, a computer-readable receptor information file storing a list showing the relation between receptor numbers of receptors and compound numbers of compounds being agonists and/or antagonists for said receptors, and additional information about said receptors, wherein said relation information file stores a list to show the relation among the compound numbers of the compounds as a key, the enzyme numbers of the enzymes with said compound being a substrate, the enzyme numbers of the enzymes with said compound being a product, the receptor numbers of the receptors with said compound being an agonist, and the receptor numbers of the receptors with said compound being an antagonist, and said computer program product further having, in said program area, a computer-readable receptor information detection program for, when said input means accepts data about a compound, detecting additional information about a receptor with said compound being an agonist and/or an antagonist, based on the data;

wherein said receptor information detection program comprises:

a fifth computer-readable process routine for preparing from data about the compound accepted through said input means said canonical data uniquely indicating a chemical structure of said compound, further searching said compound information file, based on said canonical data, and reading out a compound number corresponding to said canonical data when said canonical data exists in said compound information file, a sixth computer-readable process routine for reading, based on the compound number read out in said fifth process routine, a receptor number of a receptor with the compound being an agonist or an antagonist out of said relation information file, a seventh computer-readable process routine for reading at least additional information about the receptor of the receptor number read out in said sixth process routine out of said receptor information file, and an eighth computer-readable process routine for indicating at least the additional information about the receptor read out in said seventh process routine on said display means.

21. The biochemical information computer program product according to claim 19, said computer program product further having, in said program area, a computer-readable reaction path detection program for, when said input means accepts data about a predetermined compound selected from a plurality of compounds constituting a predetermined reaction path, detecting the predetermined reaction path of said plurality of compounds, wherein said reaction path detection program comprises:

a fifth computer-readable process routine for preparing from the data about the predetermined compound accepted through said input means said canonical data uniquely indicating a chemical structure of said predetermined compound, further searching said compound information file, based on the canonical data, and reading out a compound number corresponding to said canonical data when said canonical data exists in said compound information file, a sixth computer-readable process routine for reading, based on the compound number read out in said fifth computer-readable process routine, an enzyme number of an enzyme with the predetermined compound being a substrate and an enzyme number of an enzyme with the predetermined compound being a product out of said relation information file, a seventh computer-readable process routine for reading, based on each enzyme number read out in said sixth computer-readable process routine, a compound number of a compound being a substrate for said enzyme and a compound number of a compound being a product by said enzyme out of said enzyme information file, an eighth computer-readable process routine for repeating said sixth computer-readable process routine and said seventh computer-readable process routine to obtain compounds and enzymes within the predetermined reaction path, and a ninth computer-readable process routine for indicating from enzyme numbers read out in said sixth computer-readable process routine and compound numbers read out in said seventh computer-readable process routine a reaction scheme diagram of said plurality of compounds along the predetermined reaction path on said display means.

22. The biochemical information computer program product according to claim 19, wherein said input means accepts input of characteristic data about each of atoms constituting a compound and bonding pair data between atoms, wherein said computer program product further has, in said program area, a computer-readable canonical data preparation program for preparing canonical data to uniquely specify a chemical structure of said compound, based on the characteristic or bonding pair data accepted through said input means; and wherein said canonical data preparation program comprises:

a computer-readable constituent atom classification routine for classifying the atoms into different classes each for equivalent atoms and assigning, to each atom, a different class number for each class, a computer-readable canonical number assignment routine for assigning canonical numbers uniquely corresponding to the structure of said compound to the respective atoms, based on the class numbers assigned to the respective atoms in said constituent atom classification routine, and a computer-readable canonical data preparation routine for preparing said canonical data, based on the canonical numbers assigned to the respective atoms in said canonical number assignment routine.

23. The biochemical information computer program product according to claim 22, wherein said constituent atom classification routine assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path, wherein said canonical number assignment routine is arranged so that when in a process for assigning a canonical number to each atom in the ascending order from 1 the canonical number 1 is given to an atom with a highest priority of said class number and thereafter canonical numbers up to the canonical number n are assigned, said canonical number assignment routine selects an atom with a minimum canonical number out of atoms already having their respective canonical numbers and bonding to an atom having no canonical number yet and then gives a canonical number n+1 to an atom with a highest priority of said class number out of atoms bonding to a selected atom and having no canonical number yet, and wherein said canonical data preparation routine gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

24. The biochemical information computer program product according to claim 19, wherein said computer-usable medium is a disk type recording medium or a tape type recording medium.

25. A biochemical information computer program product used with an information processing apparatus having input means for accepting input of image data indicating biochemical information or symbolic data indicating biochemical information, display means for indicating a reaction scheme diagram of a chemical reaction scheme, and reading means for reading information out of a computer-usable medium, said computer program product comprising:

the computer-usable medium, said computer-usable medium having a file area for recording a file and a program area for recording a program and having computer-readable file and program embodied in said computer-usable medium, for letting the reaction scheme diagram be searched for and be indicated by said display means, based on data input through said input means;

said computer program product having, in said file area, a computer-readable compound information file for storing a list showing the relation between compound numbers of compounds and canonical data corresponding to said compounds, and additional information about said compounds, a computer-readable enzyme information file for storing a list showing the relation among enzyme numbers of enzymes, compound numbers of compounds being substrates for said enzymes, and compound numbers of compounds being products by said enzymes, and additional information about said enzymes, and a computer-readable relation information file for storing a list showing the relation among compound numbers of compounds as a key, enzyme numbers of enzymes with a predetermined compound being a substrate, and enzyme numbers of enzymes with said compound being a product, and having, in said program area, a computer-readable reaction path detection program for, when said input means accepts data about a predetermined compound selected from a plurality of compounds constituting a predetermined reaction path, detecting the predetermined reaction path of said plurality of compounds, based on the data about the predetermined compound;

wherein said reaction path detection program comprises:

a first computer-readable process routine for preparing from the data about the predetermined compound accepted through said input means said canonical number data uniquely indicating a chemical structure of said predetermined compound, further searching said compound information file, based on the canonical data, and reading out a compound number corresponding to said canonical data when said canonical data exists in said compound information file, a second computer-readable process routine for reading, based on the compound number read out in said first computer-readable process routine, an enzyme number of an enzyme with the predetermined compound being a substrate and an enzyme number of an enzyme with the predetermined compound being a product out of said relation information file, a third computer-readable process routine for reading, based on each enzyme number read out in said second computer-readable process routine, a compound number of a compound being a substrate for said enzyme and a compound number of a compound being a product by said enzyme out of said enzyme information file, a fourth computer-readable process routine for repeating said second computer-readable process routine and said third computer-readable process routine to obtain compounds and enzymes within the predetermined reaction path, and a fifth computer-readable process routine for indicating from enzyme numbers read out in said second computer-readable process routine and compound numbers read out in said third computer-readable process routine a reaction scheme diagram of said plurality of compounds along the predetermined reaction path on said display means.

26. The biochemical information computer program product according to claim 25, said computer program product further having, in said file area, a computer-readable receptor information file storing a list showing the relation between receptor numbers of receptors and compound numbers of compounds being agonists and/or antagonists for said receptors, and additional information about said receptors, wherein said relation information file stores a list to show the relation among the compound numbers of the compounds as a key, the enzyme numbers of the enzymes with said compound being a substrate, the enzyme numbers of the enzymes with said compound being a product, the receptor numbers of the receptors with said compound being an agonist, and the receptor numbers of the receptors with said compound being an antagonist, and said computer program product further having, in said program area, a computer-readable receptor information detection program for, when said input means accepts data about a compound, detecting additional information about a receptor with said compound being an agonist and/or an antagonist based on the data about the compound;

wherein said receptor information detection program comprises:

a sixth computer-readable process routine for preparing from data about the compound accepted through said input means said canonical data uniquely indicating a chemical structure of said compound, further searching said compound information file, based on said canonical data, and reading out a compound number corresponding to said canonical number data when said canonical data exists in said compound information file, a seventh computer-readable process routine for reading, based on the compound number read out in said fifth computer-readable process routine, a receptor number of a receptor with the compound being an agonist or an antagonist out of said relation information file, an eighth computer-readable process routine for reading at least additional information about the receptor of the receptor number read out in said seventh computer-readable process routine out of said receptor information file, and a ninth computer-readable process routine for indicating at least the additional information about the receptor read out in said eighth computer-readable process routine on said display means.

27. The biochemical information computer program product according to claim 25, wherein said input means accepts input of characteristic data about each of the atoms constituting a compound and bonding pair data between the atoms, wherein said computer program product further has, in said program area, a computer-readable canonical data preparation program for preparing canonical data to uniquely specify a chemical structure of said compound, based on the characteristic or bonding pair data accepted through said input means; and wherein said canonical data preparation program comprises:

a computer-readable constituent atom classification routine for classifying the atoms into different classes each for equivalent atoms and assigning, to each atom, a different class number for each class, a computer-readable canonical number assignment routine for assigning canonical numbers uniquely corresponding to the structure of said compound to the respective atoms, based on the class numbers assigned to the respective atoms in said constituent atom classification routine, and a computer-readable canonical data preparation routine for preparing said canonical data, based on the canonical numbers assigned to the respective atoms in said canonical number assignment routine.

28. The biochemical information computer program product according to claim 27, wherein said constituent atom classification routine assigns three types of attributes ($a_i$, $b_{ij}$, $d_{ij}$) to each atom and, utilizing the fact that atoms different in even only one of these attributes can be determined to be not equivalent, assigns a different class number for each equivalent atom to each atom, where among said three types of attributes ($a_i$, $b_{ij}$, $d_{ij}$), $a_i$ is a kind number of an atom of input number i, $b_{ij}$ is the number of bonds adjoining the atom of input number i and having a bond kind number being j, and $d_{ij}$ is the number of routes that can be traced from the atom of input number i through j bonds in the shortest path;

wherein said canonical number assignment routine is arranged so that when in a process for assigning a canonical number to each atom in the ascending order from 1 the canonical number 1 is given to an atom with a highest priority of said class number and thereafter canonical numbers up to the canonical number n are assigned in that manner, said canonical number assignment routine selects an atom with a minimum canonical number out of atoms already having their respective canonical numbers and bonding to an atom having no canonical number yet and then gives a canonical number n+1 to an atom with a highest priority of said class number out of atoms bonding to a selected atom and having no canonical number yet; and wherein said canonical data preparation routine gives three types of attributes ($P_i$, $T_i$, $S_i$) to each atom and aligns these attributes in line to prepare said canonical data, where among said three types of attributes ($P_i$, $T_i$, $S_i$), $P_i$ is a canonical number of an atom bonding to an atom of canonical number i and having a minimum canonical number, $T_i$ is a symbol for a type of a bond between the atom of canonical number i and the atom of canonical number $P_i$, and $S_i$ is a symbol for a kind of the atom of canonical number i.

29. The biochemical information computer program product according to claim 25, wherein said computer-usable medium is a disk type recording medium or a tape type recording medium.

* * * * *